United States Patent [19]
Kondo et al.

[11] Patent Number: 5,470,971
[45] Date of Patent: Nov. 28, 1995

[54] STRESS-INDUCED PROTEINS, GENES CODING THEREFOR, TRANSFORMED CELLS OF ORGANISMS, METHODS AND APPLICATIONS

[75] Inventors: Keiji Kondo, Edison; Masayori Inouye, Bridgewater, both of N.J.

[73] Assignee: The University of Medicine and Dentistry of New Jersey, Newark, N.J.

[21] Appl. No.: 667,276

[22] Filed: Mar. 11, 1991

[51] Int. Cl.$^6$ ............................ C12N 15/31; C12N 15/81
[52] U.S. Cl. ...................... 536/23.7; 536/24.1; 435/69.1; 435/172.3; 435/252.3; 435/254.2; 435/254.21; 435/320.1
[58] Field of Search .................................. 536/27.7, 24.1; 435/172.3, 320.1, 252.3, 69.1, 254.2, 254.21

[56] References Cited

PUBLICATIONS

Borkovich, K. A., et al. (1989), "hsp82 is an essential protein that is required in higher concentrations for growth . . . " etc., Mol. Cell. Biol., 9, 3919–3930.
Broach, J. R. et al., (1979), "Transformation in yeast: development of a hybrid cloning vector and isolation of the CAN1 gene", Gene, 8, 121–133.
Caizergues–Ferrer, M. et al. (1989), "Nucleolin from *Xenopus laevis*: cDNA cloning and expression during development", Genes and Dev., 3, 324–333.
Craig, E. and Jacobsen, K. (1984), "Mutations of the heat inducible 70 kilodalton genes of yeast confer temperature sensitive growth", Cell, 38, 841–849.
Finely, D. et al. (1987), "The yeast polyubiquitin gene is essential for resistance to high temperatures, starvation, and other stresses", Cell, 48, 1035–1046.
Goldstein et al. (1990), "Major cold shock protein of *Escherichia coli*", Proc. Natl. Acad. Sci. USA, 87, 283–287.
Jones, P. C. et al. (1987), "Induction of proteins in response to low temperature in *Escherichia coli*", J. Bacteriol., 169, 2092–2095.
Lindquist, S. and Craig, E. A. (1988), "The heat shock proteins", Annu. Rev. Genet., 22, 631–677.
Maniak, M. and Nellen, W. (1988), "A developmentally regulated membrane gene in *Dictyostelium discoideum* is also . . . "etc. Mol. Cell. Biol., 8, 153–159.
Marguet, D. and Lauquin, G. J. —M. (1986), "The yeast srp gene: positive modulation by glucose of its transcriptional . . . "etc. Biochem. Biophys. Res. Commum, 138, 297–303.
Marguet, D. et al. (1988), "Yeast gene SRP1 (Serine–rich protein) Intragenic repeat structure . . . "etc., J. Mol. Biol., 202, 455–470.
Muller–Taubenberger, A. et al. (1988), "Ubiquitin gene expression in Dictyostelium is induced by heat . . . "etc., J. Cell. Sci., 90, 51–58.
Neidhardt, F. C. et al. (1984), "The genetics and regulation of heat–shock proteins" Ann. Rev. Genet., 18, 295–329.
Nicolet, C. M. and Craig, E. A. (1989), "Isolation and characterization of STI1, a stress inducible gene . . . "etc., Mol. Cell. Biol., 9, 3638–3646.
Pelham, H. R. B. (1989), "Heat shock and the sorting of luminal ER proteins", EMBO J., 8, 3171–3176.
Petko, L. and Lindquist, S. (1986), "Hsp26 is not required for growth at high termperatures, nor for . . . "etc., Cell, 45, 885–894.
Sanchez, Y. and Lindquist, S. L. (1990), "Hsp104 required for induced thermotolerance", Science, 248, 1112–1115.
Schlesinger, M. J. (1990), "Heat shock proteins", J. Biol. Chem., 265, 12111–12114.
Srivastava, M. et al. (1990) "Genomic Organization and Chromosmal Localization of the Human Nucleolin Gene", JBC, 265, 14922–14931.
Werner–Washburne, M. et al. (1987), "Complex interactions among members of an essential sub–family of hsp70 . . . "etc., Mol. Cell. Biol., 7, 2568–2577.
Werner–Washburne, M. et al. (1989), "Yeast hsp70 RNA levels vary in response to the physiological . . . "etc., J. Bacteriol., 171, 2680–2688.
Marguet et al. J Mol. Biol. 202:455–470 (1988).

*Primary Examiner*—Jacqueline Stone
*Assistant Examiner*—J. LeGuyader
*Attorney, Agent, or Firm*—Weiser & Associates

[57] ABSTRACT

Genes (and portions thereof) which are stress-inducible, e.g., by cold-shock which encode useful proteins. The proteins contribute to confer thermo-tolerance and/or contribute to confer low temperature tolerance to organisms, like eucaryotes or procaryotes. Typical genes encoding such proteins and homologous genes encoding proteins with equivalent properties are discussed. Nucleotide sequences encoding such proteins, recombinant replicable expression vehicles which comprise DNA constructs which encode such proteins and competent transformed organisms like eucaryotes are discussed. The production of valuable fermentation products and of biologically active proteins under conditions outside the normal or optimum physiological growth conditions are described.

23 Claims, 26 Drawing Sheets

FIG. 4

```
-474                                                        GATCTGGTTATGGTTTTCTTGAC
-450   TATAACCTTAATTATGAGACTAATGTCTTCGGGAGGTCCCTTTTCCGACTCTTTTCCGATTTTCCGGTTGAAGAATGTACTGTGGTTTG
-360   AATCCTACGGCAGTTATTGCGGCGGGTTGGCCGTTTGGCCCTTTCTTCAAGATTGTGATGGAAATAATTGATTGTTCCGGAACATGTCTTATTT
-270   TCTAAAAGCATCTTTTTTTCTCGGTCGTTGCTTCATTCCATCACCATTAATAATAAGTACATTGGCAGCCCTCTTCAAACGTCAATTATTCTCGCTTGC
-180   CCTCCTTTGTTCGAGCTACTGCGGTTGGACCCGAAATATAAGGCATTCAATCAGTAACAATAATTGCTATTGCGCCGTCGCTGACACCAGCCGCCGCCGAAACTGCTGAATTGCAA
-90    CTAACTTTGTTCGGACCCGAAATATAAGGCATTCAATCAGTAACAATAATTGCTATTGCGCCGTCGCTGACACCAGCCGCCGCCGAAACTGCTGAATTGCAA

1    ATGTCCGTTTCCAAGATTGCTTTCGTTTTAAGTGCCATTGCCTCTTTGGCCGTCGCTGACACCAGCCGCCGCCGAAACTGCTGAATTGCAA
  1     M  S  V  S  K  I  A  F  V  L  S  A  I  A  S  L  A  V  A  D  T  S  A  A  E  T  A  E  L  Q

91    GCTATTATCGGTGACATCAACTCTCATCTTCTGACTACTTGGGTCTAGAAACTGGCAACAGTGGATTCCAAATTCCATCTGATGTCTTG
 31     A  I  I  G  D  I  N  S  H  L  S  D  Y  L  G  L  E  T  G  N  S  G  F  Q  I  P  S  D  V  L

181    AGTGTGTATCAACAAGTCATGACTTACACCGATGACGGCTTACACTACCTTGTTAGTGAATTGGACTTTGATGCTATCACTAAGACAATT
 61     S  V  Y  Q  Q  V  M  T  Y  T  D  D  A  Y  T  T  L  F  S  E  L  D  F  D  A  I  T  K  T  I

271    GTTAAATTGCCATGGTACCACAAGATTGAGTTCTGAAATCGCTGCTGCTCTCCGAAGCTACACCTCTTCTTCCGAGCCTGCATCT
 91     V  K  L  P  W  Y  T  T  R  L  S  S  E  I  A  A  A  L  A  S  V  S  P  A  S  S  E  A  A  S

361    TCTTCCGAGGCTGCATCTGCCATCTCTTCCAAGGCTGCATCTTCTTCCGAAGCTACATCCTCTTCTGCCTCTGCGCCCATCTCT
121     S  S  E  A  A  S  S  S  K  A  A  S  S  S  E  A  T  S  S  A  A  P  S  S  S  A  A  P  S  S

451    TCTGCTGCCCATCATCATCGCCGAATCATCTCTAAGGCCGTTTCTTCTTCTGCGGCCAACTACCTCTTCTGTCAGCACTTCTACA
151     S  A  A  P  S  S  S  A  E  S  S  S  K  A  V  S  S  S  V  A  P  T  T  S  S  V  S  T  S  T

541    GTCGAAACTGCTTCCAATGCCGGTCAAAGAGTCAATGCGGGCGCTGCCTCTTTCGGTGTCGTTGCAGGTGCAGCCTGCTTATTGTTA
181     V  E  T  A  S  N  A  G  Q  R  V  N  A  G  A  A  S  F  G  A  V  V  A  G  A  A  L  L  L

631    TAAAGGGAACCCTTTTACAACAAATATTTGAAAAATTACCTCCATTATTATACCTTCTCTTCTTATGTAATTGTTAGTTCGAAAATTTTTC
         *

721    TTCATTAATATAATCAACTTCTAAAAACTTCTAAAAACGTTCTCTTTTTTCGAGATTAGTGCTTCTTCCCAATCCGTAAGAAATGTTCCT
811    TTCTTGACAATTGGCACCAGCTGGCTGCGTTGCTCGAAAACTACTCTCTTTTTATTTTTAATTTACGAACGATTATCTTTCGAAGGAAC
901    GACCAAACGAGCTAAATATGGCATCGCCAACGTTAAAAAAATGGACCCTACCGAAGACGTTATTATGCCAAGGCGCAGCGAAGAGTCTT
991    TCTCCTTGAGAAAAAAATATGCATGAAACAAAATAGACAGGACCAGACCCTCTTCGGGAAAAAAGTCAAGATTTAACACGTGGCTACACC
1081   GGCTGGCTTACAACCAACCAACATAAGATC
```

FIG. 9

```
            1                                                 50*
TIP1  MSVSKIAFVLSAIASLAVADTSAAETAELQAIIGDINSHLSDYLGLETGN
       ||| :: ||||:||  ||||:|| ::   |  ::  |||  ::
SRP1  MAYTKIAL.FAAIAALASAQT.QDQINELNVILNDVKSHLQEYISLASDS
       1                          *                    *

TIP1  SG.....FQIPSDVLSVYQQVMTYTDDAYTTLFSELDFDAITKTIVKLPWY
       :|      ||| ||:::  |  |||||:||  :: ||:  :||| |||
SRP1  SSGFSLSSMPAGVLDIGMALASATDDSYTTLYSEVDFAGVSKMLTMVPWY
      50*                                              1*

TIP1  TTRLSSEI.....................AAALASVSPASSEAASSSEA
       |: ||                         || ||| ||| |||||||
SRP1  SSRLEPALKSLNGDASSSAAPSSSAAPTSSAAPTSSAAPSSSAAPSSSEA
      100*                     *1  150*            *3

TIP1  ASSSKAASSEA.TSSAAPSSSSAAPSSS.AESSSKAVSSSVAPT
      |||||||||||  |::|||||  ||||| |||||| ||||  |
SRP1  KSSSAAPSSSEAKSSSSAAPSSSEAKSSSSAAPSSSTEAKI
      150*          4           *5          *6*        *7

TIP1  TSSVSTSTVETASNAGQ............RVNAGAA.....SFGAVVAG
       ||| |    ||:||||               |||:|     ||| |||
SRP1  TSAAPSSTGAKTSAISQITDGQIQATKAVSEQTENGAAKAFVGMGAGVVA
      200*        8                              200*

TIP1  AAALLL
      ||| ||
SRP1  AAAMLL
                                                      *254
```

FIG. 11

```
                              RNP 1                                              RNP 2

NOL1       1  PAT IFVGRL SWS IDDEWL KKEFEHI GGVI GARVI YERGTD RSRGYGYV DFENKSYAEKA IQEMOGKE IDGRP INCDMSTSKPAGN
NOL1       2  SDT LFLGNL SFNADRDA IFELFAKHGEVVSVRI PTHPE TE QPKGFGYV QFSNMEDAKKAL DAL OGEY I DNRPVRL DFSSPRPNND
NUCLEOLIN  1  AFN LFVGNL NFNKSAPELKTGI SDVFAKNDLAVVDVR. IGMTRKFGYV DFESAEDLEKAL . EL TGLKVFGNE IKLEKPKGKDSKK
NUCLEOLIN  2  ART LLAKNL PYKVTQDELKEVFEDAAE IRLVSKD...... GKSKGIAYI EFKTEADAEKTFEEKQGTE IDGRSI SL YYTGEKKGON
NUCLEOLIN  3  SKT LVILSNL SYSATEETL QEVFEKATF IKVPQNQN.... GKSKGYAFI EFASFEDAKEALNSCNKRE I EGRAIRLE LQGPRGSPN
NUCLEOLIN  4  SKT LFVKGL SEDTTEETLKESFD...GSVRARI VTDRET . GSSKGFGFV DFNSEEDAKEAME... DGE IDGNKVTLDWAKPKGEGG
Y PABP     1  SAS LYVGDL EPSVSEAHL YDIFSPIGSVSSIRVCRDAI TKTSLGYAYV NFNDHEAGRKA IEQLNYTP IKGRLCRIMWSQ. RDPSL
Y PABP     2  SGN IFIKNL HPDIDNKAL YDTFSVFGDILSSKI . ATDENGKSLKGFGFV HFEEEGAAKEA IDALNGMLLNGOE IYAPHL SRKERD
Y PABP     3  YTN LYVKNI NSETTDEOFQELFAKFGPIVSASL . EKDADGKLKGFGFV NYEKHEDAVKAVEALNDSELNGEKL YVGRAQKNERM
Y PABP     4  GVN LFVKNL DDSVDDEKLEEEFAPYGTI TSAKVMRTE . NGKSKGFGFV CFSTPEEATKA ITEKNQQI VAGKPL YVA I AQRKDVRR
H U1 70K   1  FKT LFVARV NYDTTESKL RREFEVYGPIKRIHMVYSKRSG KPRGYAFI EYEHERDMHSAYKHADGKK I DGRRVL VDVERGRTVKG

--T LFVKNL  ----EE-L -E-F---G-I-----V-------GKSKGFGFV -F----EDA-KA I E---G---I -GR-I--------K-------R
              G           DD   D                                   R YAYI             LD     V    V
```

FIG. 14A

```
NOL1  : 167  PATIFVGRLSWSIDDEWLKKEFEHIGGVIGARVIYERGTDRSRGYGYGVDFENKSYAEKAIQEMQGKEIDGRPINCDMSTS  246
              ::  :::     ::   ::::    :    : :::::  :   ::  ::::::::                :::  :
H.NUC : 485  SKTLVLSNLSYSATEETLQEVFEKATFIKVP....QNQNGKSKGYAFIEFASFEDAKEALNSCNKREIEGRAIRLELQGP  560

NOL1  : 247  KPAGNNDRAKKFGDTPSEPSDTLFLGNLSFNADRDAIFELFAKHGEVVSVRIPTHPETEQPKGFGYVQFSNMEDAKKALD  326
                                   :  :::::::     :  ::   :::       ::  :::::::::: :
H.NUC : 561  RGSPN........ARSQPSKTLFVKGLSEDTTEETLKESF...DGSVRARIVTDRETGSSKGFGFVDFNSEEDAKEAME    628

NOL1  : 327  ALQGEYIDNRPVRLDFSSPRPNND  350
              :::     :  ::  :
H.NUC : 629  ..DGE.IDGNKVTLDWAKPKGE    647

NOL1  : 351  GGRGGSR.GFGGGRGGGRGGNRGFGGRG.GARGGRRGGFRPS.GSGANTAPLGRSRNTASFAGSKKTFD  414
             ::: :: ::  :::::: :::: :::: ::::: :: :::    :
H.NUC : 648  GGFGGRGGRGGFGGRGGGRGGFGGRGGGRGGFRGGRGGGFRGGRGGGGDHKPQGK..........KTKFE  707
```

FIG. 14B

1   MetSerValSerLysIleAlaPheValLeuSerAlaIleAlaSerLeuAlaValAlaAsp   20

21  ThrSerAlaAlaGluThrAlaGluLeuGlnAlaIleIleGlyAspIleAsnSerHisLeu   40

41  SerAspTyrLeuGlyLeuGluThrGlyAsnSerGlyPheGlnIleProSerAspValLeu   60

61  SerValTyrGlnGlnValMetThrTyrThrAspAspAlaTyrThrThrLeuPheSerGlu   80

81  LeuAspPheAspAlaIleThrLysThrIleValLysLeuProTrpTyrThrThrArgLeu   100

101 SerSerGluIleAlaAlaAlaLeuAlaSerValSerProAlaSerSerGluAlaAlaSer   120

121 SerSerGluAlaAlaSerSerSerLysAlaAlaSerSerSerGluAlaThrSerSerAla   140

141 AlaProSerSerSerAlaAlaProSerSerSerAlaAlaProSerSerSerAlaGluSer   160

161 SerSerLysAlaValSerSerSerValAlaProThrThrSerSerValSerThrSerThr   180

181 ValGluThrAlaSerAsnAlaGlyGlnArgValAsnAlaGlyAlaAlaSerPheGlyAla   200

201 ValValAlaGlyAlaAlaAlaLeuLeuLeu 210

*FIG. 17*

1   MetAlaLysThrThrLysValLysGlyAsnLysLysGluValLysAlaSerLysGlnAla   20
21  LysGluGluLysAlaLysAlaValSerSerSerSerSerGluSerSerSerSerSerSer   40
41  SerSerSerGluSerGluSerGluSerGluSerGluSerSerSerSerSerSer   60
61  SerSerAspSerGluSerSerSerSerSerSerAspSerGluSerGluAlaGluThr   80
81  LysLysGluGluSerLysAspSerSerSerSerSerAspSerSerSerAspGluGlu   100
101 GluGluGluGluLysGluGluThrLysLysGluGluSerLysGluSerSerSerSerAsp   120
121 SerSerSerSerSerSerSerAspSerGluSerGluLysGluGluSerAsnAspLysLys   140
141 ArgLysSerGluAspAlaGluGluGluGluAspGluGluSerSerAsnLysLysGlnLys   160
161 AsnGluGluThrGluGluProAlaThrIlePheValGlyArgLeuSerTrpSerIleAsp   180
181 AspGluTrpLeuLysLysGluPheGluHisIleGlyGlyValIleGlyAlaArgValIle   200
201 TyrGluArgGlyThrAspArgSerArgGlyTyrGlyTyrValAspPheGluAsnLysSer   220
221 TyrAlaGluLysAlaIleGlnGluMetGlnGlyLysGluIleAspGlyArgProIleAsn   240
241 CysAspMetSerThrSerLysProAlaGlyAsnAsnAspArgAlaLysLysPheGlyAsp   260
261 ThrProSerGluProSerAspThrLeuPheLeuGlyAsnLeuSerPheAsnAlaAspArg   280
281 AspAlaIlePheGluLeuPheAlaLysHisGlyGluValValSerValArgIleProThr   300
301 HisProGluThrGluGlnProLysGlyPheGlyTyrValGlnPhrSerAsnMetGluAsp   320
321 AlaLysLysAlaLeuAspAlaLeuGlnGlyGluTyrIleAspAsnArgProValArgLeu   340
341 AspPheSerSerProArgProAsnAsnAspGlyGlyArgGlyGlySerArgGlyPheGly   360
361 GlyArgGlyGlyGlyArgGlyGlyAsnArgGlyPheGlyGlyArgGlyGlyAlaArgGly   380
381 GlyArgGlyGlyPheArgProSerGlySerGlyAlaAsnThrAlaProLeuGlyArgSer   400
401 ArgAsnThrAlaSerPheAlaGlySerLysLysThrPheAsp   414

*FIG. 18*

1    GATCTGGTTATGGTTTTTCTTGACTATAACCTTAATTATGAGACTAATGTCTTCGGGAGG 60
61   TCCCTTTTCCGATTTTCCGACTCTTTTCCGTTGAAGAATGTACTTGTGGTTTTGAATCCT 120
121  ACGGCAGTTATTGCGGCGGTTTGGCCCTTTCTTTCAAAGATTGTGATGGAAATAATTGAT 180
181  TGTTCCGGGAAATGTGTCTTATTTTCTAAAAGCATCTTTTTTTCTCTCCAATTCTTCGAG 240
241  CTATTTCCAGTAAAGGAAAAAAAGGTTTGCTGTAAGGGTGAATATGTCTCCAACCTCTT 300
301  TGAGGTACTGCGTTGCTTCATTCACCATTTAATATAAATAGTACATTGGCAGCCCTCTTT 360
361  CAAACGTCAATTATTCTCGCTTGCCTAACTTTGTTCGGACCGAAATTATAAAGGCATTCA 420
421  ATCAGTAACAATAATTGCTATTGCATAACTATACCCTCTGCTAAATAAAATAAAATGTCC 480
481  GTTTCCAAGATTGCTTTCGTTTTAAGTGCCATTGCCTCTTTGGCCGTCGCTGACACCAGC 540
541  GCCGCCGAAACTGCTGAATTGCAAGCTATTATCGGTGACATCAACTCTCATCTTTCTGAC 600
601  TACTTGGGTCTAGAAACTGGCAACAGTGGATTCCAAATTCCATCTGATGTCTTGAGTGTG 660
661  TATCAACAAGTCATGACTTACACCGATGACGCTTACACTACCTTGTTTAGTGAATTGGAC 720
721  TTTGATGCTATCACTAAGACAATTGTTAAATTGCCATGGTACACCACAAGATTGAGTTCT 780
781  GAAATCGCTGCTGCTCTTGCCTCCGTTTCCCCAGCTTCTTCCGAGGCTGCATCTTCTTCC 840
841  GAGGCTGCATCTTCTTCCAAGGCTGCATCTTCTTCCGAAGCTACATCCTCTGCCGCTCCA 900
901  TCCTCTTCTGCTGCCCCATCTTCTTCTGCTGCCCCATCATCATCTGCCGAATCATCTTCT 960
961  AAGGCCGTTTCTTCTTCTGTCGCTCCAACTACCTCTTCTCTCAGCACTTCTACAGTCGAA 1020
1021 ACTGCTTCCAATGCCGGTCAAAGAGTCAATGCAGGCGCTGCCTCTTTCGGTGCTGTTGTT 1080
1081 GCAGGTGCAGCTGCTTTATTGTTATAAAAGGGAACCTTTTACAACAAATATTTGAAAAAT 1140
1141 TACCTCCATTATTATACCTTCTCTTTATGTAATTGTTAGTTCGAAAATTTTTTCTTCATT 1200
1201 AATATAATCAACTTCTAAAACTTTCTAAAAACGTTCTCTTTTTCGAGATTAGTGCTTCTT 1260
1261 CCCAATCCGTAAGAAATGTTTCCTTTCTTGACAATTGGCACCAGCTGGCTACTCGTTGCT 1320
1321 CGAAAACTACTCTCTTTTATTTTTAATTTACGAACGATTATCTTTCGAAGGAACGACCAA 1380
1381 ACGAGCTAAATATGGGCATCGCCAACGTTAAAAAAATGGACCCTACCGAAGACGTTATTA 1440
1441 TGCCAAGGCGCAGCGAAGAGTCTTTCTCCTTGAGAAAAAATATGCATGAAACAAAATAGA 1500
1501 CAGGACCAGACCCTCTTCGGGAAAAAAGTCAAGATTTAACACGTGGCTACACCGGCTGG 1560
1561 CTTACAACCAACCAACATAAGATC 1584

*FIG. 19*

```
  1 GCTAGCTATTTAAACCCCATCACGTTGATTGTCTATTTCGCTATAGGTTATTTTGCCAAG  60
 61 AAAACTTACTGGGCAATACTTACATCCATTCAGATTTTTGGATAAAGCAATTGAAGAAAG 120
121 ACGACAGCAATTCGACTGGTGGTTGTTAATTACCCTTTGATCCTCTGATTTAAAGACGTA 180
181 ATCCTTCCTGGGGGTAAGTGCCTGATGTATGGGTCCCCATGCCCTTTTTTTTCGTTTCTT 240
241 TTTTCACTCCATTTCTTTTTTTTTTTTTTTTGGTGAAAAATTTGCAAGGGCAGCTCA 300
301 TCGCAAGAACGAAAATTTTCAATCCAATATTAAAAGTACTTAAGTGTAGCTGTTGCTGTC 360
361 TGCACTTCCCAATCCATTGGTACCTTAAGTTATTTCCTTTCGTAGTATTTTTCTTACTTT 420
421 TGCTTCCCAAAGACGAACTGTTAACCAATTTCGGATCACTCAACCCAGGCAGGATAAAAT 480
481 AAGATGGCTAAGACTACTAAAGTAAAAGGTAACAAGAAGGAAGTTAAGGCTTCCAAACAA 540
541 GCCAAAGAAGAAAAAGCTAAGGCCGTCTCTTCCTCTTCCTCCGAATCTTCATCCTCATCT 600
601 TCATCTTCATCTGAATCTGAATCTGAGTCTGAGTCTGAATCTGAATCTTCATCTTCATCT 660
661 TCATCCTCTGATTCTGAATCCTCTTCTTCATCGTCTTCTGACAGCGAAAGTGAAGCTGAA 720
721 ACCAAGAAGGAAGAATCCAAGGATTCCTCTTCCTCTTCCTCTGACTCTTCTTCCGACGAA 780
781 GAAGAAGAAGAAAAAGAAGAAACCAAGAAGGAAGAATCAAAAGAATCTTCTAGCTCT 840
841 GATTCATCCTCATCTTCATCTTCTGATAGCGAAAGCGAAAAGGAAGAGTCTAACGATAAG 900
901 AAACGTAAATCTGAGGACGCCGAAGAAGAAGAAGACGAAGAGTCTTCCAACAAGAAGCAA 960
961 AAAAATGAAGAAACCGAAGAACCAGCTACTATTTTCGTTGGTAGACTATCGTGGTCTATT 1020
1021 GATGACGAATGGTTGAAGAAGGAATTCGAACACATCGGTGGTGTCATTGGTGCCAGAGTT 1080
1081 ATTTATGAAAGAGGTACCGATAGATCTCGTGGTTATGGTTACGTTGATTTTGAAAACAAA 1140
1141 TCTTATGCTGAAAAGGCCATTCAAGAAATGCAAGGTAAGGAAATTGATGGTAGACCAATC 1200
1201 AACTGTGATATGTCCACAAGCAAGCCAGCTGGTAACAACGATCGTGCCAAGAAATTCGGT 1260
1261 GATACCCCATCTGAACCATCTGACACTTTGTTCTTGGGTAACTTATCTTTCAATGCTGAC 1320
1321 AGAGACGCTATTTTCGAATTATTCGCTAAACACGGTGAAGTTGTTTCCGTCCGTATCCCA 1380
1381 ACACATCCAGAAACTGAACAACCAAAAGGTTTCGGTTATGTTCAATTCTCCAACATGGAG 1440
1441 GACGCCAAGAAGGCTCTAGACGCTTTACAAGGTGAATACATTGACAACAGACCAGTTAGA 1500
1501 TTAGACTTCTCTTCTCCAAGACCAAACAACGATGGTGGTCGTGGCGGTAGCCGTGGTTTT 1560
1561 GGTGGTCGTGGCGGTGGTCGTGGCGGTAACCGTGGATTCGGTGGTCGTGGTGGCGCTCGC 1620
```

FIG. 20

1621 GGTGGCCGTGGCGGTTTCAGACCATCTGGTTCTGGTGCTAATACTGCTCCATTGGGCAGA 1680

1681 TCAAGAAATACCGCTTCTTTCGCTGGTTCAAAGAAAACATTTGATTAATGAGAAAATGAA 1740

1741 ATGAATTTCAATTTCAATTTTTTCTCTTTTTACGTTAATTACTATATTCCATTTTTGAGG 1800

1801 AAAAATTTGGTCTATAATATTTTGTGTACATTAGTAAGTAAATAGGATACATTCTTAAAC 1860

1861 CTTTCATTCACCATCTCTATTTGCCAACTTTTCTTCGAATGGCTTACTCTTTTTTTTTTC 1920

1921 ACGATGAGATGAGATCGCTAGATACGGAAGATTACAAGGCCTTGGAAAATACTCAAAAAA 1980

1981 TTTCAGTAATATGAAATGAATATCTAAATAAAAGCTT 2017

FIG. 20 (CONT'D.)

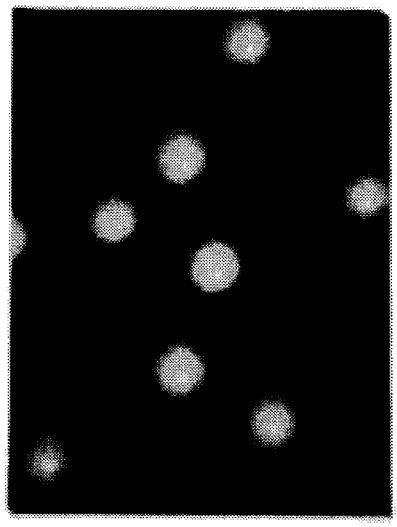
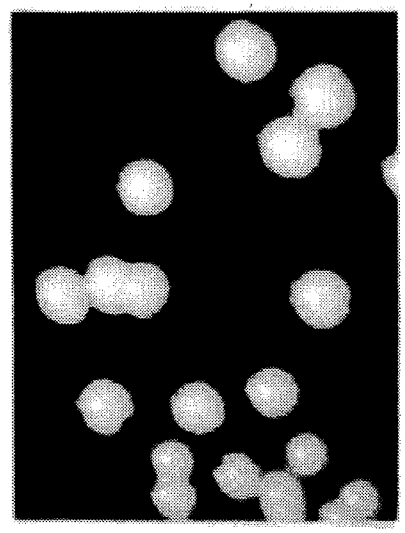
FIG. 23A    FIG. 23B
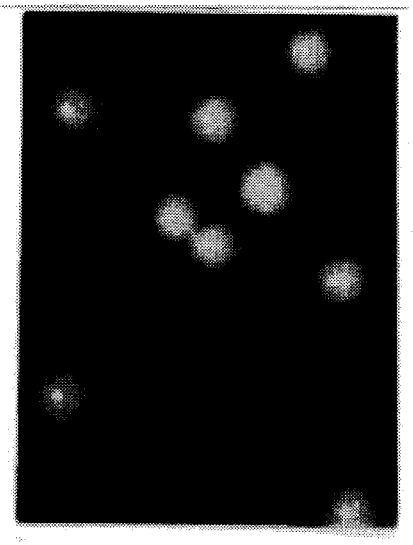
FIG. 23C    FIG. 23D 20μm

STRESS-INDUCED PROTEINS, GENES CODING THEREFOR, TRANSFORMED CELLS OF ORGANISMS, METHODS AND APPLICATIONS

TECHNICAL FIELD

This invention relates generally to the field of biotechnology. More specifically, it relates to families of valuable proteins and genes coding therefor in eucaryotes. The invention relates to the gene-carrying hosts which are adaptable to grow under conditions outside their normal, optimum physiological growth conditions and are capable of over-expressing functional proteins.

BACKGROUND OF THE INVENTION

There are numerous industrial applications where it is highly desirable for microorganisms to multiply and/or to synthesize and excrete products, such as proteins, under conditions outside but not lethal, the normal conditions for optimum vegetative growth.

When a wide variety of organisms are exposed to different types of stress, synthesis of specific proteins are induced. Such types of stress include elevated temperature, cold-shock, ethanol, heavy metal ions, anoxia, glucose starvation and others. DNA-damaging agents like nalidixic acid, UV irradiation, and bacteriophage infection have been shown to induce all or part of the heat-shock response. Concurrently with the induction of, for instance, these heat-shock proteins, microorganism cells become more tolerant to high temperature exposure normally lethal to the microorganism.

When certain microorganisms, procaryotes like *Escherichia coli*, are exposed to a sudden increase in ambient temperature, a shift occurs from the synthesis of normal cellular proteins to the synthesis of what are called "heat-shock" proteins. The synthesis of these proteins after incubation at elevated but non-lethal temperature is correlated with the induction of thermo-tolerance, which is the enhanced ability of the microorganism to withstand subsequent high temperature which is normally a lethal high temperature.

Cold-induced genes and expressed proteins have been reported in *E. coli*, which have been termed cold-shock induced. Induction of the synthesis of several proteins in response to cold-shock (from 37° C. to 10° C.) has been reported in *E. coli* (Jones et al., 1987). A gene coding one of these cold-shock proteins was cloned and sequenced (Goldstein et al., 1990).

Heat-shock response in *E. coli* has also been described (Neidhardt et al., 1984). When cell cultures are transferred from 30° C. to 42° C. heat-shock proteins are transiently expressed. The induction has been shown to be accomplished primarily by an alternate σ-subunit of RNA polymerase ($\sigma^{32}$), encoded by rpoH (htpK) which recognizes specific heat-shock promoters (Grossman et al., 1987; Strauss et al., 1987). It has also been shown that *E. coli* responds to cold temperature. However, when growing cell cultures were transferred from 37° C. to 10° C., several peptides were induced, none of which were heat-shock protein. Certain proteins are induced by both cold- and heat-shock. A developmentally regulated membrane protein (Maniak and Nellen, 1988) and ubiquitin (Müller-Taubenberger et al., 1988) of *Dictyostelium discoidum* were shown to be induced in response to cold- and heat-shock.

This invention contributes to clarification of the scientific phenomena involved in stress-induced e.g., cold- and/or heat-induced proteins, which is of major scientific significance. Further, the stress-induced, for instance heat- and/or cold-shock proteins, can have numerous commercial applications. Such applications include the ability of growing selected cells (e.g., of microorganism) under conditions under which the cells normally would not grow, or not grow as well. This invention discloses and suggests several important industrial applications.

Yeast organisms are well suited for commercial expression of heterologous proteins, having advantages over tissue culture and bacteria. First of all, highly developed technology exists for yeast fermentation processes. Yeast can be employed safely since handling and disposal methods are well established. In addition, yeast is an eucaryotic organism which has advantages when expressing genes originating from other eucaryotic backgrounds. Most of all, yeast is very well characterized and can be manipulated genetically to maximize expression of heterologous peptides.

The ideal expression system for yeast as a microbial "factory" would allow for enhanced protein production, controlled during portions of the fermentation process. Products are currently made utilizing multi-copy plasmids, efficient promoters and amplified genes. However, these systems still lack the ideal parameter, which involves the ability to direct product synthesis at a specific time or growth conditions during the fermentation. By separating the growth process (which may involve days of culture incubation) from that of product synthesis (which may occur within hours), one can obtain higher levels of product. The product is exposed for less time in the media or within cells where it may be susceptible to proteolytic degradation, and any detrimental effect of the product on the growth of the organism is removed by largely separating the growth and production processes.

In accordance with the invention, conditions have been identified under which yeast synthesizes certain desirable proteins in high yield. These conditions relate principally to the stage of growth of the yeast and the temperature, which is outside of the normal physiologically ideal temperature conditions for vegetative growth. In accordance with the invention, genes are induced in selected microorganisms (as will be described hereinafter), preferably yeasts. Microorganisms like eucaryotes and procaryotes transformed with genes of the invention are suitable for growth at low temperatures and/or at high temperatures and produce products, like proteins which normally are not produced at all or in yields not commercially interesting.

Another interesting area is the production of functional proteins when produced by recombinant DNA or fermentation techniques. It is known that proteins are often enzymatically degraded or folded improperly at physiological temperatures resulting in the proteins' decreased physiological activity. The invention provides the possibility of growing transformed cells at temperatures at which the products would retain physiological activity. For instance, an advantage of production of the proteins at reduced temperature would be to minimize improper folding or degradation.

Thus, in accordance with one embodiment of the invention, a host cell transformed with one or more genes (or part thereof) of the invention can express a functional protein of commercial value which will be produced though the ambient temperature has been reduced or raised outside the normal optimum growth temperature. This will allow the expression of the target protein to proceed with no adverse effects on the desired physiological activity of the protein. Transformed host cells and/or the protein products can also be useful in the field of agriculture in protecting plants against frost or heat damage; for production of food products, and any other biological (or pharmaceutical) products that should be protected from a stress-creating situation like extreme temperatures.

An important practical application of the invention is the mass growing of transformed cells (e.g., eucaryotes like yeasts) at lower than normal growth optimum temperature, thus achieving substantial savings in energy, or growing the cells at higher than (or at normal) optimum growth temperatures while producing more rapidly and/or higher yield of the product desired.

Further, the transfected microorganism can be made to have higher resistance to the growth inhibitory effect of the environmental stress (e.g., alcohol) and thus grow for longer periods of time and/or produce higher yields of the desired product. There are several other practical applications described herein and others will become apparent from the teachings of the invention.

Publications that may be of interest to one skilled in the art, are listed at the end of this document.

SUMMARY OF THE INVENTION

The invention broadly described provides a family of stress-inducible genes and portions thereof. The expression of these genes is inducible by any one of several types of stress, namely, heat-shock and/or cold-shock. The invention also provides new and useful proteins over-expressed by eucaryotes or other suitable, competent cells like procaryotes transformed by appropriate cloning vehicles. Proteins are disclosed which contribute to and/or confer thermo-tolerance and/or contribute to or confer protection against freezing. Presently preferred transfected eucaryotes are thermo-stable and/or cold-stable yeast strains. Cold-shock and heat-shock stress is disclosed herein to induce the over-expression of a family of proteins, typified by a temperature-inducible protein (TIP1) and a nucleolin-like protein NOL1). The nucleotide sequences of the genes and of the proteins are provided (shown in the Sequence Listing as SEQ ID NO:1 through SEQ ID NO:4). Yeast cells deficient in the TIP1 gene and NOL1 gene are described.

The invention provides a cold- and heat-shock induced gene which encodes a cold-shock and heat-shock inducible 1.0-kb mRNA transcript and a cold-shock induced gene which encodes a cold-shock inducible 1.6-kb mRNA transcript. The invention provides also a gene family of yeast which hybridizes under conditions described below, with TIP1 or with NOL1, which genes are capable of encoding a protein which contributes to or confers thermo-tolerance to an appropriate organism. A new property and use of the protein SRP1 is described. Proteins of the invention are also suggested for industrial applications where protection against freezing temperatures or elevated temperatures is desired, i.e., temperatures normally outside of the normal physiological range.

The invention further describes certain DNA fragments that are capable of encoding the proteins encoded by the, TIP1 and NOL1 genes, respectively. Also, the invention describes DNA fragments that are capable of encoding proteins equivalent functionally (as defined hereinafter) to the proteins encoded by the TIP1 and NOL1 genes, respectively. The invention further describes several recombinant replicable expression vehicles which incorporate the endogenous promoter to drive the expression of foreign proteins, i.e., other than those encoded by the TIP1 ( cold- and heat-induced) and NOL1 ( cold-induced ) genes. The invention describes replicable expression vehicles which incorporate a heterologous promoter to drive the expression of the proteins which are encoded by TIP1 or NOL1, or functionally equivalent proteins. The invention describes replicable expression vectors which incorporate the endogenous promoter for the TIP1 (cold- and heat-induced) or NOL1 (cold-induced) gene and also a heterologous promoter (preferably a very strong promoter) to drive the expression of appropriate DNA encoding sequences of the proteins encoded by the TIP1 and the NOL1 gene, respectively and selected foreign proteins.

The invention further describes competent thermo-tolerant organisms, transfected eucaryotes and transformed procaryotes, which are capable of expressing (preferably constitutively and in high yields) the proteins encoded by TIP1 or NOL1, respectively, or their functionally equivalent proteins, and/or a selected target protein. These and other aspects of the invention are described in greater details hereinafter.

From this description, it will become apparent that the invention opens exciting and important new opportunities, and scientific perspectives and industrial applications in the field of life and related sciences. Just to mention two, it will provide fermentations at lower or higher than conventional growth temperatures with transformed yeasts (with TIP1); it will provide the expression of valuable proteins, e.g., physiologically (biologically) active proteins, at temperatures lower than conventional temperatures which can be detrimental to the full physiological activity.

DEPOSIT OF BIOLOGICAL MATERIALS

*E. coli* strain KE1 containing plasmid pDCS31 containing the TIP1 gene is deposited with the ATCC (Bethesda, Md.) under Accession No. 68535. *Saccharomyces cerevisiae* strain KY1 containing plasmid pYCA1 containing the TIP1 gene is deposited with the ATCC under Accession No. 74036. *E. coli* strain KE2 containing pDCS52 containing the NOL1 gene and long 3'-flanking region is deposited with the ATCC under Accession No. 68536, and *E. coli* strain KE3 containing pDCS84 containing the NOL1 gene and long 5'-flanking region was deposited with the ATCC under Accession No. 68534.

BRIEF DESCRIPTION OF THE DRAWINGS

The accompanying drawings illustrate preferred embodiments of the invention.

FIG. 4 shows the nucleotide and deduced amino acid sequence of TIP1 gene (shown in the Sequence Listing as SEQ ID NO:1 and SEQ ID NO:2).

FIG. 9 shows sequence comparison of TIP1 and SRP1 (SEQ ID NOS:2 and 6).

Figure 11:
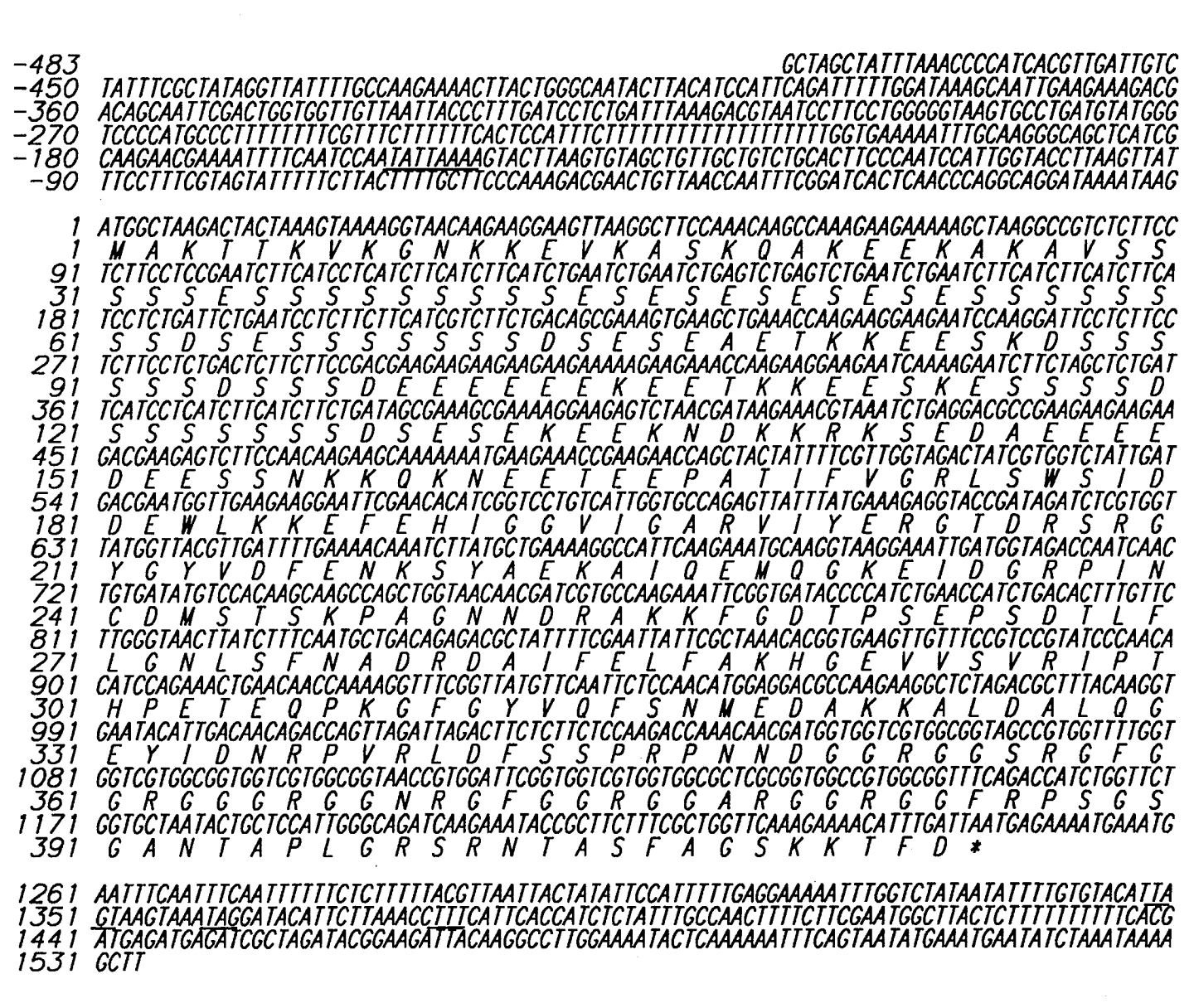

FIG. 11 shows the nucleotide and deduced amino acid sequence of NOL1 (shown in the Sequence Listing as SEQ ID NO:3 and SEQ ID NO:4).

FIG. 14 (A and B) shows a sequence comparison of NOL1 and other proteins (SEQ ID NOS:7–10).

FIG. 17 shows the amino acid sequence (1-210) (SEQ ID NO:2) of the TIP1 protein.

FIG. 18 shows the amino acid sequence (1-414) (SEQ ID NO:4) of the NOL1 protein.

FIG. 19 shows a nucleotide sequence (1-1584) (SEQ ID NO:1) containing the TIP1 gene.

FIG. 20 shows a nucleotide sequence (1-2017) (SEQ ID NO:3) containing the NOL1 gene.

FIG. 23 shows yeast colonies of tip1⁻ mutant and wild cells.

DETAILED DESCRIPTION OF THE INVENTION AND OF THE PREFERRED EMBODIMENTS

Figure 1A:
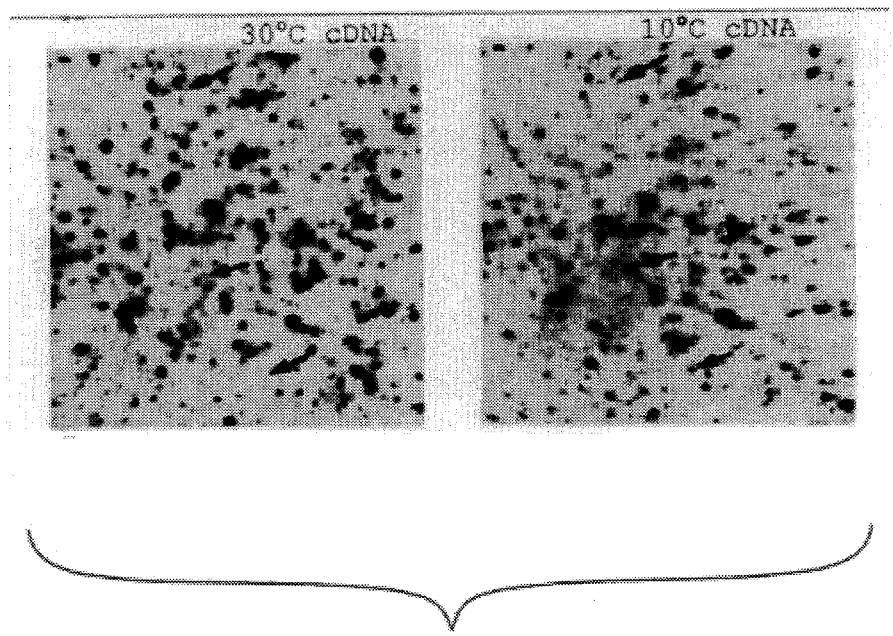
FIG. 1 (A and B ) shows screening by differential colony hybridization.

In accordance with the invention, a family of genes has been discovered which has been induced at temperatures above and/or below normal physiological temperatures for the growth of the cells of microorganisms. These temperatures are designated as "extreme temperatures". The preferred microorganism at the present time is an eucaryote, ideally a Saccharomyces like *S. cerevisiae*. Other host microorganisms may be suitable for induction of genes of the invention. Suitable competent host cells may be transfected with one or more genes of the invention, as will be described in further details hereinafter.

In this invention, several genes were induced or repressed in response to a shift in temperature below the normal growth temperature of the microorganisms. Likewise, several genes were induced or repressed in response to shift in temperature above the normal growth temperature of the microorganisms. These shifts in temperature are by convention designated as "cold-shock" and "heat-shock", respectively. Of the family of genes of the invention, a select number described further herein are of special interest.

It is to be noted that it is within the contemplation of the invention that the genes be induced by stress conditions generally, as will be discussed in greater detail later. Heat and/or cold are only an illustrative stress means for induction of the genes and over-expression of the proteins or other products.

Plasmids containing yeast genomic DNA whose expression levels were increased by cold-shock are identified and classified into two groups (Group A and B ). Genes whose expression is induced at low temperature, and surprisingly also at high temperature were identified in *Saccharomyces cerevisiae*. They are identified as "temperature-inducible proteins"; one is identified as TIP1. Plasmid DNA fragment of TIP1 hybridizes to a 1.0-kb transcript from yeast cold-shock cells (in Northern blot analysis). Another gene identified here as NOL1, also is inducible by cold-shock. Plasmid DNA fragment of NOL1 hybridizes to a 1.6-kb transcript from yeast cold-shock cells (in Northern blot analysis). The two genes (TIP1 and NOL1) which are described in greater detail herein, appear to be members of a multigene family. Those members of the gene family of yeast that have such homology as to hybridize (under conditions further described below) with the TIP1 and NOL1 genes, respectively and which encode a protein which confers or at least contributes to confer thermo-stability and/or cold-stability to a selected transformed organism (like yeast), are within the scope of the invention.

The invention includes the nucleotide sequence of the genes which hybridize with TIP1 and also those genes which hybridize with NOL1, as well as part of the genes, e.g., the open-reading frame (ORF) thereof (shown in the Sequence Listing as SEQ ID MO:1 and SEQ ID NO:3). Also included in this invention as described in further detail, are proteins which are over-expressed by organisms which have been transformed with appropriate expression vectors. These vectors contain DNA sequences coding for the desired protein under the control of a highly active yeast (or other) promoter heterologous (foreign) or homologous (native) promoter.

The over-expressed proteins of these genes are considered to provide stress tolerance, e.g., low and/or high temperature resistance to the transformed microorganism.

Plasmids containing DNA which hybridizes to the 1.0-kb transcript are designated herein as "TIP1-encoding plasmids". Likewise, the plasmids containing DNA which hybridizes to the 1.6-kb transcript are designed as "NOL1-encoding plasmids".

The TIP1 protein, when over-expressed, may contribute to or confer thermo-tolerance directly to transformed cells; it plays a significant and valuable role in protecting the cells from the effect of high temperatures which normally are not optimum for the growth of the cells including from the lethal effect of high temperatures, i.e., at temperatures which are normally lethal growth of the cells.

A like effect is determinable for proteins expressed by the other genes related to TIP1 or NOL1.

The term "thermo-tolerance" or "thermo-resistance" here means the property of the cells to remain viable at high temperatures at which they would normally not remain viable. The term "viable" does not necessarily mean growing or multiplying cells, it also means that protein synthesis may be going on and yet the growth of the cells or cell division be at a minimum or reduced rate or arrested.

"Tolerance" or "resistance" at low temperature means the property of the cells to remain viable at low temperature at which the growth rate of the organism is normally decreased or arrested. In this connection "viable" also means that protein synthesis may still proceed in an organism transformed in accordance with the invention though cell division and/or growth may be slowed down or arrested. "Tolerance" or "resistance" at temperature outside the normal physiological growth temperature refers when appropriate tolerance at low temperature and thermo-tolerance.

The genes of the invention, typically TIP1 express proteins which are different from the heat-shock class of proteins referred to as chaperonins, which have been shown to consist of helper proteins in chain folding and assembly phenomena within cells (Schlesinger 1990, Pelham 1989). As described herein, the over-expression of TIP1 (or the other genes related to TIP1) contributes or confers thermotolerance directly to the cells, which is yet another distinction from chaperonins which confer heat-resistance to the cells by preventing proteins from unfolding.

The characterization of the TIP1 protein, discussed further below, shows that although it is also rich in serine like the known serine-rich, glucose-inducible protein SRP1, Marquet et al., *J. Mol. Biol.*, (1988), 202, 455–470, there are distinct differences discussed herein.

An aspect of the invention is the discovery that the gene encoding SRP1 is cold-shock inducible. It has been shown that a nol1⁻ mutant shows lag-time when the temperature is shifted from 30° to 10° C., and grows slower than the wild-type at 30° C. Accordingly, over-expression of NOL1 is expected to increase growth rate at 30° C. and even to a higher extent at lower temperatures such as at 20° C., 15° C. and 10° C.

It can therefore be expected that the NOL1 does indeed contribute to low temperature tolerance. Thus, it may be used for the various applications for which cold-inducible genes (and proteins) are useful including the property of conferring low temperature resistance to a host cell, an eucaryotic microorganism, like yeast.

The characterization of the NOL1 protein as discussed further below, shows that although it has certain homology with mammalian nucleolin NOL1, is distinctly different from these proteins.

As is apparent from the description that follows, the genes of the invention and the proteins thereof are a unique and useful family. Cloning of Genes for Cold-Shock Proteins.

The invention uses principles and methodology of recombinant DNA technology. Periodically herein, reference will be made to certain known principles, strategies or practices (methodology) to assist the reader of this description.

A culture of yeast *S. cerevisiae* in the exponential growth stage is maintained at 30° C.; the temperature is dropped from 30° C. to 10° C. The exponential growth rate (measured as doubling time) was reduced from 1.9 hours at 30° C. to 14 hours at 10° C. in YPD medium. No lag period was observed (which differentiates this growth pattern from that of *E. coli* which does show a lag period). By two-dimensional gel electrophoresis analysis, several protein spots were identified to be increased or decreased 2 hours after shifting the temperature from 30° C. to 10° C.

Since these spots were not major, differential hybridization screening was performed in order to directly clone these genes. To facilitate the isolation of differentially expressed sequences, a genomic DNA library containing small size inserts of approximately 3-kb was constructed to avoid cloning two neighboring genes at the same time. Every transcript has been shown to be localized every 2 to 3-kb on the yeast genome (Hereford and Rosbash, 1977). Approximately 54,000 clones were screened with labeled cDNA probes that are prepared from poly(A)⁺ mRNA of cells cultured at 30° C. or from cold-shocked cells. On the basis of two-dimensional gel electrophoresis analysis, cells cultured at 10° C. for 2 hours after the temperature shift were used as a source of mRNA of cold-shocked cells. The number of colonies examined is more than two times as many as what is necessary to clone a single copy of every gene on the haploid yeast genome with 99% probability when the mean size of inserts is 3-kb (e.g., 2 times→46,000).

Figure 1B:
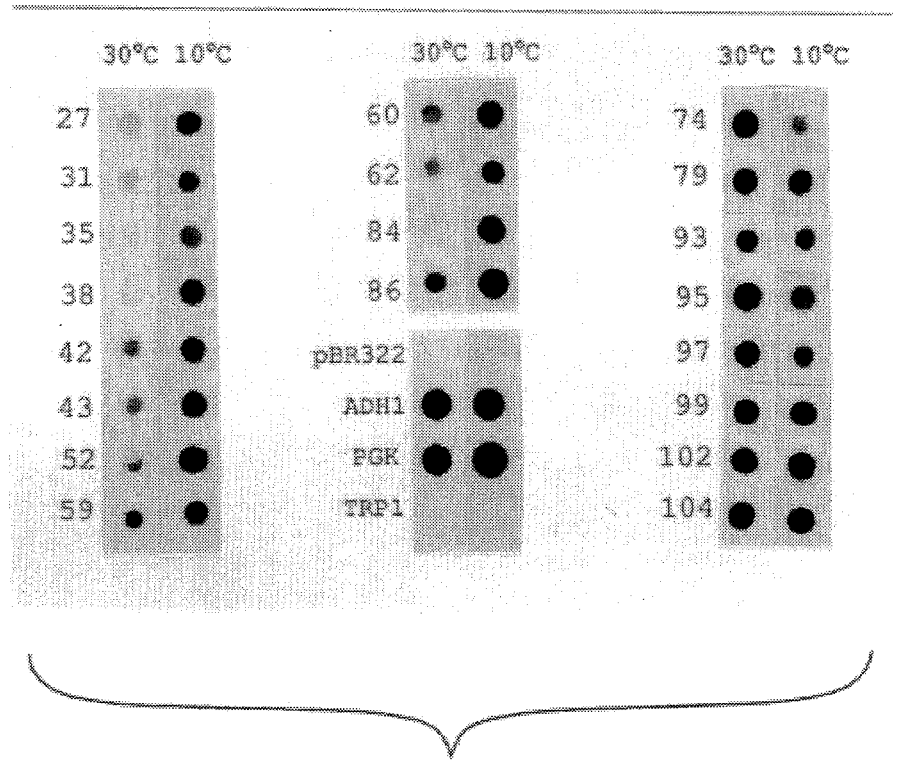

From the initial screening, more than 50 colonies were identified that have stronger hybridization signals at low temperature than they did at 30° C. when probed with cDNA prepared as described above (FIG. 1A). During these screenings, some hybridization signals were prominent on the filters probed with cDNA prepared from cells cultured at 30° C. but much weaker with cDNA prepared from cold-shocked cells. After re-screening, a total of 20 clones which gave the clearest differential response (between the two temperatures) were further analyzed by dot blot hybridization analysis as shown in FIG. 1B; 12 clones (27, 31, 35, 38, 42, 43, 52, 59, 60, 62, 84, and 86 in FIG. 1B) gave stronger signals with the cold-shock cDNA than with the 30° C. cDNA. The remaining eight clones (74, 79, 93, 95, 97, 99, 102, and 104 in FIG. 1B) gave weaker signals with the cold-shock cDNA than with the 30° C. cDNA. The 20 colonies thus contain DNA which represents entire genes or parts thereof whose expression is altered, that is, induced or repressed at low temperature.

Plasmid containing yeast PGK gene, ADH1 gene, or TRP1 gene gave equal signals with both cDNA probes (FIG. 1B).

To further characterize the twelve clones obtained as cold-shock inducible genes, restriction enzyme digestion analysis and Northern analysis were performed. By comparing patterns of ³²P-labeled restriction fragments generated by digestion with HinfI, the cold-shock clones were classified into 5 groups, two of which are further described below.

Plasmids 31, 35, and 38 identified as Group A, hybridized to a 1.0-kb transcript from cold-shocked cells in Northern blot analysis. Plasmids 52 and 84 identified as Group B, hybridized to a 1.6-kb transcript from cold-shocked cells. Expression of Cold-Shock Genes of Group A (TIP1).

Figure 2:
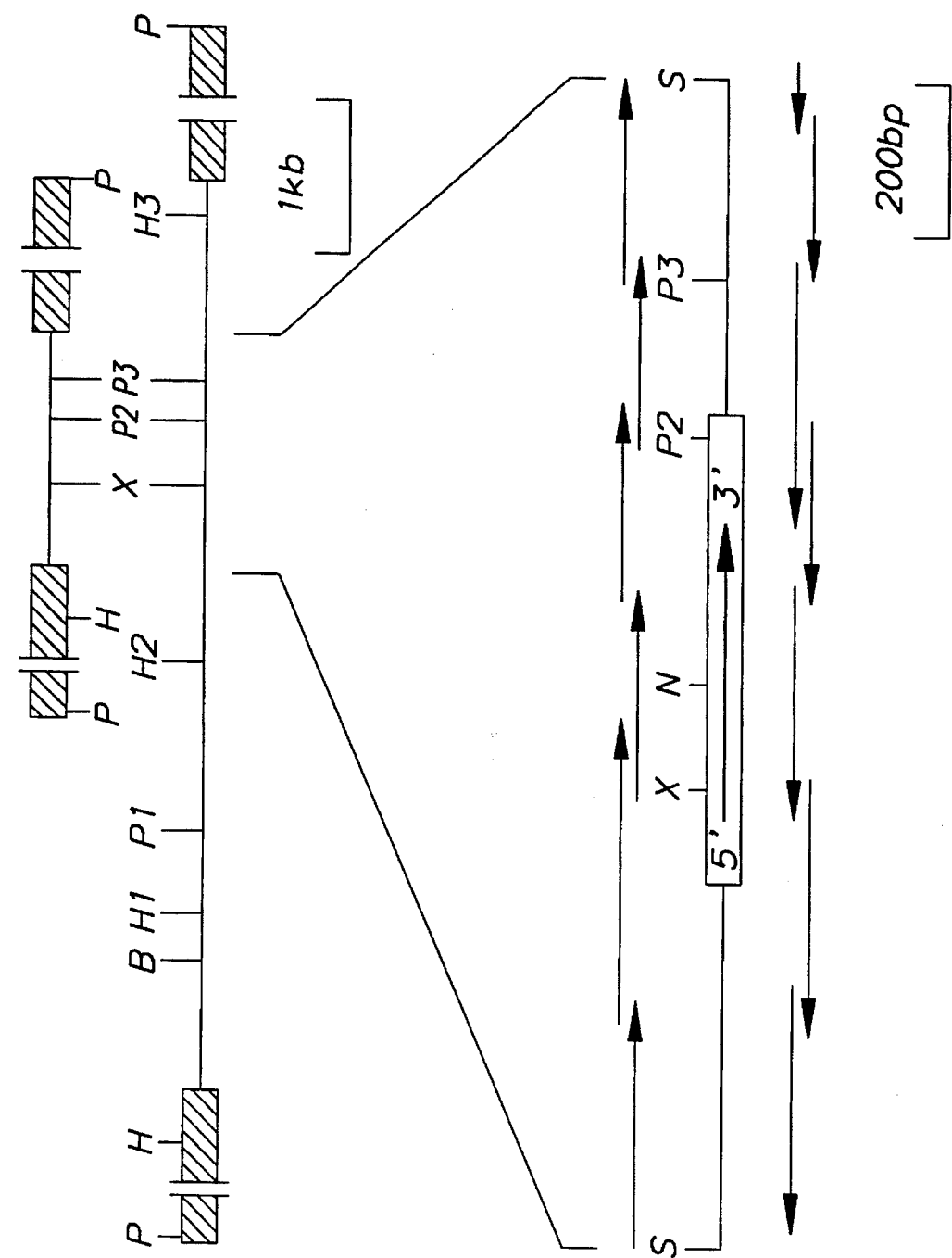
FIG. 2 shows restriction maps and sequencing strategy for TIP1.

In accordance with the invention, Group A plasmids were further characterized. Restriction maps were constructed for the Group A plasmids, pDCS31, pDS35, and pDS38. As shown in FIG. 2, pDCS35 and pDCS38 were identical and pDCS31 contained a 6.3-kb fragment which included the 1.6-kb fragment cloned in pDCS35 and pDCS38. A series of Northern blot experiments were performed using total RNA prepared from cells subjected to various conditions of temperature shock. The 0.4-kb XbaI-PvuII (X-P2 in FIG. 2) fragment was able to hybridize with the 1.0-kb cold-shock transcript. Same results were obtained when the entire plasmids were used as probes.

Figure 3A:
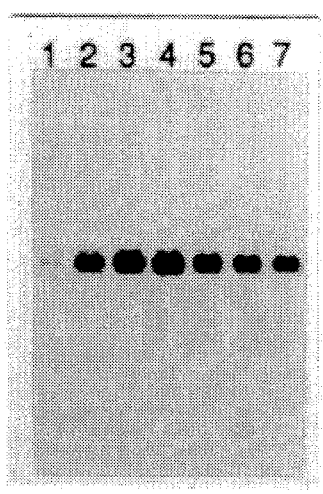
FIG. 3 (A, B, C, D and E) shows regulation of expression of TIP1.

Northern blot analysis with the fragment as a probe is shown in FIG. 3A, where the production of the 1.0-kb transcript dramatically increased after the temperature shift from 30° to 10° C. The highest level of the transcript is observed between 2 and 4 hours after the temperature shift.

The expression levels of yeast heat-shock genes has been found to vary as the cells grow from the log phase to the stationary phase (Werner-Washburne et al., 1989; Nicolet et al., 1989).

Figure 3B:
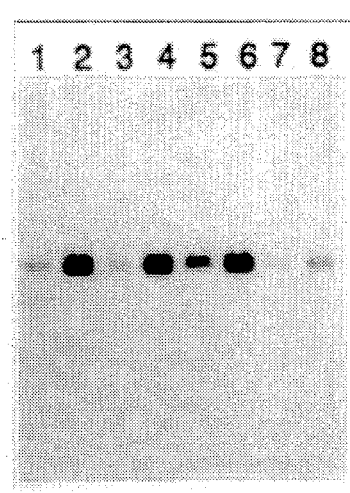

To make these determinations as to whether the cold-shock gene was expressed differentially during growth from log to stationary phase at 30° C., RNA prepared from cells with or without of 2 hours of cold-shock at various growth phases was analyzed (FIG. 3B).

It has been determined that the 1.0-kb transcript encoded by the gene was expressed during the log phase at a low level (FIG. 3B, lanes 1 and 3) at 30° C.; when the cells reached the stationary phase, the amount of transcript increased significantly (lane 5). However, the amount of transcript is less at that stage than when cold-induced (lanes 5 and 6). The amount of the transcript decreased again to a low level when cells were kept in stationary phase for 14 hours (lane 7). Cold-shock induction of the transcript was Observed when cells were in log phase (lanes 2 and 4) or early stationary phase (lane 6).

Mid-log phase is defined as the growth phase in YPD medium at 30° C. where the cell density reaches from $2 \times 10^7$ to $4 \times 10^7$ (cells /ml); early stationary means $1.3 \times 10^8$ (cells/ml) and late stationary means $2.2 \times 10^8$ (cells/ml), based on an $OD_{600}=1~1 \times 10^7$ cells/ml.

Thus, a typical 1.0-kb transcript of the invention is expressed in highest yield upon cold-shock while the cells are in the log or early stationary phase. Level of Expression of the 1.0-kb Transcript Under Various Temperature-Shift Conditions.

Figure 3C:
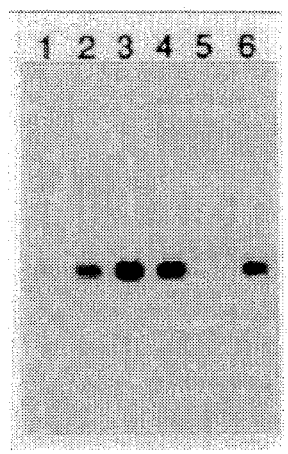
Figure 3D:
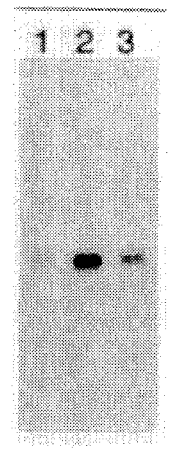
Figure 3E:
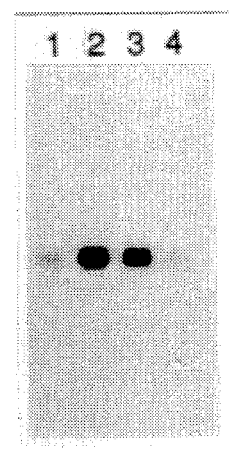

Surprisingly, it was found that the 1.0-kb transcript level also increased not only by temperature-shift from 30° C. to lower temperature: 5° C. (lane 2), 10° C. (lane 3), and 15° C. (lane 4) in FIG. 3C, but also by heat-shock from 30° C. to 39° C. (lane 6 in FIG. 3C). The highest level of induction was observed by shifting the temperature from 30° C. to 10° C. (lane 3, FIG. 3C), or from 37° C. to 10° C. (lane 2, FIG. 3E) or 15° C. (lane 3, FIG. 3E). The gene induction was not detected when cultures were shifted downward to 21° C. either from 30° C. (lane 5, FIG. 3C) or 37° C. (lane 4, FIG. 3E). On the other hand, the amount of the 1.0-kb transcript remained low in cultures grown at 21° C. (lane 1, FIG. 3D), 30° C. (lane 1, FIG. 3C), or 37° C. (lane 1, FIG. 3E).

These results indicate that the induction of the 1.0-kb transcript is regulated not only by the temperature difference for shock but also the temperature used for shock. The highest level of expression appears to occur by a drop from a relative high temperature (37° C.) to the lower temperature (15° C.). Furthermore, the results indicate that the expression of the 1.0-kb transcript is induced by heat-shock as well as by cold-shock. Thus, the gene for the 1.0-kb transcript was designated TIP1 for temperature-inducible protein.
DNA Sequence of TIP1.

Before carrying out DNA sequencing, the approximate location of the TIP1 gene on the plasmid DNA was determined by Southern blot hybridization with cDNA prepared from cold-shocked cells as a probe, as described below. This analysis revealed that TIP1 is located between XbaI and PvuII ($P_3$ in FIG. 2). Subsequently the DNA sequence of the 1584-bp (SEQ ID NO:1) Sau3AI (S-S in FIG. 2) fragment containing the TIP1 gene was determined (FIG. 4).

Within this sequence, one long open-reading frame (ORF) of 630-bp was found capable of encoding a 210-amino acid protein (SEQ ID NO:2), the TIP1 protein. The nucleotide sequence (AATAAA ATG TCC)(-6 to +6 of FIG. 4) surrounding the putative translation initiation site ATG has only one mismatch to the consensus sequence of highly expressed genes in yeast (Hamilton et al., 1987). This confirms the location of the start codon.

Figure 5:
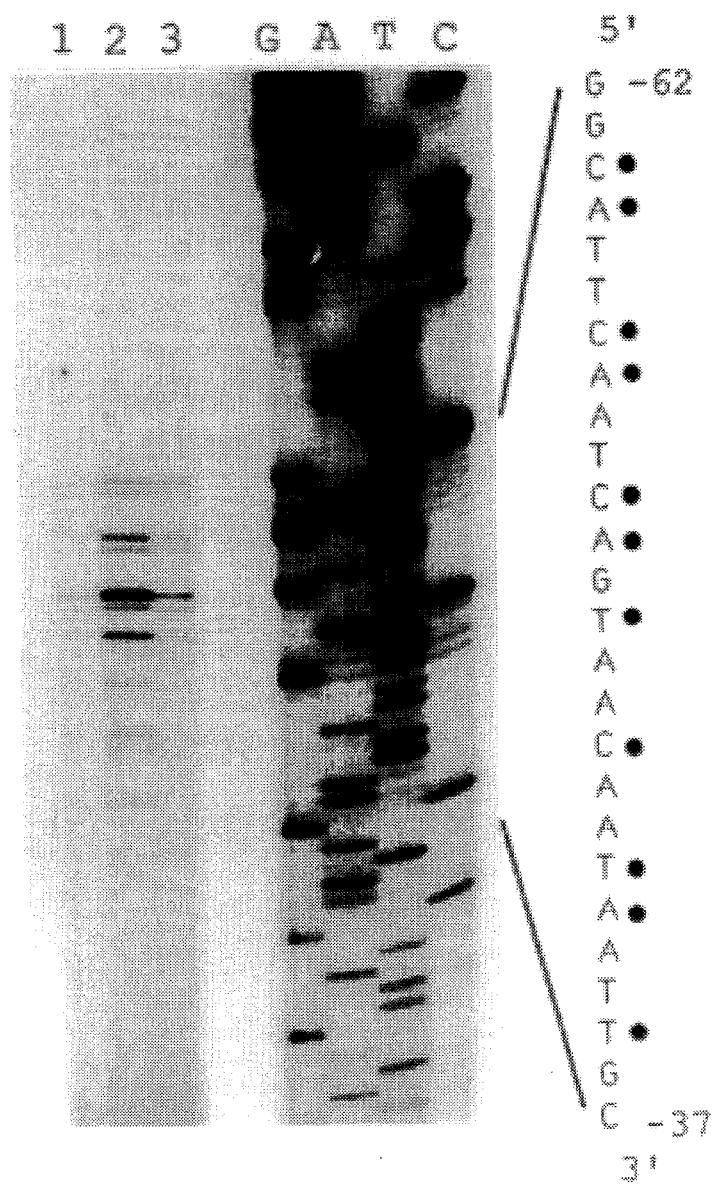
FIG. 5 shows primer extension analysis of the TIP1 mRNA.

Primer extension analysis was carried out in order to identify the transcription start sites (FIG. 5). When the RNA prepared from cold-shocked cells was used as template, 2 major and 9 minor start sites were identified between position −60 to −39 relative to ATG. Some of these extension products were obtained by using RNA prepared from heat-shocked cells. The start site at position −52 was used for both cold-shocked and heat-shocked cells as major start site. The same site was also used for cells grown at 30° C. There are two possible TATA boxes at positions −68 and −142 in the 5' untranslated region (FIG. 4). Since the distance between TATA box and transcription initiation site varies among yeast genes from 40 to 120-bp (Struhl, 1989), the TATA box located from residue −142 to −137 is thus likely to be a promoter element important for TIP1 expression.

The sequence for the promoter element(s) is located upstream in a 1,000 nucleotide sequence, upstream of the 5' untranslated region (SEQ ID NO:5). Since it is known that all yeast promoters contain three basic kinds of DNA sequence regulatory elements, upstream activation sequence (UAS) element, TATA element and an initiation element, depending on the gene, UAS element(s) can be located anywhere from 100 to 1,500-bp upstream of the initiation site. It is not excluded, however, that regulatory elements for TIP1 (or genes homologous to TIP1) be positioned further upstream in the sequence of the initiation site like 2,000-bp. But it cannot be excluded that such be even further upstream. All such regulatory elements regardless of position are within the scope of the invention.

The sequence, TATG---TAGT---TTT, which was proposed as a terminator of yeast (Zaret and Sherman, 1982) is found from residue 692 to 719, 59-bp downstream from the TAA translation termination codon (FIG. 4).

The ORF encodes an acidic protein (pI=4.02) consisting of 210 amino acid residues with a calculated molecular weight of 20,272. The TIP1 protein has a typical signal peptide and an extremely hydrophobic sequence at the C-terminal end. The TIP1 protein is thus secretable across the cell membrane and may be anchored on the outside surface of the plasma membrane.

Analysis of this putative protein sequence revealed a remarkably high content of Ala (20.0%) and Set (23.3%) residues (shown in the Sequence Listing as SEQ ID NO:2). The codon bias of the TIP1 gene was 0.65, which is characteristic of a relatively highly expressed yeast gene (Bennetzen and Hall, 1982). The N-terminal locus of the polypeptide has several common features with the signal peptide for secretary proteins (Duffoud et al., 1985). There is a basic amino terminal sequence followed by a stretch of hydrophobic amino acids. This signal peptide is probably cleaved at the C-terminal end of alanine residue at position +19. The ORF also contains an extremely hydrophobic sequence at the C-terminal end. Both sequences are underlined in FIG. 4.

The nucleotide sequence described and that of the ORF are illustrative of an embodiment of the invention (shown in the Sequence Listing as SEQ ID NO:1). As described further below, functionally equivalent sequences that encode functionally equivalent peptides are within the scope of the invention.

The nucleotide sequences illustrated herein that include the nucleotide sequence which encodes the described protein, is not limited to that particular sequence (shown in the Sequence Listing as SEQ ID NO:1). As is known, the genetic code is degenerate in the sense that different codons may yield the same amino acid, but precise in that for each amino acid, there are only one or more codons for it and no other. Thus for instance, all of the codons TTT and TTC when read as such, encode for phenylalanine; TTA and TTG for leucine, and TCT, TCC, TCG, TCA, AGT, AGC for serine, and no other amino acid. Thus, the invention includes within its scope those nucleotide sequences in which any one or several of the triplets are replaced by any one or more triplets capable of encoding the same amino acid. Thus, functionally equivalent sequences are within the scope of the invention whose translation brings about the peptides of the invention, or functionally equivalent peptides.

In that connection, the invention is not limited to the particular amino acid sequence, the peptides illustrated herein but does include those peptides which are functionally equivalent.

When expression systems are constructed which incorporate the gene (s) of the invention, or part thereof which encode the protein, the vectors may contain at least the gene(s) (or part thereof), and one or more promoters (heterologous or native). The expression system will also include other functional elements like an origin of replication and sequences to terminate transcription, or a gene to encode a protein (other than TIP1 or NOL1) with the native promoter of the TIP1 or NOL1 gene, or one or more other promoter with the native promoter in order to obtain the benefits of the invention, in particular thermo-tolerance and/or contribute to tolerance to low temperature.

With respect to the native promoter sequences as described above, it is within the scope of the invention to use a heterologous (non-native) promoter capable of regulating the expression of the genes of the invention in an appropriate host such as an eucaryotic competent cell like a yeast, such as of the genus Saccharomyces, fungi, including but not limited to Neurospora, Celphalosporium, Aspergillus, Penicillium and mammalian cells, like CHO or COS cells; other procaryotic competent cells, like of the genus Escherichia or Bacillus, like *E. coli* or *B. subtilisin*; Staphylococcus, Actinomyces, Serratia and Pseudomonas. Hosts are further described below.

Southern Blot Analysis.

Figure 6A:
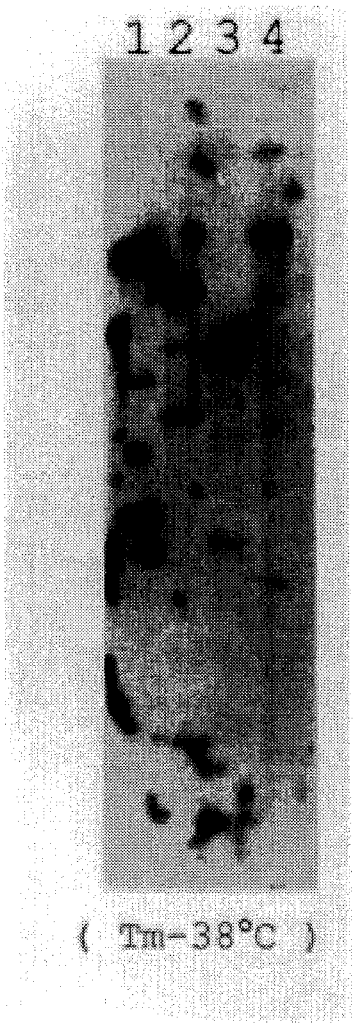
FIG. 6 (A and B) shows the Southern analysis of the TIP1 gene.
Figure 6B:
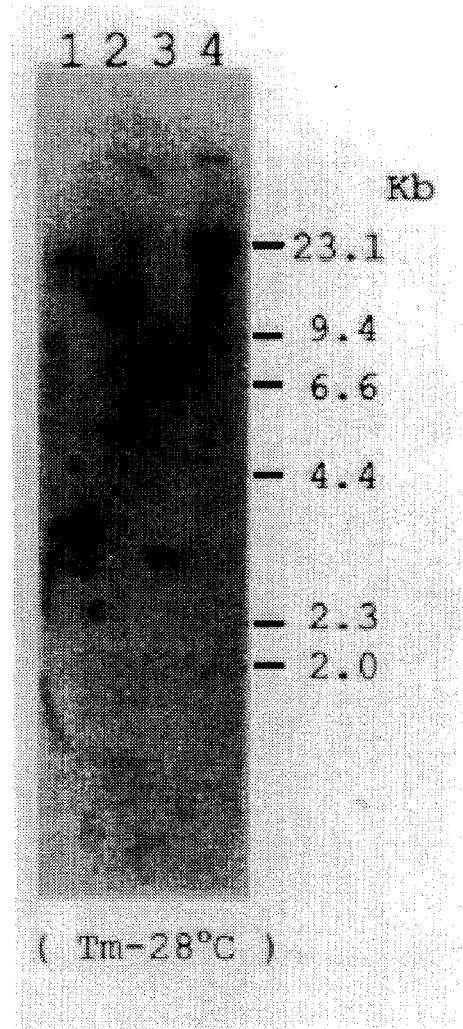

Southern blot analysis was performed using the BamHI-Sau3AI fragment containing the ORF and the 3' untranslated region as a probe (the BamHI site was created at nucleotide position +49 by PCR reaction). As shown in FIG. 6A, at least three or four distinct bands were detected in addition to a major band on each lane when the filter was washed under a low stringency condition: buffer 1× SSC, 0.2% SDS at 45° C.; $T_m$ of fragment used is 83° C., thus the wash was carried out at 38° C. below the $T_m$. One additional band remained when the filter was washed at higher stringency condition: buffer 1× SSC, 0.2% SDS at 55° C., $T_m$ of fragment is 83° C., thus stringent conditions require that washing be done at 28° C. below the $T_m$ (FIG. 6B). Those fragments which hybridize with the probe described above, are considered to code for genes within the scope of the invention.

In accordance with the invention, it was determined that TIP1 is a single copy gene. However, hybridization experiments done under low (permissive) stringency indicated the presence of 3 or 4 more similar, but distinct, genes in the yeast genome. One has about 70% homology to TIP1 and was found to be SRP1. The others therefor constitute genes of the family of TIP1.

All genes which are functionally equivalent to TIP1 are considered to be within the scope of the invention. Likewise, with respect to the encoded proteins, as further shown below.

Thus, the invention contemplates the expression of a gene encoding a low temperature induced functional peptide under the regulation of a heterologous promoter.

The invention further contemplates that after further elucidation of the nature of the promoter sequence, the promoter (or its equivalent) can be generated synthetically other than by methods of genetic engineering. Likewise, it can be foreseen that the protein(s) of the invention or their functional equivalent, or fractions of the sequences that are functionally equivalent may be synthesized by methods other than genetic engineering.

An important embodiment of the invention described herein are the DNA coding sequences of the genes (or parts thereof) (shown in the Sequence Listing as SEQ ID NO:1 and SEQ ID NO:3). It is within the scope of the invention to synthesize and isolate the desired DNA sequence(s) (all or part thereof) without cloning by polymerase chain reaction (PCR) by in vitro enzymatic amplification of a specific selected segment of DNA disclosed herein, for instance the ORFs or the upstream 5' segment containing the regulatory element(s).

The methodology of PCR is known. It is applicable to the DNA sequence taught herein. PCR involves using two small single-stranded oligonucleotide primers flanking the desired segment, the dsDNA to be amplified (all of the fragments disclosed or any part(s) thereof), and a DNA polymerase, appropriate deoxyribonucleoside triphosphates (dNTPs), buffers and salts. The primers hybridize to opposite strands of the DNA. With each successive round of amplification leads to many fold amplification of the selected discrete fragment. In this manner, any of the DNA fragment(s) of TIP1 or of NOL1 or of the members of the respective families with the desired homology (as described herein) can be amplified and isolated. For instance, the 1,584-bp Sau3AI fragment of TIP1, or the 2,017-bp NheI fragment-HindIII of NOL1, or any portion of the 5' region or of the 3' region or all of either one of the respective sequences, can be synthesized in vitro and isolated. For instance, sequences from translation initiation site +1 for any length upstream of the 5' region and/or sequences in the 3' region. Of special interest are sequences in the 5' upstream region which contain the regulatory element(s) desired. For a convenient source of information about PCR methodology, see *Current Protocols, supra*, Vol. 2, Unit 15.

The invention has been illustrated by inducing the genes by temperature changes. It is within the contemplation of the invention that other stress-inducing means also be suitable for inducing these genes, such as ethanol, glucose deprivation, changes in composition of nutrient media, heavy metal ions, anoxia, DNA-damaging agents like nalidix acid:, UV irradiation, bacteriophage infections, other known and yet to be discovered stress-inducing means.

Function of the TIP1 Gene at Low Temperature—Disruption of the TIP1 Gene.

To investigate the function of TIP1, a strain containing a deletion mutation in the TIP1 gene (mutant strain) was constructed by the γ-transformation method as described by Sikorski and Hieter (1989). Yeast strain SP1 and TD4 were transformed with plasmid pICS10 linearized by digestion with HindIII. The transformants were selected on SD plates lacking uracil. The disruption of the TIP1 gene was confirmed in transformants by Southern blot hybridization.

No difference in growth rate was observed between the parental strain and the mutant strain carrying tip1⁻ disruption at either 30° C. or 10° C. in rich or minimum medium.

To determine whether the TIP1 gene affects the viability at low temperature, the survival of the mutant strain after incubating cells at various low temperatures was examined. Cell were cultured to mid-log phase ($1\times10^7$ cells/ml) in YPD at 30° C., and aliquots from the culture were transferred immediately to 0, −5, −20, or −80° C. and kept for 2 days at the temperature. Remaining cultures were incubated at 10° C. for 2 hours to induce TIP1 expression before being transferred to lower temperatures. After 2 days viable cell counts at 30° C. were measured.

No difference in survival between the wild-type strain and the mutant strain was detected even with preincubation at 10° C. for 2 hours. The proteins homologous to TIP1 in the tip1⁻ disruption mutant cells may compensate for the deletion of the TIP1 protein at low temperatures.

Thus, since each cell has other genes homologous to TIP1, these results may be due to the contribution made by the genes homologous to TIP1 which assist TIP1 in conferring to the cells low temperature tolerance. Therefore the possibility is not excluded that TIP1 is involved in some function in contributing to cold tolerance of yeast.

Function of the TIP1 at High Temperature—Thermo-tolerance by TIP1.

Figure 7:
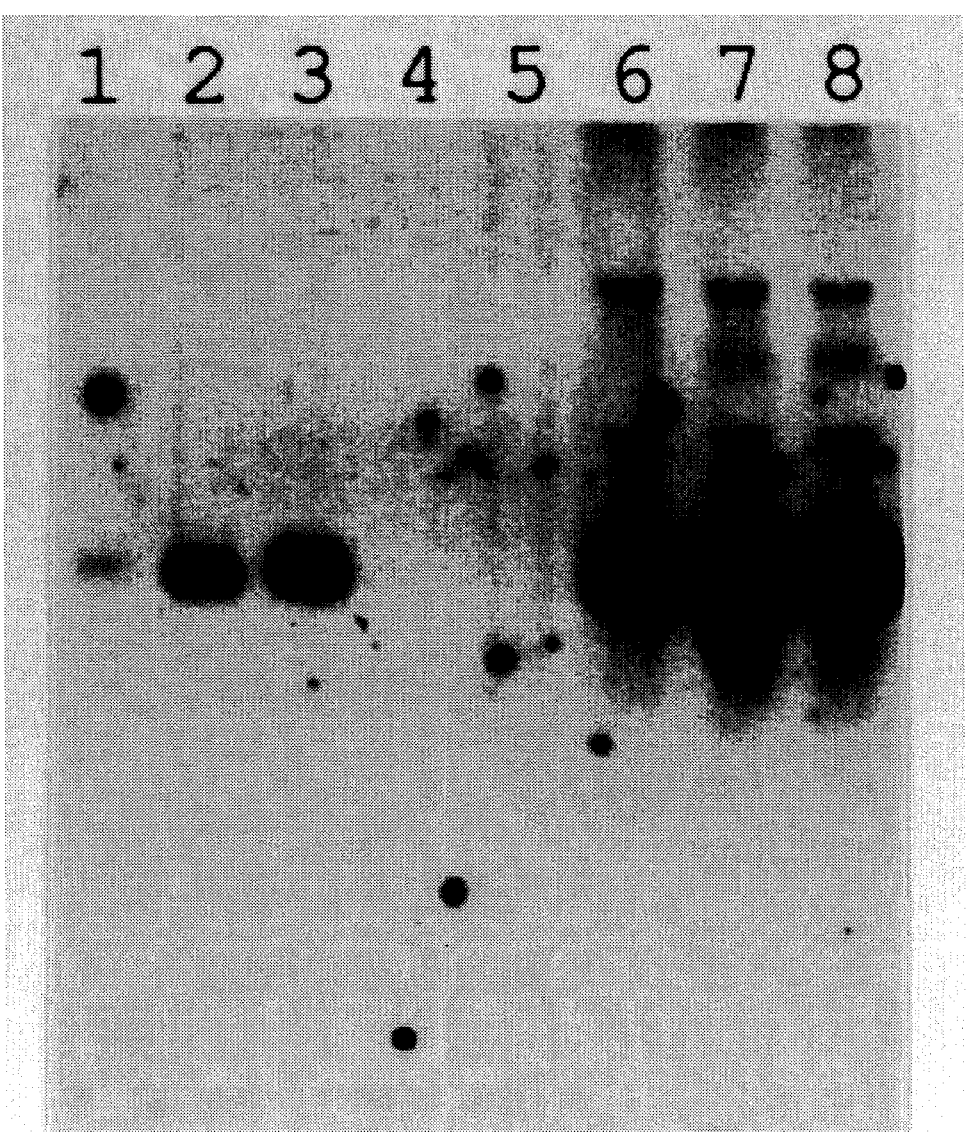
FIG. 7 shows the expression of the TIP1 gene in wild-type, tip1⁻mutant, or strain over-expressing TIP1.

Since it has been found that TIP1 mRNA can also be induced by heat-shock (FIG. 3C), the effect of the TIP1 gene on thermo-tolerance of the cells was examined. Before carrying out the experiment, a strain over-expressing TIP1 gene was constructed by transforming yeast with plasmid pYCA1 and examining the expression of the TIP1 gene by a Northern blot analysis (FIG. 7 ). The high level of expression was detected in the strain harboring pYCA1 even at 30° C. (lane 4) compared to that in the wild-type strain cultured at 30° C. (lane 1). The expression level was increased by cold-shock and heat-shock (lanes 5 and 6, respectively). No transcript of TIP1 was detected in the tip1⁻ mutant (lanes 7 and 8).

Figure 8A:
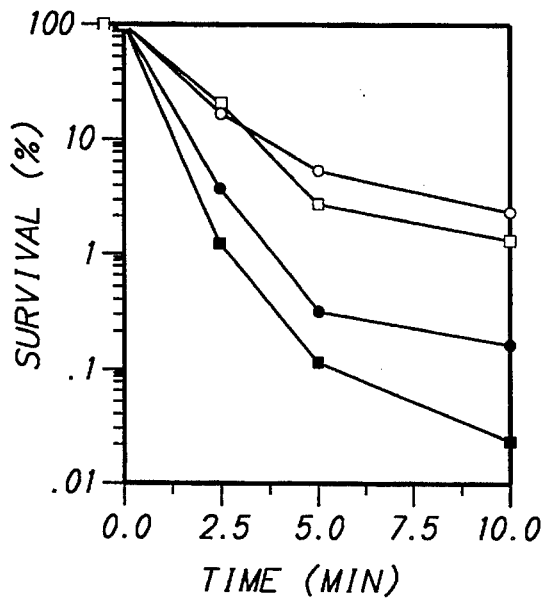
FIG. 8 shows the effect of the TIP1 gene on thermo-tolerance.

The wild-type and the tip1⁻ mutant strains were cultured to mid-log phase ($1 \times 10^7$ cells/ml) in SD medium at 24° C. and assayed for thermo-tolerance. Basal thermo-tolerance was determined by directly shifting the cells from 24° to 51° C. (FIG. 8A, solid symbols). Acquired thermo-tolerance was determined by shifting the cells from 24° to 51° C. after preincubation at 38° C. for 30 minutes (FIG. 8A, open symbols).

The wild-type strain rapidly lost viability when the culture was shifted directly to 51° C. The tip1⁻ mutant was more sensitive than the wild-type strain (FIG. 8A). The mutant cells acquired thermo-tolerance nearly the same degree as the wild-type cells but slightly lower than that after pre-incubation at 38° C. (FIG. 8A).

Figure 8B:
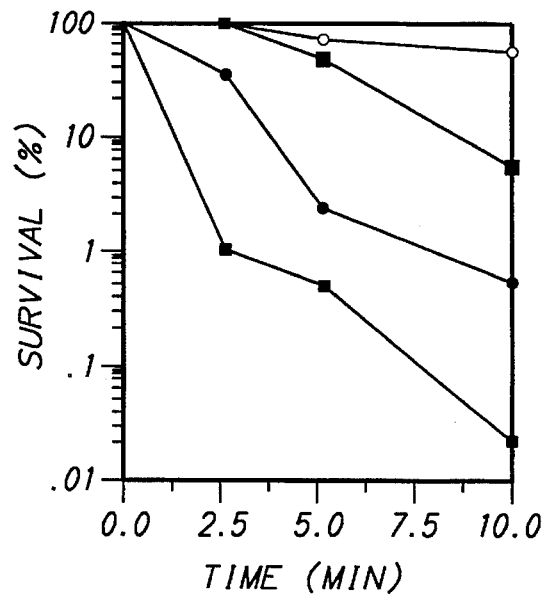

It has been reported that the expression of the SRP1 gene which is the most homologous gene (from the structural point of view) to TIP1 in yeast is positively modulated by glucose and the expression level of the SRP1 is significantly (5-fold) reduced by culturing cells in medium containing raffinose instead of glucose as a carbon source (Marguet and Lauquin, 1986). The thermo-tolerance of these three strains was examined by culturing cells in raffinose medium (FIG. 8B). The cells cultured in raffinose medium generally became more resistant to heat than the cells cultured in SD medium. However, the difference in the degree of viability between the wild-type and tip1⁻ mutant became much greater in raffinose medium compared to that observed in SD medium. The tip1⁻ mutant strain showed more than 20-fold reduction in survival compared to the wild-type strain after 10 minutes at 51° C. When pre-incubated at 38° C., the mutant cells acquired some thermo-tolerance of the same degree as the wild-type cells for the first 5 minutes after the temperature shift. However, the mutant cells showed a significant reduction in survival compared to the wild-type strain after 10 minutes at 51° C.

This work showed that with cells cultured in raffinose which is considered to contain less SRP1 protein, the effect of TIP1 deletion was enhanced.

Figure 8C:
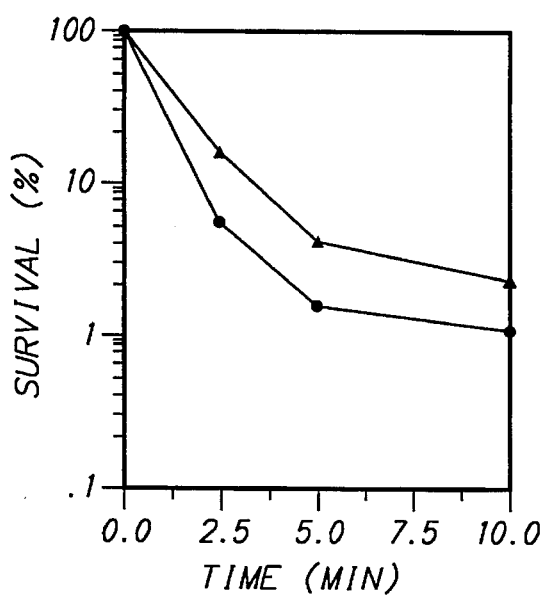

Surprisingly, the strain that constitutively over-expressed the TIP1 gene (transformed with plasmid pYCA-1) became more resistant to heat than the wild-type strain (FIG. 8C), while the tip1⁻ mutant exhibited significantly lower viability than the wild-type strain (FIG. 8A).

It is noteworthy that when cells lost the plasmid, they lost heat-resistance as well, clearly indicating that heat-resistance was conferred by the plasmid carrying the TIP1 gene. Tolerance at the temperature 38.5° C. close to its lethal temperature.

As described above, tip1⁻ mutant cells grew at rates indistinguishable from those of wild-type at 30° C. However, at 38.5° C. it was observed that tip1⁻ mutant colonies are much smaller than the wild-type after 3 days on agar plates. Under this condition, wild-type cells form colonies with jagged edges since this is the upper temperature limit for the growth of yeast cells (FIG. 23). Microscopic analysis revealed that the size of mutant cells were larger than wild-type cells and most mutant cells had one or two large buds at 38.5° C. (FIG. 24 B, D), whereas no observable difference was seen between wild-type and mutant strains at 30° C. (FIG. 24 A and C). The cell cycle is not completely arrested as with the cdc mutation since mutant cells can still grow and form colonies at the 38.5° C. temperature. This observation indicates that the tip1⁻ mutant is more sensitive to the high temperature than wild-type cells. The TIP1 product may have an important function in promoting cell separation.

A tentative conclusion is that the TIP1 gene may contribute to confer thermo-tolerance at that temperature, a temperature above the usual optimum growth temperature of yeast and close to its lethal temperature (about 40° C.). Further, it emphasizes the practical importance of an organism like yeast transformed with a high expression vector like pYCA1 since it has thermo-tolerance over a wide range of temperature such as ranging from about 38° to 51° C. or eventually higher.

From the work described herein, it is noteworthy that TIP1 is inducible both at low and high temperature and at least contributes or does confer high temperature tolerance. The practical applications of these unusual properties of this family are described below in greater detail.

Characterization of the Gene Encoding 1.6-kb Cold-Shock Inducible Transcript and DNA Sequence, Gene of Group B. A second important embodiment of the invention relates to a cold-shock induced gene herein designated as NOL1, The gene encodes and over-expresses at low temperature a protein which is described further below. The gene also encodes a 1.6-kb transcript, The restriction maps of two plasmids containing the gene hybridizing with the 1.6-kb transcript were constructed (FIG. 10), pDCS52 contained a 4.5-kb fragment and pDCS84 contained a 2.5-kb fragment, The approximate position of the sequence encoding the 1.6-kb transcript was determined by Southern blot hybridization of the plasmid DNA fragments with $^{32}$P-labeled cDNA probe prepared from cold-shocked cells, This analysis verified that the region bounded by HpaI and HindIII sites was transcribed, Subsequently the DNA sequence of the 2017-bp (SEQ ID NO:3) NheI-HindIII fragment containing the transcribed region was determined. Examination of the sequence revealed a single long open-reading frame (ORF) of 1,163-bp (without termination codons) (FIG. 11) capable of encoding a 414-amino acid protein. The sequence for the promoter elements is likely to be located upstream 1,500 or even in a 2,000-bp nucleotide sequence, upstream of the initiation site in the 5'-untranslated region. The possibility however cannot be excluded that for NOL1 (or genes homologous to NOL1) such regulatory elements be positioned even further away as for instance 2,500-bp. Other regulatory elements likely to be located in that region include an upstream activation sequence (UAE) element, TATA element and an initiation transcription site. All these elements upstream of the initiation codon are within the scope of the invention. A putative TATA box which is likely to be a putative promoter important element for NOL1 expression is located from residue −156 to −149 in the 5'-flanking region upstream of the initiation site ATG. The sequence, TAGT - - - TAG - - - TTT, which is similar to the terminator sequence is located from residue +104 to +136-bp downstream from the TAA termination codon. The polyadenylation signal of higher eucaryotes, AATAAA exists in the 3'-flanking region (from +279 to +284) (FIG. 11).

The amino acid sequence of NOL1 is shown in FIG. 18 (SEQ ID NO:4). Its nucleotide sequence is shown in FIG. 20 (SEQ ID NO:3). The Figures are described further below.
Regulation of the Gene Encoding the 1.6-kb Transcript.

Figure 12A:
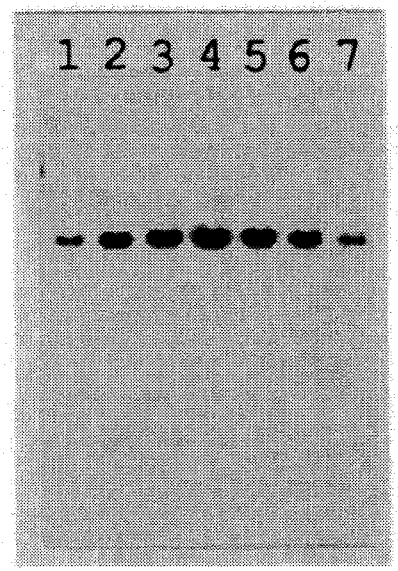
FIG. 12 shows the regulation of expression of NOL1.
Figure 12B:
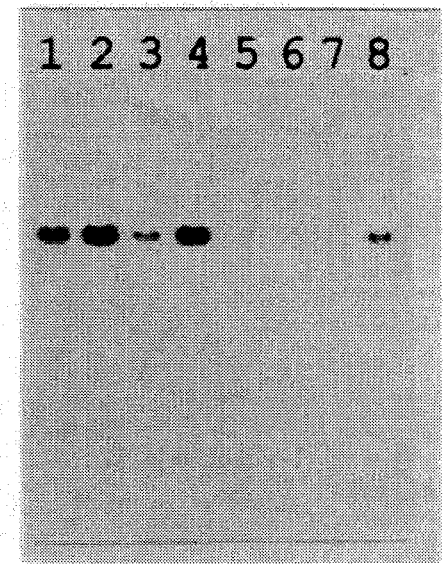
Figure 12C:
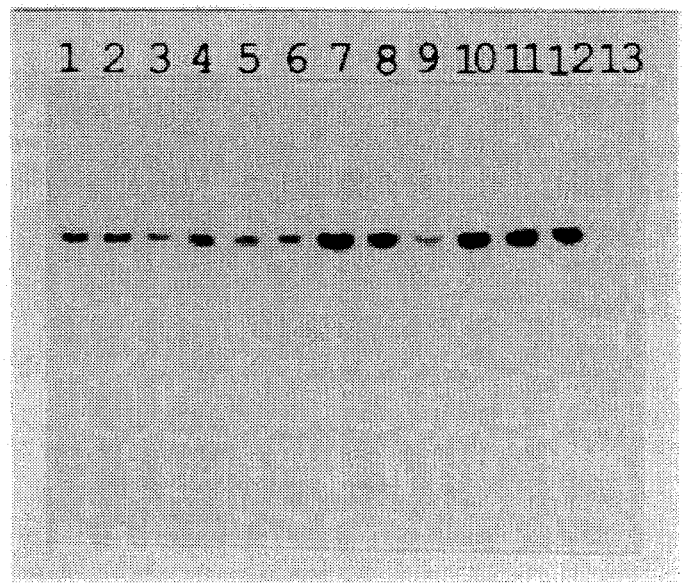

A series of Northern blot experiments were performed using total RNA prepared from cells subjected to various conditions of temperature shock in order to clarify the regulation of expression (FIG. 12). The HpaI-KpnI fragment containing the 5' part of the ORF was used as a probe for this analysis. A low level of gene expression was detected at 30° C. and the amount of the mRNA increased after the temperature drop from 30° to 10° C. (FIG. 12A). The highest level of the mRNA was observed 4 hours after the temperature shift and the amount of mRNA decreased to the basal level after 10 hours (FIG. 12A). The mRNA was detected only at mid-log phase but it was not observed at the early stationary phase or at the late stationary phase in the cells grown at 30° C. (lanes 1, 3, 5, and 7 in FIG. 12B). The increase of mRNA by cold-shock was observed at mid-log phase and stationary phase (lanes 2, 4, and 8 in FIG. 12B). For the definition of the density of the cell cultures, see above.

With respect to the NOL1 gene, it was discovered that it is over-expressed at reduced temperature, that is by cold-shock. The highest level of induction appears to result from the temperature shift, i.e., shift in temperature as opposed to the specific lower temperature assayed. The best level of induction was observed in a temperature drop from 30° to 10° C. (lane 7, FIG. 12C), or from 37 to 10° C. or 15° C. (lanes 10 and 11 in FIG. 12C). The expression of the gene was not induced by temperature shift from 30° to 39° C. (lane 13, FIG. 12C), from 30° to 5 or 21° C. (lanes 6, and 9, in FIG. 12C), or from 21 to 10° or 15° C. (lanes 4, and 5, in FIG. 12C).

It is noteworthy that the 1.6-kb transcript is cold-induced but apparently not heat-shock induced, as opposed to the 1.0-kb transcript which is both heat and cold-shock induced.
Structural Features of the Predicted NOL1 Polypeptide.

Figure 13:
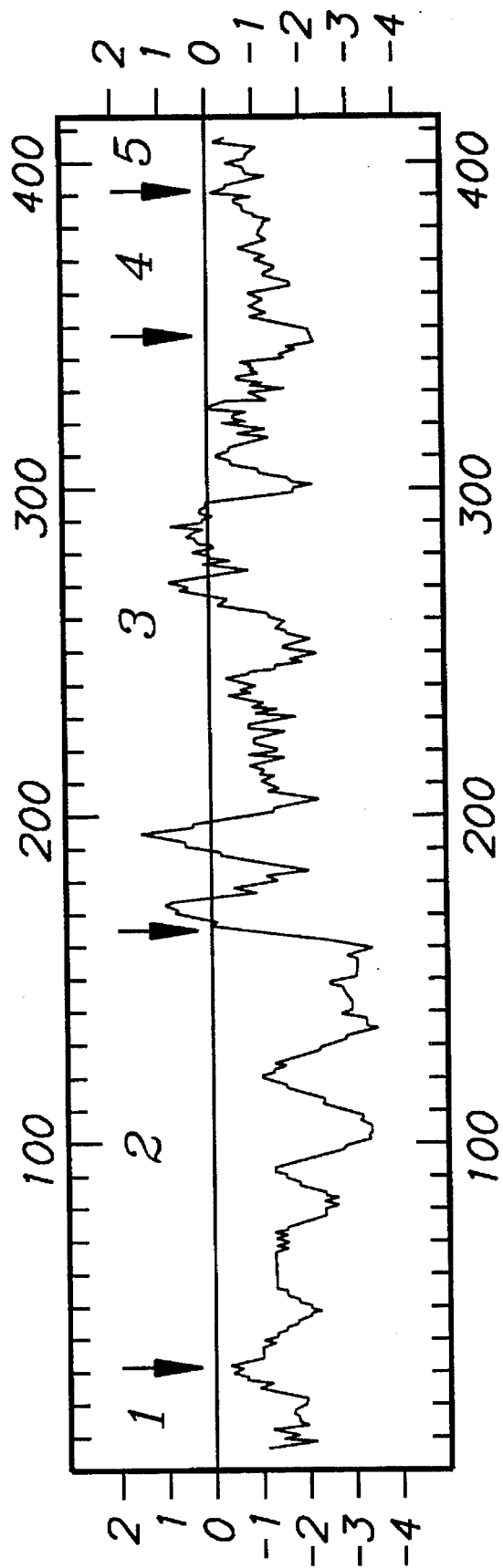
FIG. 13 shows a hydrophilic plot of the predicted NOL1 protein.

The ORF of 1,242-bp (SEQ ID NO:4) encodes an acidic protein (pI=4.69) consisting of 414 amino acid residues with a calculated molecular weight of 44,535. Analysis of the protein sequence revealed a number of interesting features. The protein is rich in serine (20.5%), glycine (10.1%), acidic (20.3%)and basic (15.7%) amino acid residues, which are clustered in several regions of the molecule. The hydropathy profile of the predicted protein is hydrophilic and there are several hydrophobic segments in the central part of the protein (FIG. 13). The protein can be divided into 5 domains as follows: the first N-terminal domain (1-28) is hydrophilic and positively charged by 10 lysine and 3 glutamic acid residues. The basic domain is followed by a serine and acidic amino acid rich domain (29-166) containing 65 serine (47.1%), 39 glutamic acid (28.3%), and 10 asparatic acid (7.2%) residues. This second domain is extremely hydrophilic and does not contain any hydrophobic amino acid residues such as Ile, Leu, Met, Val, Phe, Trp, and Tyr. There are three stretches containing 37 (29-76), 10 (85-97), and 14 (113-131) serine residues. These stretches are interspersed with acidic amino acids (8 Glu and 1 Asp in the first stretch and 1 Asp in the second and third stretches, respectively). There are also two stretches containing 9 acidic residues each (98-106 and 144-153), which are interspersed with lysine or alanine. The third domain (167-350) consists of two tandemly repeated peptides and contains several hydrophobic segments. Most of the hydrophobic amino acid residues of the polypeptide are located in this domain [32 out of total 37 (Ile+Leu+Val+Met), 19 out of total 24 (Phe+Trp+Tyr)]. The fourth domain is a glycine plus arginine rich domain containing 23 Gly and 9 Arg residues (351-391). The fifth domain in the C-terminal region (392-414) does not have any particular feature.

The characteristic features of the gene encoding the 1.6-kb transcript distinguish it from other genes and known proteins.
Comparison of the Amino Acid Sequence with Other Proteins.

A homology search of the amino acid sequence with that of all the proteins in current databases using the method of Pearson and Lipman (1988) revealed that the two tandem repeats in the third domain of the protein (167-350) exhibit significant identity with the RNA-binding domains of a number of RNA-binding proteins from different organisms. Alignment of the putative RNA-binding domains of this protein with human nucleolin, yeast poly (A) binding protein, and human snRNP U1 70K are shown in FIG. 14A. Each repeat of the predicted sequence shares 35.4% amino acid identity (59.8% homology) to each other and contains two highly conserved segments which are common in RNA-binding proteins (RNP1 and RNP2; see FIG. 14A). This analysis also revealed that the glycine and arginine-rich domain at the C-terminal region (352-391) has a striking similarity with the C-terminal glycine-rich domain of mammalian nucleolin, having 83% amino acid identity with human nucleolin (FIG. 14B). The first and second domains do not show significant similarity to any other proteins in current databases. In addition to the glycine-rich domain, the third domain of the present protein containing two putative RNA-binding domains shares similarity with the third and fourth RNA-binding domains of human nucleolin (29.9% identity, 51.1% homology; FIG. 14B). These results demonstrated that the predicted protein may be a nucleolin-like protein in yeast. This gene was designated for convenience only, NOL1 (nucleolin-like protein).

These results also establish significant dissimilarities of the structural domain in the amino acid sequence of NOL1 compared to that of mammalian nucleolin (FIGS. 14A, 14B and 17). Illustrative differences are discussed below.
Phenotype of the NOL1 Gene Disruption Mutant.

To investigate the function of NOL1, a strain carrying a mutation in the NOL1 gene was constructed by the γ-transformation method as described by Sikorski and Hieter (1989). Yeast haploid strain SP1 and diploid strain KN1 were transformed with plasmid pICS16 linearized by digestion with HindIII. Ura$^+$ transformants were selected on SD plates lacking uracil. However, there was no significant difference in the number of transformants between the two strains. The disruption of the NOL1 gene in the haploid strain was confirmed by Southern blot analysis.

The above result indicated that the NOL1 gene was not absolutely essential for cell growth.

At 30° C. the doubling time of the mutant was 3.0 hours, 1.5 times slower than the wild-type strain. When the nol1$^-$ mutant, growing logarithmically at 30° C., was transferred to 10° C., about 4 hours-lag in growth was observed.

These results showed that the NOL1 protein provides a function needed for normal growth of cell and the induction of NOL1 protein by cold-shock is necessary for cell to continue growing without lag in growth.
Southern Blot Hybridization Analysis.

It has been reported that nucleolin is a major nucleolar protein and is involved directly in ribosome biogenesis in higher eucaryotes. Bouche et al. (1984), Caizergues-Ferrer et al. (1987) and Srivastava et al. (1990). There is no disclosure that stress, in particular cold-shock would induce the gene nor what properties the 100-kDa phosphoprotein nucleolin could confer to an organism.

Figure 15:
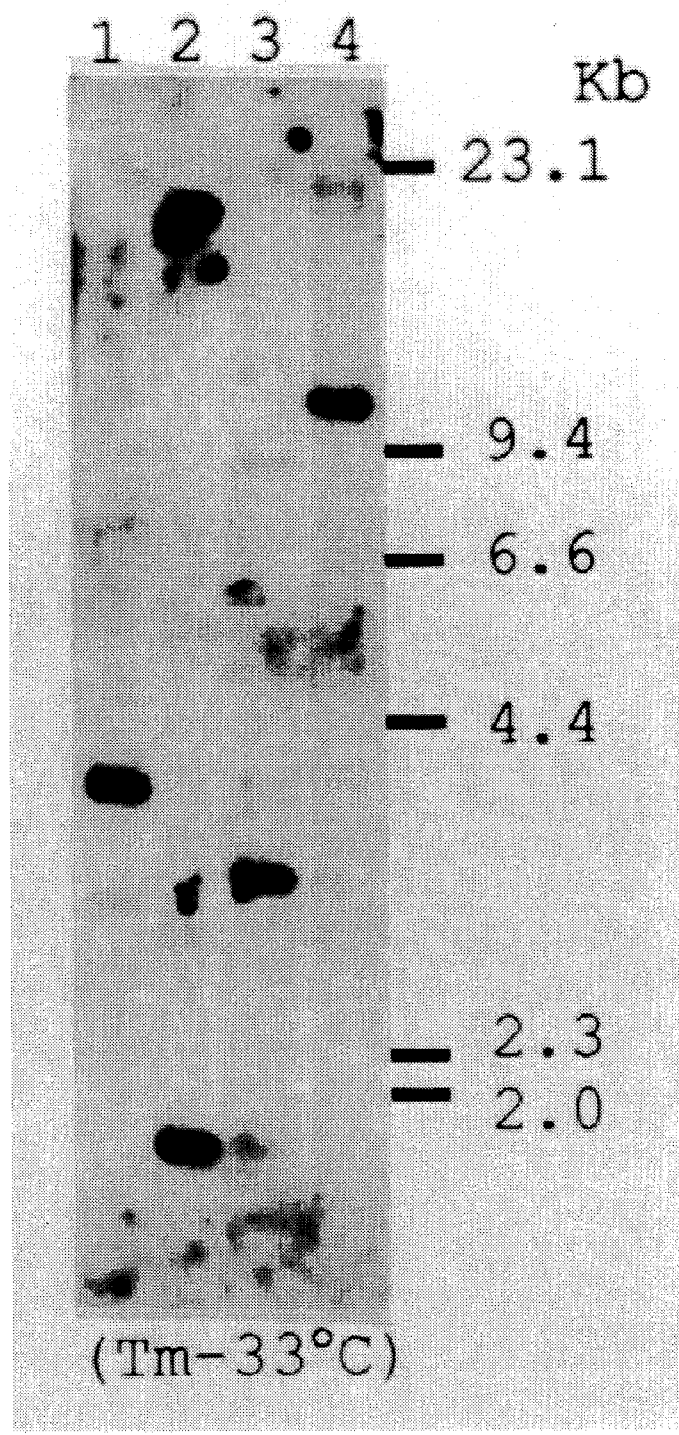
FIG. 15 shows Southern blot analysis of the NOL1 gene.

The fact that as shown herein, the NOL1gene was not absolutely essential for cell growth suggests possible existence of another gene(s) homologous to NOL1in the yeast genome. To determine whether there are genes homologous to NOL1in the yeast genome, Southern blot hybridization was performed using the HpaI-HindIII fragment (FIG. 10) as a probe. As shown in FIG. 15, one additional band was detected other than the main band when the filter was washed under a low stringency condition (1× SSC, 50° C. The $T_m$ of this fragment was 83° C.; the wash was performed 33° C. below the $T_m$. This result indicates that the NOL1gene is a single copy gene and there is at least one other gene homologous to NOL1present in the yeast genome.

As discussed above, genes or part thereof which have such sequence homology to genes encoding functionally equivalent proteins are within the scope of this invention; and so are the encoded proteins.

Characterization of the Protein Encoded by NOL1.

Figure 16:
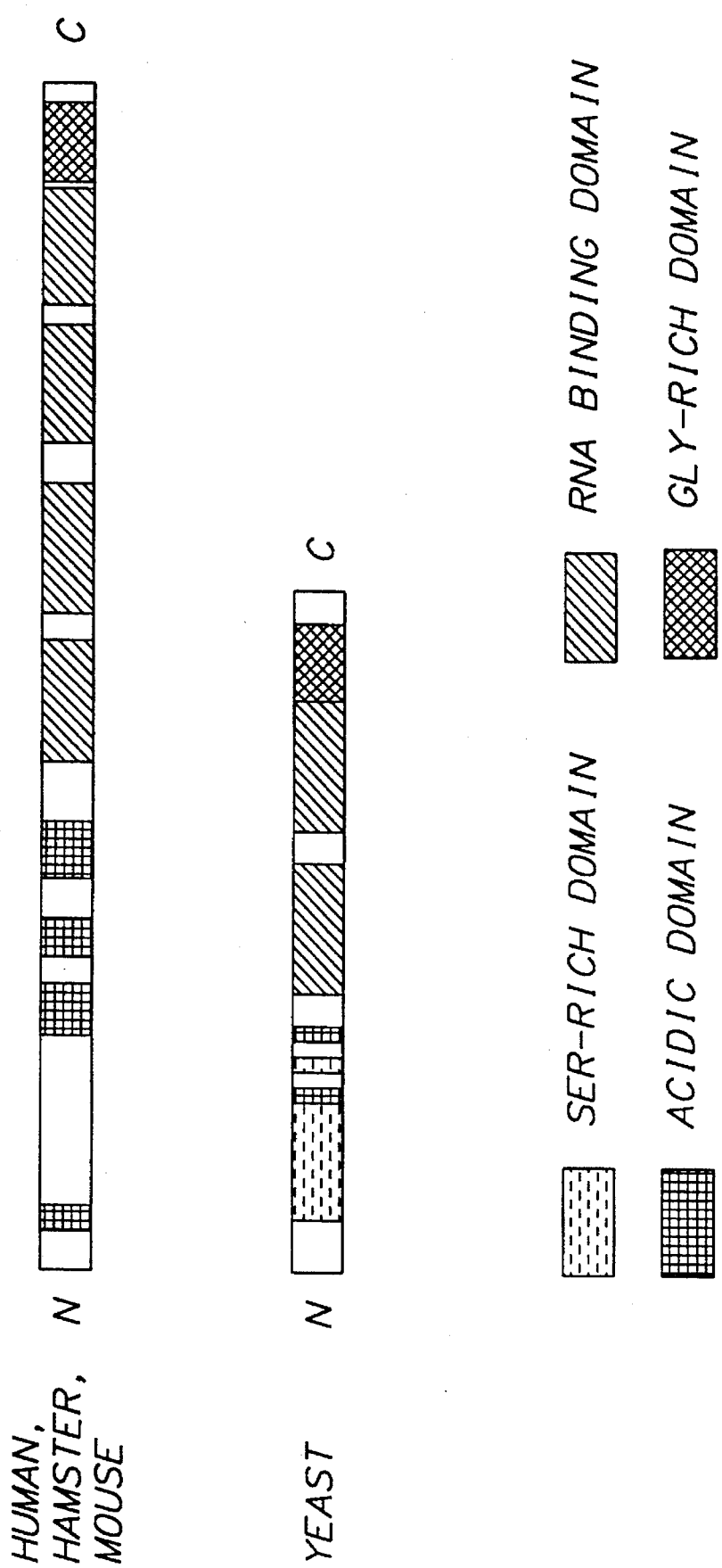
FIG. 16 shows the domain arrangements and differences between the mammalian nucleolin and NOL1.

It was found that the NOL1gene shares some similarity with mammalian protein nucleolin (as discussed above) but shows significant differences (see FIG. 16). Comparison between the two proteins shows that NOL1has two RNA binding domains as opposed to the four of nucleolin. Further, the N-terminal half of these proteins differ from each other. Moreover, NOL1exhibits a very serine-rich domain to which there is no counterpart in nucleolin (human, hamster or mouse). Thus, the NOL1is unique in structure.

SRP1 is a Cold-Shock Induced Protein.

The yeast gene encoding a protein rich in serine residues (SRP1) has been studied. Marguet et al. (1986), Marguet et al. (1988). A comparison of the TIP1and SRP1amino acid sequences reveal that both proteins have substantial sequence similarity (50% identity) (FIG. 9) which extends from the N-terminal putative signal peptide; to the C-terminal hydrophobic sequence. Marguet (1986) show that the expression of the gene is positively regulated by glucose as compared to cells grown in raffinose or glycerol/ethanol.

In accordance with the invention, the effect of cold-shock on induction of SRP1was investigated. The most homologous gene to TIP1which was detected by Southern analysis, SRP1was cloned from a yeast genomic library essentially according to the method described by Beltz et al., *Method in Enzymology*, Vol. 100, p. 266 (1983). Four clones which hybridized with XbaI-PvuII fragment of TIP1 under permissive condition but which did not hybridize under high stringency condition, were cloned. Restriction enzyme analysis revealed that these clones contained the same gene. A DNA sequence analysis identified this gene to be the SRP1 gene. Northern blot analysis was carried out using 0.8-kb EcoRI-XbaI fragment containing the ORF and 3'-flanking region of SRP1gene as a probe. RNA was prepared from yeast cells which were grown first at 30° C. (in normal medium [YPD]) to an $OD_{600}=2$ and then subjected to cold-shock for 2 hours at 10° C.

The results indicated that the SRP1 is also induced by cold-shock. The cold-shock induced SRP1thus may confer thermo-tolerance and/or low temperature tolerance to the transformed microorganisms, such as a yeast *S. cerevisiae*. It has been found in accordance with the invention, that the gene encoding SRP1is a cold-shock gene, i.e., cold-shock induced.

The family of yeast genes of the invention are capable of expressing proteins within the scope of the invention and are identified as described, by nucleic acid hybridization under conditions of varying degrees of stringency and permissiveness. The isolation of multi-gene families within the scope of the invention may be made by known procedures. See *Methods in Enzymology*, Vol. 100, "Recombinant DNA (Part B)" edited by Ray et al., Academic Press, Inc., Section 19, "Isolation of Multigene Families and Determination of Homologies by Filter Hybridization Methods" by Beltz et al., page 266 and seq. Reference may also be made to Current Protocols which describes hybridization techniques particularly in Sections 2.9.1, 2.9.10, and 6.3.1–6.3.5. To recover all members of a multi-gene family of the invention, the steps for permissive and stringent hybridization conditions are described in these references.

Various factors are known to affect the melting temperature $(T_m)$ of the DNA-DNA hybrid between the probe and the fragment of interest, and consequently the conditions for hybridization and washing. As is often the case, the probe is not 100% homologous to the fragment.

Other commonly encountered variables include the length and total G+C content of the hybridizing sequences and the ionic strength and formamide content of the hybridization buffer. The effects of all of these factors can be approximated by a single equation:

$$T_m = 81.5 + 16.6(\log_{10} C_i) + 0.41[\%(G+C)] - 0.63(\% \text{ formamide}) - 600/n - 1 - 1.5(\% \text{ mismatch})$$

where $C_1$ is the salt concentration (monovalent ions) and n is the length of the hybrid in base pairs (slightly modified from Meinkoth and Wahl, 1984).

To identify genes (or functional fractions thereof) of members of the multi-gene family of TIP1and of NOL1, an initial screening is performed under permissive criterion. As is described in the above reference (*Methods in Enzymology*, Vol. 100), a criterion of 40° to 50° below $T_m$ is desirable to recover even distant homologs. To discriminate between homologs, a more stringent criterion should be used in a second and if desirable, further hybridization steps. For details of the procedure, see the above references.

As shown above, The filters were washed under the following conditions: For TIP1at (a) 28° C. below the $T_m$ and (b) at 38° C. below the $T_m$. Gene(s) (or fractions) which have more than about 58% to substantially or complete homology should be detected when condition (a) applies, and when condition (b) apply, gene(s) of a homology from about 43% to substantially or complete homology should be detected. For NOL1 at 33° C. below the $T_m$, gene(s) having about more than 50% to substantially or complete homology should be detected.

Those genes which are functionally equivalent to TIP1and to NOL1 and the encoded proteins which are physiologically equivalent, are considered within the scope of the invention.

The term "functionally" usually herein means the functional equivalence of a DNA sequence with the gene (or fraction thereof) which encodes TIP1(or a functional portion thereof) or NOL1(or a functional portion thereof) or a protein which confers or contributes to conferring thermo-tolerance to the transformed organism, or in general, for the organism to acquire or develop under conditions outside the normal physiological growth conditions. The term "physiologically" equivalent means herein a protein (or a polypeptide) which has physiological or biological function that is equivalent to that of the protein expressed by organisms in which genes of the invention have been induced and in organisms transformed with the genes of the invention or of fragments thereof.

As described above, a suitable competent vector in which one or more genes of the invention or fragments thereof have been incorporated can be used for expressing the proteins of the invention. Such suitable vectors are known and described in the literature. Two suitable high expression vectors presently preferred to obtain high level inducible expression of a cloned gene (or part thereof) of the invention in yeast are plasmid YEp51 and YEp52. These plasmids are described in *Experimental Manipulation of Gene Expression*, Chapter 5, "Vectors of High-Level, Inducible Expression of Cloned Genes in Yeast", Broach et al., Academic Press, Inc. (1983). Their construction is shown in Inouye, infra. (pps. 108-110); isolation of promoter fragment of GAL10 (at pps. 107-108) and of fused expression vectors (at pps. 113-114). Other suitable expression vehicles include such popular multicopy vectors like YEp24 (Botstein et al., Gene, 8, 17 (1979)) and pJDB207 (Beggs, *Genetic Engineering* (ed. Williamson), Vol. 2, p. 175, Academic Press (1982)). Others that may be selected include plasmids of the classes YIp, YRp, YCp, YEp and YLp. With the exception of YLp plasmids (yeast linear plasmids), all others are shuttle vectors that can be maintained in *E. coli* as well as in *S. cerevisiae*. The following may be considered for selection: YIp5, YRp7, YRp17, YRp13, YRp24, YRp19, YRp50, YRp21, and pYAC3. Other suitable vectors are described in Vol. 2, sections 13.4.1, 13.4.2 (1989), Current Protocols (cited below).

When it is desired to place the TIP1or NOL1ORF under the control of a heterologous promoter for expression in a vector like a YEp vector (YEp51 or YEp52), GDP promoters as in pGPD-2 or pGPD-1 (Bitter and Egan, Gene, 32 268 (1984)) or ADC1 promoters as in AAH5, AH5, AH9, AH10 or AH20 (Ammerer, *Methods in Enzymology* (ed. Wu et al.), Vol. 101, p. 192, Academic Press (1983)), or the PH05 promoters as in pAT77 or pAM82 (Miyanohara et al., *Proc. Natl. Acad. Sci. USA*, 80, 1 (1983)) are to be considered.

Likewise, the region described herein as the UAS element of TIP1can be fused with a TATA element and initiation element of another strong promoter such as GPD, ADC1, PGK, GAL1 or GAL10.

Fused (chimeric) promoters are expected to be strong promoters and can be controlled by cold- and heat-shock.

Other promoters are described below, in particular see *Inouye*, cited infra. The use of retrovirus:derived vectors offer a general approach (see *Inouye*, infra. (Chapter 9).

For cloning vectors in mammalian cells, the following may be considered: pSVL (SV40 promoter), pMSG (dexamethasone inducible transcription, promoter from mouse mammary tumor, virus LTR), pKSV-10 (SV40 early promoter reg.), pSVN9 (SV40 early promoter), pOLUC (promoter less), pSV2LUC (SV40 promoter), pϕGH and pXGH5.

For expression in plants, cloning vectors like the following may be considered: Octopine-type 1 Ti, Octopine-type 2 Ti, Nopaline Ti, Agropine Ti and Rhizogenes Ri.

Cauliflower mosaic virus 35S RNA is a possible promoter for expression in plant cells. For further information on expression in plant cells, see *Genetic Engineering of Plants*, editors Kosuge et al., Basic Life Sciences, Plenum Press, 1983.

Also see "Expression and Secretion Vectors For Yeasts" in *Methods in Enzymology*, Vol. 153 (1987), Bitter et al., Academic Press, Inc. and *Genome Organization and Expression in Plants*, Ed. C. J. Leaver, Plenum Press (1980). Vectors which are designed for efficient expression of heterologous genes have been developed which employ promoter elements derived from alcohol dehydrogenase (Hitzeman et al., *Nature (London)*, 293, 717 (1981), phosphoglycerate kinase (Tuite et al., *EMBO J.*, 1, 63 (1982), acid phosphatase (Miyanohora et al., *Proc. Natl. Acad. Sci. U.S.A.*, 80, 1 (1983), glyceraldehyde-3-phosphate dehydrogenase (Bitter et al., Gene, 32, 263 (1984), galactokinase (Goff et al., Gene, 27, 35 (1984), and mating factor-α genes (Bitter et al., *Proc. Natl. Acad. Sc. U.S.A.*, 81, 5330 (1984). For instance, it is known that the 5'-flanking DNA sequence from a yeast gene for alcohol dehydrogenase can provide the expression of a foreign gene when placed in a plasmid used to transform yeast. Likewise, the 3-phosphoglycerate kinase 5'-flanking sequence can function to promote expression of foreign genes in yeast. Eucaryotic expression vectors are also commercially available. For instance, from *Pharmacia LKB Biotechnology*. Likewise, procaryotic expression vectors such as pKK223-3, pKK233-2 and pPL are also available from the commercial sources. To clone any one of the genes of the invention in multi-cloning sites of the competent vector, suitable restriction sites are introduced by PCR reaction to the termini of the appropriate genes.

For suitable methods for over-expressing large amounts of protein from eucaryotic or procaryotic organisms, reference may be made to *Molecular Cloning: A Laboratory Manual*, Sambrook et al., 1989, Cold Spring Harbor Laboratory, Chapter 17, *Current Protocols in Molecular Biology*, Vols. 1 and 2, editor Ausubell et al., publisher Green Publishing Associates and Wiley Interscience. See Unit 1 for *E. coli* Plasmid and Bacteriophages; Unit 6 for screening recombinant DNA libraries including hybridization with radioactive probes; Unit 9 for introduction of DNA into mammalian cells, including transfection of DNA into eucaryotic cells; Unit 10 for analysis and separation of proteins and Unit 16 for protein expression in *E. coli* and expression of proteins in mammalian cells.

Further, useful reference may be made to *A Practical Guide To Molecular Cloning*, Perbal, Second Edition, john Wiley & Sons (1988). Useful is particularly Chapter 25, expression of cloned DNA sequences in procaryotic and eucaryotic cells. Also see *Experimental Manipulation of Gene Expression*, editor Inouye, Academic Press, 1983.

That book describes multi-purpose expression cloning vehicles useful for high level expression of cloned genes in yeast. Two classes of vectors are described. Those designed to obtain high level synthesis of the authentic target protein—or a clone variant thereof—of a cloned gene of interest and those designed to produce a hybrid protein. Promoters which RNA polymerase II recognize lie immediately and completely 5' to the site of transcriptional initiation of the gene. High level expression of a cloned gene in yeast is best achieved by its fusion to the selected promoter of a yeast gene that is normally expressed at high levels. In Saccharomyces, highly expressed genes are almost exclusively those encoding glycolytic enzymes or enzymes otherwise involved in carbon metabolism. Expression from promoters of genes encoding glycolytic enzymes is essentially constitutive. Such suitable promoters are described in Inouye, cited supra, page 89, and above. Vectors for high level expression in yeast are described on pages 100–104 which are a suitable source for vectors for transforming organisms in accordance with the invention.

The purification of the expressed proteins in *E. coli* can be performed in accordance with standard protein purification methods. See for instance, *Protein Purification: Principles and Practice*, Scopes, Springer Flag, N.Y. (1987). Appropriate competent host cells may be transformed with the genes (or fraction thereof) of the invention to express useful products. The protein is extracted and purified by preparing a cell extract of tile E. coli containing the expression plasmid; the expression of the protein is induced by adding an inducer such as IPTG (for vector pKK223-3 or pKK233-2) or by raising the temperature of the culture medium (pPL-Lambda Inducible Expression Vector). The cells are harvested by centrifugation and disrupted by sonication. For the expressed proteins which are soluble, the soluble fraction containing the protein is collected by centrifugation of the sonicated sample. The soluble fraction may be fractionated using for instance, ammonium sulfate precipitation in accordance with general practice.

The desired protein of the invention are then separated by ion exchange chromatography, such as an anion exchange column such as DEAE cellulose or DEAE Sephadex (Pharmacia) columns. The isoelectric point (pI) of TIP1is 4.02 and that of NOL1is 4.69. These low pHs facilitate obtaining very pure proteins in just one single step. The fraction containing the protein is dialyzed against a low pH buffer (6.5 or lower) and applied to the column equilibrated with the same buffer. The protein is then eluted using linear gradient of NaCl.

If desired, the proteins of the invention can be separated or isolated by other methods on the basis of their molecular weight (e.g., using Sephadex column chromatography). Immunoaffinity chromatography can also be used for TIP1protein (anti-sera for TIP1protein developed in conjunction with this work).

Other methods of purification may be used as desired, such as protein fusion and purification system as described and available from New England Biolabs (NEB) which provides a comprehensive method for the production and purification of a protein expressed from a cloned gene or open-reading frame. Other suitable methods known in the art may also be used.

The invention covers eucaryotic or procaryotic organisms in which when subjected to stress, e.g., cold-shock, the genes which encode the proteins of the invention are induced, and then over-expressed by the organism in which the gene was induced or by competent transformed organisms.

Broadly, the invention covers organisms, especially eucaryotes which when subject to a stress condition, e.g., cold-shock, a stress-inducible gene, e.g., cold-shock inducible gene is induced which gene encodes a protein which is capable of contributing to or conferring thermo-tolerance and/or capable of conferring low temperature tolerance to the organism that was subjected to stress or to a transformed organism.

In that connection, it should be noted that cross-stress and property(ies) are within the scope of the invention. A form of stress can induce a better tolerance to that condition or to a different condition. Illustratively herein, cold-shock does not only cause improved tolerance to low temperature but cause thermo-tolerance.

Amongst the eucaryotes which are of particular interest are mammalian cells, plant or vegetable cells, cells of insect, cells of animals like ovarian, pesces, and others to be subjected to low temperature shock in accordance with the invention. In the first group, the invention includes COS, CHO and HeLa, BALB/c 3T3, NIH 3T3 cells, rat embryo fibroblasts and other mammalian cells. Some of these cells (like CHO DUKX) when subjected to glycerol or DMSO have their transfection efficiency increased. This measure can be considered in connection (before, after, etc.) with cold-shock.

The cells of the organisms described above can be grown (preferably exponentially) as described in the literature (for instance, in Current Protocols, Section 9) generally at about 37° C. then subjected to cold-shock in accordance with the invention, to any lower most effective temperature like to temperatures at 20°, 15°, 10°, 5° C. or below. By the preparations and methodology described herein, cold-shock induced genes and proteins encoded thereby are ascertained, identified and characterized for their property of contributing to thermo-tolerance and/or low temperature tolerance.

In a like manner, plant cells can be cultured and tested for induction by cold-shock of the genes which encode proteins that contribute to confer the properties described. Monocotyledons and dicotyledons may be used. Cell culturing techniques are known. See for instance, Inouye, supra. (Chap. 9). Seedlings may be suitable for treatment by cold-shock. Plants of particular interest include agricultural crops like maize (corn), the cereals (like wheat, rye, barley, etc.), rice, tobacco, coffee, tea and numerous others. Genetic engineering methods are described in Current Protocols, Unit 4. Reference to Genome Organization and Expression in Plants, Ed. Leaver, Plenum Press, 1980 and to Genetic Engineering of Plants, Ed. Kosuge et al., Plenum Press, 1982 may also be made for additional information.

The induction of cold-shock genes in plants and their transformation is of particular interest in that one is thus able to confer to the transformed plants the desirable property of thermo-tolerance and/or low temperature tolerance. This has of course major benefits in allowing the plants to grow over a wider or different climatic area and be more tolerant of temperature extremes.

The invention also covers such organisms which are transformed with expression vectors which contain genes or part thereof which encode the proteins of the invention. The organisms transformed or not, are capable of remaining viable under stress conditions under which they would not be normally were it not for the expression of the proteins encoded by the induced genes or the transformation of the organism. A group of organisms of particular present interest are eucaryotes, and amongst these, yeasts. A convenient source of suitable yeasts is found in the ATCC Catalogue of Yeasts, 18th Ed., 1990. Because of the practical and economic importance, the invention is particularly directed to the genus Saccharomyces which is extensively used in baking, beer, wine and other industries. Conventionally these yeasts are referred to as baker's brewer's and wine yeasts Amongst these, of special interest are the S. cerevisiae strains, the S. bayanus, S. carlsbergenensis, S. diastaticus, and S. uvarum, which lend themselves to transformation with the expression vectors of the invention. It will be noted that the AT CC Catalogue conveniently provides a list of Strains with Special Applications by listing the chemical produced. For instance, for alcohol production, the genus Candida, Clavispora, Dekkera, Hanseniaspora, Klockera, Kluyveromyces, Pschysalen, Saccharomyces, Schizosaccharomyces, Schwanniomyces, Torulolpsis, Yamadazyma, and Zygosaccharomyces are listed. This and other generally available information provides guidance to one skilled in the art in the practice of the invention.

For procaryotic bacterial strains, such are also publicly available and listed in ATCC Catalogue of Bacteria and Bacteriophages, 17th Edition, 1989.

It should be noted that the invention is not limited to production of these particular chemicals or products (like beer) but also includes other chemicals, drugs, antibiotics, etc. Likewise, the invention is not limited but includes procaryote and higher animal cell transformants.

Numerous valuable proteins are synthesized today by transformed microorganisms (eucaryotes and procaryotes). Strains over-expressing the proteins of the invention are envisaged which over-express the target protein under at lower and/or higher temperatures than conventionally carried out. The microorganism can be transformed with appropriate multi-cloning vectors or other appropriate vectors. Typical of physiologically active proteins include hGH, somastostatin, FSH, hCG, t-PA, insulin, interferon (alpha, beta, etc.), erythroprotein, and many others.

An advantage of the invention is that the hosts transformed with the genes of the invention can express the physiologically active proteins with less risks of decrease of activity that if grown and/or expressed at conventional temperatures.

In accordance with the invention, competent organism as described herein like eucaryotes or procaryotes are transformed with an endogenous promoter element for TIP1 or NOL1 (or homologous or functionally equivalent proteins) and a selected DNA sequence encoding a protein other than TIP1 or NOL1 (and other than a protein encoded by a yeast gene or part thereof which hybridizes to the TIP1 or NOL1 gene). Such a protein as mentioned above, may be any of the proteins that one skilled in the art wishes to express. It is to be noted that the protein need not be a physiologically active protein. But when expressed at low temperatures due to the tolerance of the organism of the invention, the protein may be obtained in a physiologically active condition.

DETAILED DESCRIPTION OF THE FIGURES

FIG. 1. Screening by Differential Colony Hybridization.

(A) Duplicated nitrocellulose filters containing the genomic DNA library were hybridized with $^{32}$P-labeled cDNA probes prepared from poly(A)$^+$ mRNA of 30° C. grown cells (left panel) or that of cold-shocked cells (at 10° C. for 2 hours) (right panel). The arrowheads indicate clones whose RNAs were more abundant in cold-shocked cells.

(B) Dot blot analysis of the differential expression of cloned genes. Two sets of the nylon membrane filters containing spots of purified plasmid DNA were hybridized with $^{32}$P-labeled cDNA probes prepared from poly(A)$^+$ mRNA of 30° C. grown cells or that of cold-shocked cells (at 10° C. for 2 hours). Left and the upper half of middle panels show clones whose expression were induced by cold-shock. Right panel shows clones whose expression were repressed by cold-shock. Plasmid pBR322, pKK77 for the ADH1 gene, pPGK2 for the PGK gene, and YRp7 for the TRP1 gene were used as controls.

FIG. 2. Restriction Maps and Sequencing Strategy for the TIP1 Gene. The upper portion of the Figure shows restriction maps of plasmids containing the TIP1 gene. Cross-hatched bars denote pBR322 derived sequences. The lower portion shows a restriction map of the sequenced region. The open bar indicates the longest open reading frame. The arrows above and below the bar represent positions and lengths of sequences determined with restriction sites where B is BglII; H, H1, H2, H3, respective HindIII sites; N is NdeI; P, P1, P2 and P3, respective PvuII; S is Sau3AI and X is XbaI.

FIG. 3. Regulation of Expression of the TIP1 Gene.

(A) Time course of induction of TIP1. Cells were cultured to mid-log phase (OD$_{600}$=2) in YPD at 30° C. and shifted to 10° C. Samples were collected for RNA extraction at 0 hour (lane 1), 1 hour (lane 2), 2 hours (lane 3), 4 hours (lane 4), 6 hours (lane 5), 8 hours (lane 6), 10 hours (lane 7) after the temperature shift.

(B) Expression of TIP1 at different growth phase. Cells were cultured in YPD at 30° C. Cultures were harvested in log phase (lanes 1, 2 at OD$_{600}$=2 and lanes 3, 4 at OD$_{600}$=4), early stationary phase (lane 5, 6 at OD$_{600}$=13), or late stationary phase (lanes 7, 8 at OD$_{600}$=22). A half of each culture was subjected to cold-shock (at 10° C. for 2 hours) (lanes 2, 4, 6, 8).

(C) Cells grown at 30° C. to mid-log phase (OD$_{600}$=2) (lane 1) were shifted to 5° C. (lane 2), 10° C. (lane 3), 15° C. (lane 4), or 21° C. (lane 5)and incubated for 2 hours, or shifted to 39° C. (lane 6), and incubated for 30 minutes.

(D) Cells were grown at 21° C. to mid-log phase (OD$_{600}$=2) (lane 1) and shifted to 10° C. (lane 2) or 15° C. (lane 3) and incubated for 2 hours.

(E) Cells were grown at 37° C. to mid-log phase (OD$_{600}$=2) (lane 1) and shifted to 10° C. (lane 2), 15° C. (lane 3), or 21° C. (lane 4) and incubated for 2 hours. All filters were reprobed with a ribosomal DNA clone demonstrating that equal amounts of RNA were present in each lane.

FIG. 4. Nucleotide and Deduced Amino Acid Sequence of the TIP1 Gene. The nucleotide +1 is the putative translation initiation site of TIP1. Putative TATA boxes and transcriptional terminator are underlined. The signal peptide like sequence at the N-terminal end and the hydrophobic sequence at the C-terminal end are underlined.

FIG. 5. Primer Extension Analysis of the TIP1 mRNA. Total RNA prepared from control cells (grown at 30° C.) (lane 1), cold-shocked cells (cultured at 10° C. for 2 hours after shifting from 30° C.) (lane 2), and heat-shocked cells (cultured at 39° C. for 30 minutes after shifting from 30° C.) (lane 3) were used as templates for each reaction. The products were analyzed on a 6% sequencing gel. The non-coding strand of the cloned TIP1 gene as sequenced by using the same oligonucleotide (lanes G, A, T, and C). The DNA sequence complementary to the readable sequence from the gel is shown on the right. The circles indicate the positions of the extension products in the cold-shocked sample.

FIG. 6. Southern Analysis of the TIP1 Gene. Yeast genomic DNA (1 μg) was cut with HindIII (lane 1), EcoRI (lane 2), DraI (lane 3), or BamHI (lane 4) and electrophoresed on a 0.8% agarose gel, and blotted to a nylon membrane. The filter was hybridized with a BamHI-Sau3AI fragment as probe (see results).

(A) The filter was washed in a low stringency condition (1×SSC, 0.2% SDS at 45° C.) after hybridization.

(B) The same filter was washed in a higher stringency condition (1×SSC, 0.2% SDS at 55° C.).

FIG. 7. Expression of the TIP1 Gene in Wild-Type, tip1$^-$ Mutant, or Strain over-expressing TIP1 Gene. The strains used were TD4 (wild-type) (lane 1, 2, 3), KNO52 (tip1$^-$) (lane 4, 5), and KY1 (TD4 carrying plasmid pYCA1) (lane 6, 7, 8). Cells were cultured to mid-log phase (1×10$^7$ cells/ml) at 30° C. in SD medium (lane 1, 4, 6) and subjected to cold-shock (at 10° C. for 2 hours) (lane 2, 5, 7), or cultured to mid-log phase at 34° C. in SD medium and subjected to heat-shock (at 38° C. for 30 minutes) (lane 3, 8).

FIG. 8. Effect of TIP1 Gene on Thermo-Tolerance. Cells were cultured to mid-log phase (1×10$^7$ cells/ml) at 24° C. Aliquots were incubated at 51° C. for the time indicated, after a 30 minute pre-heat at 38° C. (open symbols), or without a pre-treatment (solid symbols). Cell survival was determined at each time point by plating cells on YPD plates.

(A) TD4 (wild-type) (circles) or KNO52 (tip1⁻) (squares) cultured in SD medium.

(B) TD4 (wild-type) (circles) or KNO52 (tip1⁻) (squares) cultured in raffinose medium.

(C) KY10 (TD4 carrying plasmid YEp13) (circles) or KY1(TD4 carrying plasmid pYCA1) (triangles) cultured in SD medium.

FIG. 9. Sequence Comparison of TIP1 with SRP1. Vertical lines indicate identical amino acids. Dots indicate functionally identical amino acids. The tandem repetitive sequences in both proteins are underlined and numbered.

Figure 10:
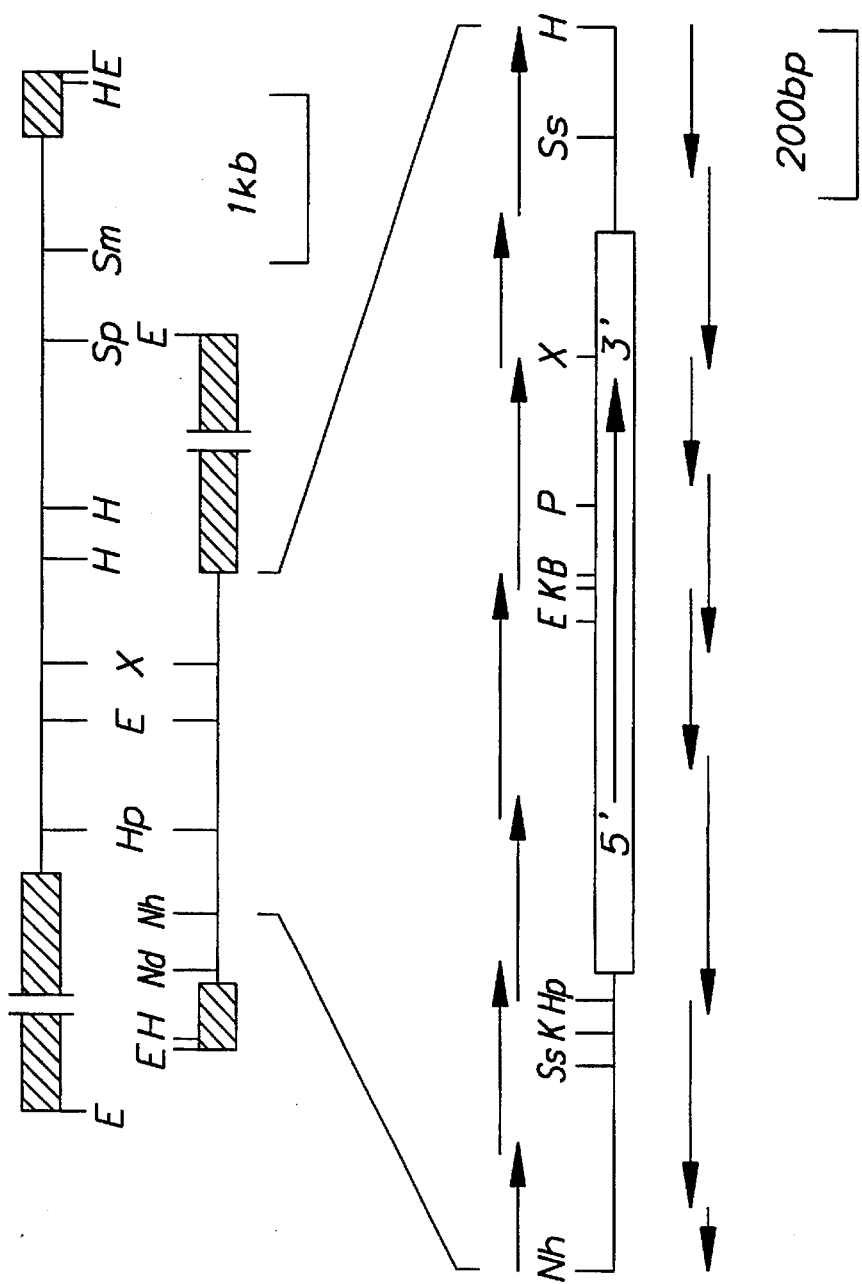
FIG. 10 shows restriction maps and sequencing strategy for NOL1.

FIG. 10. Restriction maps and sequencing strategy for the NOL1 gene.

The upper portion of the figure shows restriction maps of plasmids pDCS52 and pDCS84 containing the gene encoding the 1.6-kb transcript. Cross-hatched bars denote pBR322 derived sequences. The lower portion shows a restriction map of the sequenced region. The open bar indicates the longest open reading frame. The arrows above and below the bar graph represent positions and lengths of sequences determined with restriction sites where B is BglII, E is EcoRI, H is HindIII, Hp is HpaI, K is KpnI, Nh is NheI, Nd is NdeI, P is PvuII, Sm is SmaI, Ss is SspI, Sp is SphI and X is XbaI.

FIG. 11. Nucleotide and deduced amino acid sequence of the NOL1 gene.

The nucleotide +1 is the putative translation initiation site. Putative TATA boxes in the 5'-flanking region is underlined. Putative polyadenylation site (bold) and transcriptional terminator (underlined) in the 3'-flanking region are shown.

FIG. 12. Regulation of expression of the NOL1 gene.

(A) Time course of induction of NOL1. Cells were cultured to mid-log phase ($OD_{600}=2$) in YPD at 30° C. and shifted to 10° C. Samples were collected for RNA extraction at 0 hours (lane 1), 1 hour (lane 2), 2 hours (lane 3), 4 hours (lane 4), 6 hours (lane 5), 8 hours (lane 6), and 10 hours (lane 7) after the temperature shift.

(B) Expression of NOL1 at different growth phases. Cells were cultured in YPD at 30° C. Cultures were harvested in log phase (lane 1, 2 at $OD_{600}=2$ and lane 3, 4 at $OD_{600}=4$), early stationary phase (lane 5, 6 at $OD_{600}=13$), or late stationary phase (lane 7, 8 at $OD_{600}=22$). A half of each culture was subjected to cold-shock (at 10° C. for 2 hours) (lane 2, 4, 6, 8).

(C) Induction of the expression of NOL1 by various conditions of temperature shift. Cells were grown in YPD to mid-log phase ($OD_{600}=2$) at 21° C. (lane 1), 30° C. (lane 2), or 37° C. (lane 3). Various types of temperature shock were carried out with the cells grown to mid-log phase; temperature shift from 21° C. to 10° C. (lane 4)or 15° C. (lane 5), from 30° C. to 5° C. (lane 6), 10° C. (lane 7), 15° C. (lane 8), or 21° C. (lane 9), from 37° C. to 10° C. (lane 10), 15° C. (lane 11), or 21° C. (lane 12), or from 30° C. to 39° C. (lane 13). RNA samples were prepared from the cells 2 hours after the shift except for the shift from 30° to 39° C. (0.5 hours). All filters were reprobed with a ribosomal DNA clone to demonstrate that equal amounts of RNA were present in each lane.

FIG. 13. Hydropathy plot of the predicted NOL1 protein.

Relative hydrophilic values were calculated according to the method of Kyte and Doolittle (1982). Putative domains are numbered and borders are indicated by arrows. Hydrophilic portions are shown below the horizontal line.

FIG. 14. Sequence comparison of NOL1 and other protein.

(A) Comparison of the RNA-binding domains from yeast NOL1, human nucleolin (Srivastava et. al., 1989), yeast poly (A) binding protein (Sachs et al., 1986), and human U1 snRNP 70K (Theissen et al., 1986). Two consensus sequences (RNP1 and RNP2) are shown in bold type.

(B) Comparison of the C-terminal regions of NOL1 and human nucleolin. Vertical lines indicate identical amino acids. Dots indicate functionally identical amino acids. Two consensus sequences for RNA-binding domains (RNP1 and RNP2) are shown in bold type, and Gly-rich domains are underlined.

FIG. 15. Southern blot analysis of the NOL1 gene.

Yeast genomic DNA (1 μg) was cut with HindIII (lane 1), HindIII and HpaI (lane 2), DraI (lane 3), or BamHI (lane 4) and electrophoresed on a 0.8% agarose gel, and blotted to a nylon membrane. The filter was hybridized with the HpaI-HindIII fragment (see FIG. 1) as probe.

FIG. 16. Domain arrangement of the human nucleolin and NOL1.

FIG. 17. Amino acid sequence (1-210) of TIP1 protein.

FIG. 18. Amino acid sequence (1-414) of NOL1 protein.

FIG. 19. Nucleotide sequence containing the TIP1 gene (1-1584).

FIG. 20. Nucleotide sequence containing the NOL1 gene (1-2017).

Figure 21:
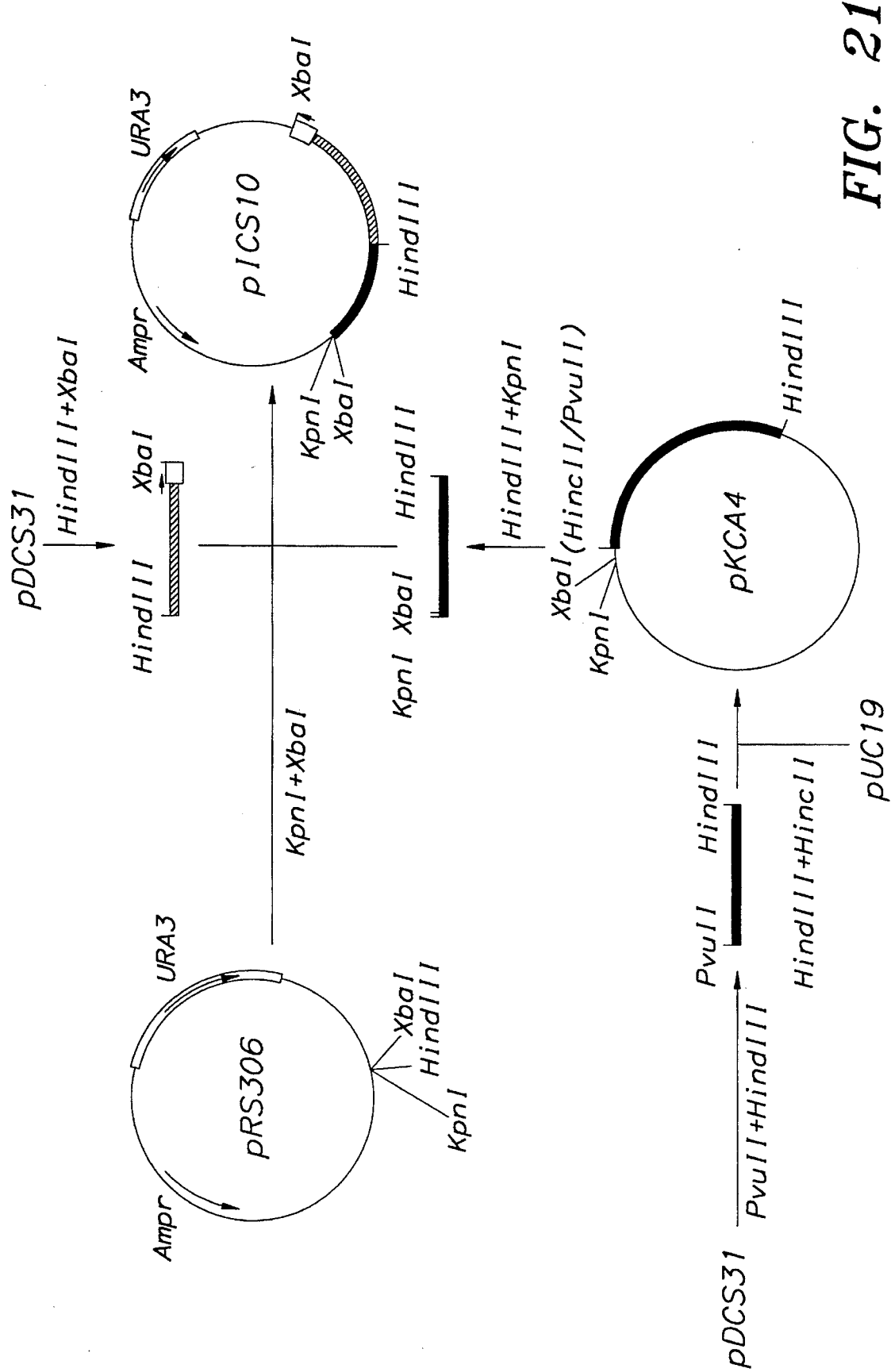
FIG. 21 shows the construction of plasmid pICS10.

FIG. 21 shows the strategy to construct plasmid pICS10.

Figure 22:
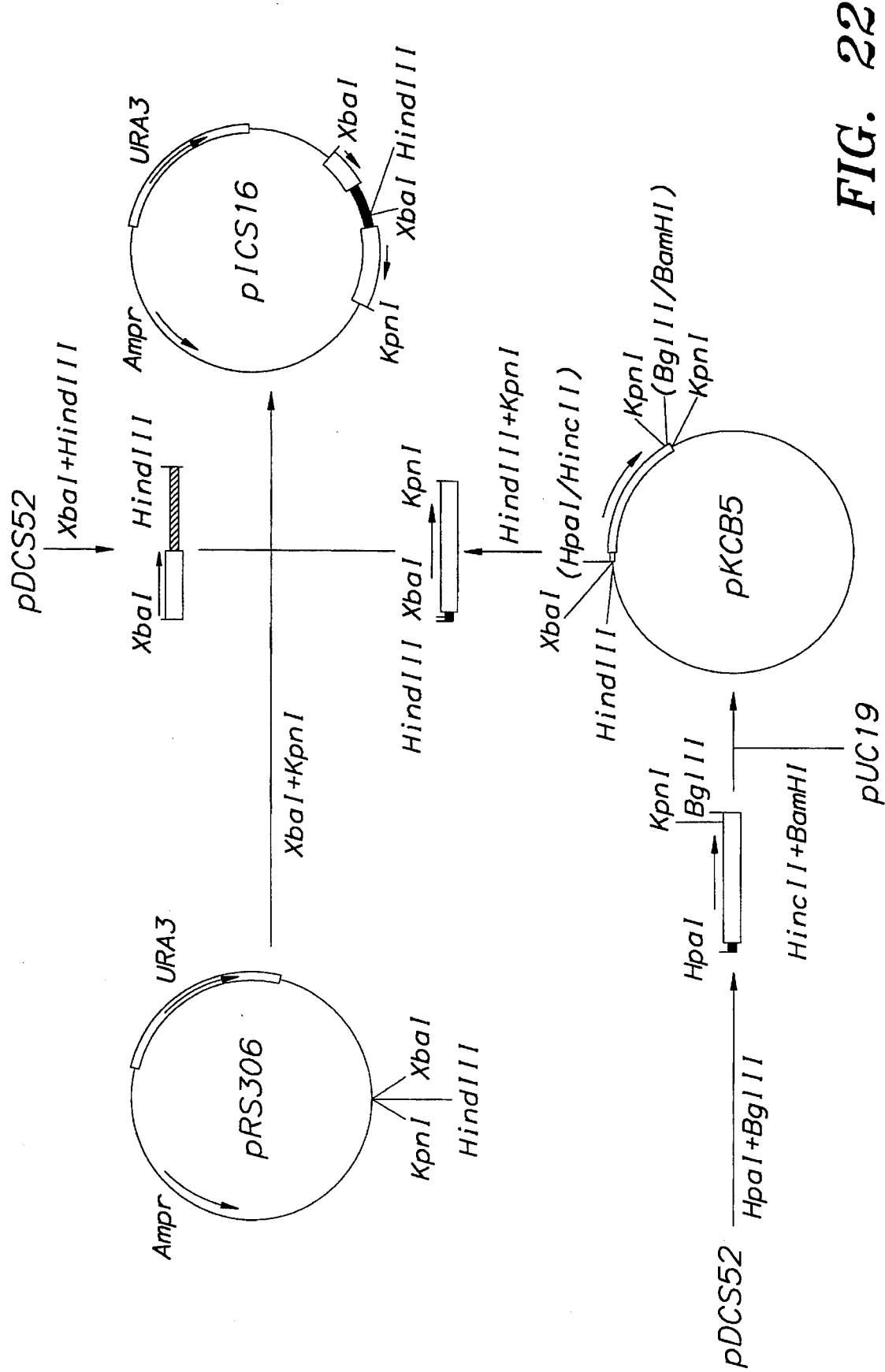
FIG. 22 shows the construction of plasmid pICS16.
Figure 24A:
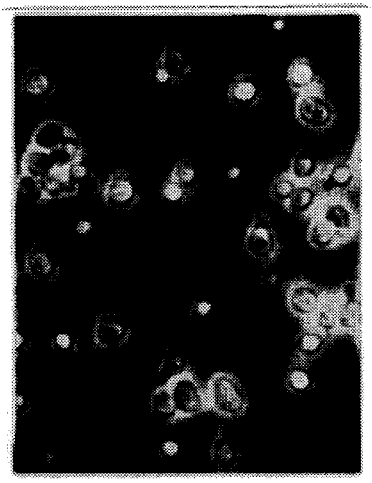
FIG. 24 shows microscopic examination of the cells.
Figure 24B:
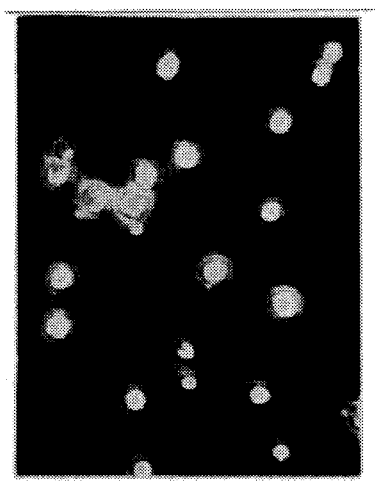
Figure 24C:
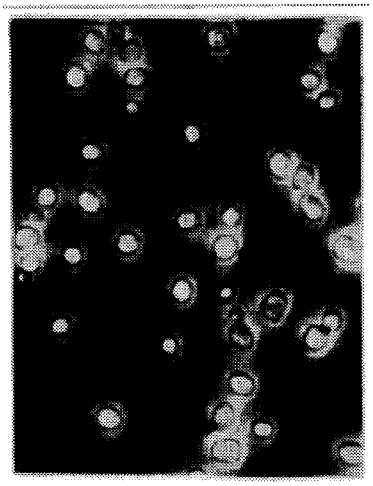
Figure 24D:

FIG. 22 shows the strategy to construct plasmid pICS16.

FIG. 23. Morphology of colonies grown on YPD plates at 30° C. or 38.5° C. Wild-type (TD4) (A, B) and tip1⁻ mutant (KNO52) (C, D) were plated on YPD plates and incubated at 30° C. (A, C) for two days or 38.5° C. (B, D) for three days.

FIG. 24. Phase-contrast microscopy of cells grown on YPD plates at 30° C. or 38.5° C. Wild-type (TD4) (A, B) and tip1 mutant (KNO52) (C, D) were plated on YPD plates and incubated at 30° C. (A, C) for two days or 38.5° C. (B, D) for three days. Cells were taken from colonies and separated from each other by brief sonication before taking pictures.

EXAMPLES AND EXPERIMENT PROCEDURES

Strains and Growth Conditions.

*S. cerevisiae*S288C (α mal gal2) was used for construction of a yeast genomic library and for studies of gene expression by Northern blotting. SP1 (a his3 ura3 trp1 leu2 ade8 gal2 can$^r$) and TD4 (a his4 ura3 trp1 leu2 can$^r$) were used as hosts for transformation.

Strains constructed in this study have following genotypes: KNO51 (a his3 ura3 trp1 leu2 ade8 gal2 can$^r$ tip1::URA3), KNO52 (a his4 ura3 trp1 leu2 can² tip1::URA3), KY1 (a his4 ura3 trp1 leu2 can$^r$ pYCA1), KY10 (a his4 ura3 trp1 leu2 can$^r$ YEp13) and KNO61 (a his3 ura3 trp1 leu2 ade8 gal2 can$^r$ nol1::URA3). Yeast culture media were prepared as described by Rose et al. (1990). YPD contained 1% Bacto-yeast-extract, 2% Bacto-peptone, and 2% glucose. SD contained 0.67% Difco yeast nitrogen base without amino acids and 2% glucose. Raffinose medium contained 0.67% Difco yeast nitrogen base without amino acids and 2% raffinose. Nutrients essential for auxotrophic strains were supplied at concentrations specified by Rose et al. (1990). Cells were grown at 30° C. unless otherwise indicated. For preparing RNA from heat- or cold-shocked cells, cells were grown to mid-log phase ($OD_{600}=1-2$ 1–2×10⁷ cells/ml) at certain temperatures and shifted to a desired temperature.

*Escherichia coli* strain DH5 (F⁻ endA1 recA1 hsdR17 ($r_k^-$, $m_k^+$) supE44^λ⁻ thi-1 gyrA relA1) was used as a host for genomic DNA library. CL83 (ara Δ(lac-proAB) rpsL φ80 lacZΔ M15 recA56) was used for plasmid construction.

Construction of Yeast Genomic DNA Library.

Total yeast DNA was prepared from mid-log phase S288C cells culture as described by Cryer et al. (1975). A partial Sau3AI DNA library was constructed as essentially described by Nasmyth and Reed (1980). The digested DNA fragments were size-fractionated by centrifugation in 5–20% sucrose gradients. Fractions contained DNA fragments from 1.5 to 4-kb were collected and used for ligation. pBR322 was used as a vector DNA after digested with BamHI and treated with bacterial alkaline phosphatase. 1.5 µg of DNA fragments were ligated with 1 µg of vector DNA using T4 DNA ligase. The ligation mixture was used to transform *E. coli* DH5. A library of 5×10⁴ was obtained, and 95% of these possessed inserts (determined by Amp$^r$Tet$^s$ phenotype). The colonies were scraped off from the plates, suspended in L broth medium containing 50 µg/ml ampicillin and 15% glycerol.

Preparation of Total RNA and Poly(A)⁺ mRNA.

Total RNA was prepared from yeast as follows: Cells were suspended in 1/40 volume of the cold extraction buffer (0.1M Tris, 0.1M LiCl, 0.1 mM EDTA, pH 7.4). Glass beads were added to meniscus and the suspension was vortexed for total of 1 minute in 15 second burst with 30 second intervals. After addition of 1/20 volume of 10% SDS and an equal volume of phenol-chloroform, the suspension was blended for 10 seconds on a vortex mixer and transferred to new tubes. After centrifugation, the aqueous phase was re-extracted with phenol-chloroform. RNA was precipitated by addition of 2.5 volumes of ethanol. The pellet was washed with 70% ethanol and dissolved in TE (10 mM Tris, 1 mM EDTA pH 7.5), poly(A)⁺ mRNA was purified by oligo(dT) cellulose (Pharmacia) column chromatography.

Preparation of ³²P-labeled cDNA.

Radioactively labeled cDNA was synthesized using 6 U of AMV-reverse transcriptase (Bethesda Research Laboratories) in a 20 µl reaction containing 100 mM Tris-HCl (pH 8.3), 50 mM KCl, 10 mM DTT, 10 mM MgCl₂, 500 mM dATP, TTP, dGTP, 50 µM dCTP, 10 µCi of [α-³²P]dCTP (3000 Ci/mmol; Amersham), 0.5 µg oligo-dT$_{12-18}$, 4 mM Na phosphate, 10 U of human placental RNase inhibitor (Bethesda Research Laboratories), and 2 µg of poly(A)⁺ mRNA. After 1 hour of incubation at 37° C., NaOH and EDTA were added to a final concentration of 0.15N and 10 mM, respectively. After hydrolysis of the RNA at 95° C. for 10 minutes, the mixture was neutralized with HCl and extracted with phenol-chloroform. The cDNA was precipitated with ethanol in the presence of 2.5M ammonium acetate and 5 µg of *E. coli* tRNA. Total incorporation was measured by trichloracetic acid precipitation of radioactive material onto Whatman GFC filters.

Differential Hybridization Screen.

Colony hybridization was performed essentially as described (Sambrook et al., 1989). Approximately 6000 transformants were placed onto each nitrocellulose filter (132 mm, 0.45-µm pore size, Schleicher & Schuell) placed on agar plates. A duplicate set of replica filters was taken from each dish and placed on agar plates. After colonies became visible, colonies were lysed. The filters were pre-hybridized in a solution containing 6× SSPE (1× SSPE is 0.15M NaCl, 1 mM EDTA, 10 mM sodium phosphate, pH 7.4), 5× Denhaldt's solution (1× Denhaldt's solution is 0.2% Ficoll, 0.2% polyvinylpyrolidone, 0.2% bovine serum albumin), 0.2% SDS, 2 µg/ml of poly(A) RNA, and 50 µg of denatured salmon sperm DNA for 2 hours at 65° C. Hybridization was carried out in the same solution with cDNA probe (1.3–1.6×10⁸ cpm/µg) at 65° C. One replica was hybridized with the cDNA probe prepared from the poly(A)⁺ mRNA of cells cultured at 30° C. and the other with that from cells cultured at 10° C. for 2 hours after shifting temperature from 30° C. After 20 hours, filters were washed twice for 1 hour each in 1× SSC (1× SSC is 0.15M NaCl, 0.015M sodium citrate, pH 7.0), 0.1% SDS at 65° C. and subjected to autoradiography.

The clones that were obtained from the first screen were patched onto nitrocellulose filters placed on agar plates. Two replica filters were made from each master filter and the filters were hybridized with each cDNA probe. The screening procedure was same as described above.

Dot Blot Analysis.

1 µg of purified plasmid DNA was spotted onto a nylon filter (Biotrans nylon membrane ICN Biomedical). The spotted DNA was denatured and fixed to the filter according to the instruction of the supplier. The filters were hybridized with cDNA probes and washed as described above.

Southern and Northern Blot Analysis.

Total RNA (10 µg) was electrophoresed on a 1.3% agarose gel containing 0.02M MOPS (pH 7.0), 5 mM sodium acetate, 1 mM EDTA, 0.66M formaldehyde and blotted to a nylon filter (Biotrans nylon membrane ICN Biomedical) in 10× SSC according to described method (Thomas, 1980). DNA samples (1 µg) were subjected to electrophoresis on an agarose gel, and blotted to a nylon filter (Biotrans nylon membrane ICN Biomedical) according to Southern (1975), except 3M sodium acetate (pH 5.5) was used as a neutralization buffer. ³²P-labeled probe was prepared using random priming labeling kit (Bethesda Research Laboratories). Hybridization and washing conditions were as described above except poly(A) RNA was omitted in solution.

To study of existence homologous genes in yeast genome, hybridization and washing conditions were changed as follows: pre-hybridization and hybridization were performed at 60° C. The filter was washed under a low stringency condition (1× SSC, 0.2% SDS at room temperature). Then, the filter was washed under conditions with increasing stringencies (1× SSC, 0.2% SDS at 40° C., 45° C., 50° C., 55° C., and 60° C.). The filter was subjected to autoradiography after each wash.

DNA Sequencing.

Restriction fragments were sub-cloned into a plasmid pUC19. The denatured plasmid DNA was sequenced by the dideoxynucleotide method (Sanger et al., 1977) by using Sequenase (U.S. Biochemical Corp.) according to the instructions of the supplier.

Primer Extension.

The primer extension analysis were performed as follows: 20-base synthetic oligonucleotide (10 pmol) complementary to the sequence from residue 23 to 42 of the coding strand, was labeled with ³²P by using 5 U of T4 polynucleotide kinase and 40 µCi of [γ-³²P]ATP in 10 µl of kinase buffer [70 mM Tris (pH 7.0), 10 mM MgCl₂ 5 mM DTT] at 37° C. for 1 hour. To the 2 µl of the reaction mixture, 20 µg of total RNA (5 µl) and 2M KCl (1 µl) and 20 mM EDTA (2 µl) were added. The mixture was denatured at 90° C. for 5 minutes and annealed at 45° C. for 1 hour. To the annealed RNA templates, 20 µl of reverse transcription reaction buffer (150 mM Tris (pH 8.3), 15 mM MgCl₂, 15 mM DTT, 750 µl dNTPs, 75 µg/ml of Actinomycin D, 20 U of placental RNase inhibitor (Bethesda Research Laboratories), and 25 U of AMV reverse transcriptase (Boehringer Mannheim) were added and the mixture was incubated at 37° C. for 1 hour. Reactions were stopped by adding 1 µl of 0.25M EDTA and the samples were precipitated with ethanol in the presence of 2.5M ammonium acetate and 1 µg of glycogen (Boehringer Mannheim). After suspending in 38% formamide, 8 mM EDTA, and 0.2% Bromophenol Blue, samples were loaded onto a 6% sequencing gel. Sequencing reactions primed with the same oligonucleotide were used as markers.
Recombinant Plasmids.

(a) pICS10. The construction of plasmid pICS10 is carried out as follows (FIG. 21): The 1.1-kb PvuII-HindIII (P3-H3 in FIG. 2) fragment containing the 3'-flanking region was isolated from the plasmid pDCS31 (FIG. 2), and ligated between the Hind III and HincII sites of a plasmid pUC19. This fragment was isolated as a KpnI-HindIII fragment from the resulting plasmid pKCA4. On the other hand, the 1.2-kb Hind-III-XbaI (H2-X in FIG. 21) fragment containing the 5'-flanking region and a part of the TIP1 gene was isolated from the plasmid pDCS31 (FIG. 2). These 1.2-kb HindIII-XbaI fragment and 1.1-kb KpnI-HindIII fragment were ligated between the KpnI and XbaI sites of pSR306 (Sikorski and Hieter, 1989), creating the pICS10.

(b) pICS16. The construction of plasmid pICS16 is carried out as follows (FIG. 22): The 0.7-kb HpaI-BglII fragment containing a part of the ORF and 5'-flanking region was isolated from the plasmid pDCS52 (FIG. 10), and ligated between the HincII and BamHI sites of plasmid pUC19, creating the plasmid pKCB5. This 0.7-kb fragment was isolated as a HindIII-KpnI fragment from the plasmid pKCB5. On the other hand, the 0.5-kb XbaI-HindIII fragment containing the 3'-flanking region and a part of the ORF, which was isolated from the plasmid pDCS52 (FIG. 10). These 0.7-kb HindIII-KpnI fragment and 0.5-kb XbaI-HindIII fragment were ligated between the KpnI and XbaI sites of the plasmid pRS306 (Sikorski and Hieter, 1989) to create the pICS16.

(c) pYCA1. For high level of expression of TIP1, the 3-kb HindIII fragment (H2-H3 in FIG. 2) containing TIP1 gene was inserted into the HindIII site of vector YEp13 (Broach et al., 1979) to form plasmid pYCA1. Transformation was carried out by the method of Ito et al. (1983).

Plasmid YEp13 is a suitable vector in conjunction with transformation in yeast for isolating specific yeast genes. The plasmid consists of pBR322, the LEU2 gene of yeast, and a DNA fragment containing a yeast origin of replication from 2µ circle. It has been demonstrated that this fragment promotes the efficient replication in yeast of plasmids into which it has been inserted (Hicks et al., 1978).
Thermo-tolerance Experiments.

Cells were grown to mid-log phase ($1 \times 10^7$ cells/ml) in a SD medium or raffinose medium at 24° C. Portions of cultures were incubated for 30 minutes at 38° C. or 24° C. before exposing 51° C. 10–50 µl of the culture were transferred to a 1.5 ml Eppendoff tube and incubated at 51° C. for various times, and then put on ice. After appropriate dilutions, the cultures were placed onto YPD plates, and plates were incubated at 30° C. for 2 days.

This invention is intended and does include within its scope as contemplated by the doctrine of equivalents, the use of substantially the same means to achieve substantially the same results, in substantially the same way as claimed.

REFERENCES

Ammerer, G., *Methods in Enzymology* (ed. R. Wu et al.), Vol. 101 p. 192 Academic Press (1983).

ATCC Catalogue of Bacteria and Bacteriophages, 17th Edition, 1989.

ATCC Catalogue of Yeasts, 18th Ed., 1990.

Beggs, J. D., *Genetic Engineering* (ed. R. Williamson) Vol. 2 p. 175, Academic Press (1982).

Beltz et al., *Method in Enzymology*, Vol. 100, p. 266 (198 ).

Beltz, Gerald A. et al. *Methods in Enzymology*, Vol. 100, "Recombinant DNA (Part B)", edited by Ray, W. et al., Academic Press, Inc., Section 19, "Isolation of Multigene Families and Determination of Homologies by Filter Hybridization Methods" page 266 and seq.

Bennetzen, J. L. and Hall, H. D. (1982), "Codon selection in yeast", *J Biol. Chem.*, 257, 3026–3031.

Bitter et al. (1984), *Gene*, 32, 263.

Bitter et al. (1984), *Proc. Natl. Acad. Sc. U.S.A.*, 81, 5330.

Borkovich, K. A. et al. (1989), "hsp82 is an essential protein that is required in higher concentrations for growth of cells at higher temperature", *Mol. Cell Biol.*, 9, 3919–3930.

Botstein, D. et al., *Gene*, 8, 17 (1979).

Bouche, G. et al. (1984), "Interrelations between the maturation of a 100 kDa nucleolar protein and pre rRNA synthesis in CHO cells", *Nucleic Acids Res.*, 12, 3025–3035.

Broach et al. (1983), "Vectors of High-Level, Inducible Expression of Cloned Genes in Yeast", *Experimental Manipulation of Gene Expression*, Chapter 5, Academic Press, Inc.

Broach, J. R. et al. (1979), "Transformation in yeast: development of a hybrid cloning vector and isolation of the CAN1 gene", *Gene*, 8, 121–133.

Caizergues-Ferrer et al. (1987), *Biochemistry*, 26, 7876–7883.

Caizergues-Ferrer, M. et al. (1989), "Nucleolin from *Xenopus laevis*: cDNA cloning and expression during development", *Genes and Dev.*, 3, 324–333.

Craig, E. and Jacobsen, K. (1984), "Mutations of the heat inducible 70 kilodalton genes of yeast confer temperature sensitive growth", *Cell*, 38, 841–849.

Cryer, D. R. et al (1975), "Isolation of yeast DNA", *Methods Cell Biol.*, 12, 39–44.

*Current Protocols in Molecular Biology*, Chapter 17, Vols. 1 and 2, editor Ausubell et al., publisher Green Publishing Associates and Wiley Interscience.

Current Protocols, Sections 2.9.1, 2.9.10, and 6.3.1–6.3.5.

Current Protocols, Vol. 2, Sections 13.4.1, 13.4.2 (1989).

Duffoud, G. D. et al. (1985), "Structure and function of the signal peptide", *Current Topics in Membrane and Transport*, 24, 65–104.

Experimental Manipulation of Gene Expression, Ed. Masayori Inouye, Academic Press, (1983).

Finley, D. et al. (1987), "The yeast polyubiquitin gene is essential for resistance to high temperatures, starvation, and other stresses", *Cell*, 48, 1035–1046.

Fornaugh, K. L. and Loomis, W. F. (1989), "Sequence of the *Dictyostelium discoideum* spore coat gene SP96", *Nucleic Acid Res.*, 17, 9489.

Genetic Engineering of Plants, editors Kosuge et al., Basic Life Sciences, 1983.

Goff et al. (1984), *Gene*, 27, 35.

Hereford, L. and Rosbash, M. (1977), "Number and distribution of polyadenylated RNA sequence in yeast", *Cell*, 10, 453–462.

Goldstein et al. (1990), "Major cold shock protein of *Escherichia coli*", *Proc. Natl. Acad. Sci. USA*, 87, 283–287.

Grossman, A. D. et al., 1987.

Hamilton, R. et al. (1987), "Compilation and comparison of the sequence context around the AUG start codons in *Saccharomyces cerevisiae* mRNA", *Nucl. Acid. Res.*, 15, 3581–3593.

Hicks et al. (1978).

Hitzeman et al. (1981), *Nature (London)*, 293, 717.

Ito, H. et al. (1983), "Transformation of intact yeast cells treated with alkali cations," *J. Bacteriol.*, 153, 163–168.

Jones, P. G. et al. (1987) "Induction of protein in response to low temperature in *Escherichia coli*", *J. Bacteriol.*, 169, 2029–2095.

Kyte, A. M. and Doolittle, F. (1982) "A simple method for displaying the hydrophobic character of a protein", *J. Mol. Biol.*, 157, 132–150.

Lindquist, S. and Craig, E. A. (1988), "The heat shock proteins", *Annu. Rev. Genet.*, 22, 631–677.

Maniak, M. and Nellen, W. (1988), "A developmentally regulated membrane gene in *Dictyostelium discoideum* is also induced by heat shock and cold shock", *Mol. Cell. Biol.*, 8, 153–159.

Marguet, D. and Lauquin, G. J.-M. (1986) "The yeast srp gene: positive modulation by glucose of its transcription expression", *Biochem. Biophys. Res. Commum.*, 138, 297–303.

Marguet, D. et al. (1988), "Yeast gene SRP1 (Seine rich protein) Intragenic repeat structure and identification of a family of SRP1-related DNA sequences", *J. Mol. Biol.*, 202, 455–470.

*Methods in Enzymology*, Vol. 153 (1987), "Expression and Secretion Vectors For Yeasts" in Academic Press, Inc.

Müller-Taubenberger, A. et al. (1988), "Ubiquitin gene expression in Dictyostelium is induced by heat and cold shock, cadmium, and inhibition of protein synthesis", *J. Cell. Sci.*, 90, 51–58.

Miyanohora et al. (1983), *Proc. Natl. Acad. Sci. U.S.A.*, 80, 1.

Nasmyth, K. A. and Reed, S. I. (1980), *Proc. Natl. Acad. Sci. U.S.A*, 77, 2119–2123.

Neidhardt, F. C. et al. (1984) "The genetics and regulation of heat-shock proteins", *Ann. Rev. Genet.*, 18, 295–329.

Nicolet, C. M. and Craig, E. A. (1989), "Isolation and characterization of STI1, a stress inducible gene from *Saccharomyces cerevisiae*", *Mol. Cell Biol.*, 3638–3646.

Pearson and Lipman (1988), "Improved tools for biological sequence comparison", *Proc. Natl. Acad. Sci. U.S.A.*, 85, 2444–2448.

Pelham, H. R. B. (1989), "Heat shock and the sorting of luminal ER proteins", *EMBO J.*, 8, 3171–3176.

Perbal, Bernard (1988), *A Practical Guide To Molecular Cloning*, Second Edition, John Wiley & Sons.

Petko, L. and Lindquist, S. (1986), "Hsp26 is not required for growth at high temperatures, nor for thermotolerance, spore development, or germination", *Cell*, 45, 885–894.

Rose, M. D. et al. (1990), "Method in yeast genetics: A Laboratory Course Manual", (Cold Spring Harbor, New York: Cold Spring Harbor Laboratory).

Sachs, A. B. et al. (1986), "A single gene from yeast for both nuclear and cytoplasmic polyadenylate-binding proteins: Domain structure and expression", *Cell*, 45, 827–835.

Sambrook, J. et al. (1990), "Molecular Cloning, A Laboratory Manual", (Cold Spring Harbor, N.Y.: Cold Harbor Laboratory).

Sanchez, Y. and Lindquist, S. L. (1990), "HSP104 required for induced thermo-tolerance", *Science*, 248, 1112–1115.

Sanger, F. et al. (1977), "DNA sequencing with chain-terminating inhibitors", *Proc. Natl. Acad. Sci. U.S.A.*, 174, 5463–5467.

Schlesinger, M. J. (1990), "Heat shock proteins", *J. Biol. Chem.*, 265, 12111–12114.

Scopes, Robert K. (1987), *Protein Purification: Principles and Practice*, Springer Flag, N.Y.

Sikorski, R. S. and Hieter, P. (1989), "A system of shuttle vectors and yeast host strains designed for efficient manipulation of DNA in *Saccharomyces cerevisiae*", *Genetics*, 122, 19–27.

Southern, E. M. (1975), "Detection of specific sequences among DNA fragments separated by gel electrophoresis", *J. Mol. Biol.*, 98, 503–516.

Srivastava, M. et al. (1989), "Cloning and sequencing of the human nucleolin cDNA", *FEBS Lett.*, 25, 99–105.

Srivastava, M. et al. (1990), *JBC*, 265, 14922–1431.?

Struhl, K. (1989), "Molecular mechanisms of transcriptional regulation in yeast", *Annu. Rev. Biochem.*, 58, 1051–1077.

Strauss, D. B. et al., 1987.

Theissen, H. et al. (1986), "Cloning of the human cDNA for the U1 RNA-associated 70K protein", *EMBO J.*, 5, 3209–3217.

Thomas, P. S. (1980), "Hybridization of denatured RNA and small DNA fragments transferred to nitrocellulose", *Proc. Natl. Acad. Sci. U.S.A.*, 77, 5201–5205.

Tuite et al. (1982), *EMBO J.*, 1, 63.

Zaret, K. S. and Sherman, F. (1982), "DNA sequence required for efficient transcription termination in yeast", *Cell*, 28, 563–573.

Werner-Washburne, M. et al. (1987), "Complex interactions among members of an essential sub-family of hsp70 genes in *Saccharomyces cerevisiae*", *Mol. Cell Biol.*, 7, 2568–2577.

Werner-Washburne, M. et al. (1989), "Yeast HSP70 RNA levels vary in response to the physiological status of the cell", *J. Bacteriol.*, 171, 2680–2688.

Sanchez, Y. and Lindquist, S. L. (1990), "HSP104 required for induced thermo-tolerance", *Science*, 248, 1112–1115.

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
    ( A ) LENGTH: 1584 base pairs
    ( B ) TYPE: nucleic acid
    ( C ) STRANDEDNESS: double
    ( D ) TOPOLOGY: unknown ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
    ( A ) ORGANISM: Saccharomyces cerevisiae
    ( B ) STRAIN: S288C ( i x ) FEATURE:
    ( A ) NAME/KEY: CDS
    ( B ) LOCATION: 475..1104

( i x ) FEATURE:
    ( A ) NAME/KEY: misc_feature
    ( B ) LOCATION: 1
    ( D ) OTHER INFORMATION: /note="Base #
        corresponds to base –474 of the sequence listed in
        Figure 4 of the application"

( x i ) SEQUENCE DESCRIPTION: SEQ ID NO:1:

```
GATCTGGTTA  TGGTTTTTCT  TGACTATAAC  CTTAATTATG  AGACTAATGT  CTTCGGGAGG      60

TCCCTTTTCC  GATTTCCGA   CTCTTTTCCG  TTGAAGAATG  TACTTGTGGT  TTTGAATCCT     120

ACGGCAGTTA  TTGCGGCGGT  TTGGCCCTTT  CTTTCAAAGA  TTGTGATGGA  AATAATTGAT     180

TGTTCCGGGA  AATGTGTCTT  ATTTTCTAAA  AGCATCTTTT  TTTCTCTCCA  ATTCTTCGAG     240

CTATTTCCAG  TAAAGGAAAA  AAAAGGTTTG  CTGTAAGGGT  GAATATGTCT  CCAACCTCTT     300

TGAGGTACTG  CGTTGCTTCA  TTCACCATTT  AATATAAATA  GTACATTGGC  AGCCCTCTTT     360

CAAACGTCAA  TTATTCTCGC  TTGCCTAACT  TTGTTCGGAC  CGAAATTATA  AAGGCATTCA     420

ATCAGTAACA  ATAATTGCTA  TTGCATAACT  ATACCCTCTG  CTAAATAAAA  TAAA ATG       477
                                                                Met
                                                                 1
```

| TCC | GTT | TCC | AAG | ATT | GCT | TTC | GTT | TTA | AGT | GCC | ATT | GCC | TCT | TTG | GCC | 525 |
|---|---|---|---|---|---|---|---|---|---|---|---|---|---|---|---|---|
| Ser | Val | Ser | Lys | Ile | Ala | Phe | Val | Leu | Ser | Ala | Ile | Ala | Ser | Leu | Ala | |
| | | | 5 | | | | | 10 | | | | | 15 | | | |

| GTC | GCT | GAC | ACC | AGC | GCC | GCC | GAA | ACT | GCT | GAA | TTG | CAA | GCT | ATT | ATC | 573 |
|---|---|---|---|---|---|---|---|---|---|---|---|---|---|---|---|---|
| Val | Ala | Asp | Thr | Ser | Ala | Ala | Glu | Thr | Ala | Glu | Leu | Gln | Ala | Ile | Ile | |
| | | 20 | | | | | 25 | | | | | 30 | | | | |

| GGT | GAC | ATC | AAC | TCT | CAT | CTT | TCT | GAC | TAC | TTG | GGT | CTA | GAA | ACT | GGC | 621 |
|---|---|---|---|---|---|---|---|---|---|---|---|---|---|---|---|---|
| Gly | Asp | Ile | Asn | Ser | His | Leu | Ser | Asp | Tyr | Leu | Gly | Leu | Glu | Thr | Gly | |
| | | 35 | | | | 40 | | | | | 45 | | | | | |

| AAC | AGT | GGA | TTC | CAA | ATT | CCA | TCT | GAT | GTC | TTG | AGT | GTG | TAT | CAA | CAA | 669 |
|---|---|---|---|---|---|---|---|---|---|---|---|---|---|---|---|---|
| Asn | Ser | Gly | Phe | Gln | Ile | Pro | Ser | Asp | Val | Leu | Ser | Val | Tyr | Gln | Gln | |
| 50 | | | | | 55 | | | | | 60 | | | | | 65 | |

| GTC | ATG | ACT | TAC | ACC | GAT | GAC | GCT | TAC | ACT | ACC | TTG | TTT | AGT | GAA | TTG | 717 |
|---|---|---|---|---|---|---|---|---|---|---|---|---|---|---|---|---|
| Val | Met | Thr | Tyr | Thr | Asp | Asp | Ala | Tyr | Thr | Thr | Leu | Phe | Ser | Glu | Leu | |
| | | | | 70 | | | | | 75 | | | | | 80 | | |

| GAC | TTT | GAT | GCT | ATC | ACT | AAG | ACA | ATT | GTT | AAA | TTG | CCA | TGG | TAC | ACC | 765 |
|---|---|---|---|---|---|---|---|---|---|---|---|---|---|---|---|---|
| Asp | Phe | Asp | Ala | Ile | Thr | Lys | Thr | Ile | Val | Lys | Leu | Pro | Trp | Tyr | Thr | |
| | | | | 85 | | | | | 90 | | | | | 95 | | |

| ACA | AGA | TTG | AGT | TCT | GAA | ATC | GCT | GCT | GCT | CTT | GCC | TCC | GTT | TCC | CCA | 813 |
|---|---|---|---|---|---|---|---|---|---|---|---|---|---|---|---|---|
| Thr | Arg | Leu | Ser | Ser | Glu | Ile | Ala | Ala | Ala | Leu | Ala | Ser | Val | Ser | Pro | |
| | | | 100 | | | | | 105 | | | | | 110 | | | |

| GCT | TCT | TCC | GAG | GCT | GCA | TCT | TCT | TCC | GAG | GCT | GCA | TCT | TCT | TCC | AAG | 861 |
|---|---|---|---|---|---|---|---|---|---|---|---|---|---|---|---|---|
| Ala | Ser | Ser | Glu | Ala | Ala | Ser | Ser | Ser | Glu | Ala | Ala | Ser | Ser | Ser | Lys | |

-continued

| | | | | | | | | | | | | | | | |
|---|---|---|---|---|---|---|---|---|---|---|---|---|---|---|---|
| | | 115 | | | | | 120 | | | | | 125 | | | |
| GCT | GCA | TCT | TCT | TCC | GAA | GCT | ACA | TCC | TCT | GCC | GCT | CCA | TCC | TCT | TCT | 909
| Ala | Ala | Ser | Ser | Ser | Glu | Ala | Thr | Ser | Ser | Ala | Ala | Pro | Ser | Ser | Ser |
| 130 | | | | | 135 | | | | | 140 | | | | | 145 |

```
GCT GCC CCA TCT TCT TCT GCT GCC CCA TCA TCA TCT GCC GAA TCA TCT      957
Ala Ala Pro Ser Ser Ser Ala Ala Pro Ser Ser Ser Ala Glu Ser Ser
            150                 155                 160

TCT AAG GCC GTT TCT TCT TCT GTC GCT CCA ACT ACC TCT TCT GTC AGC     1005
Ser Lys Ala Val Ser Ser Ser Val Ala Pro Thr Thr Ser Ser Val Ser
            165                 170                 175

ACT TCT ACA GTC GAA ACT GCT TCC AAT GCC GGT CAA AGA GTC AAT GCA     1053
Thr Ser Thr Val Glu Thr Ala Ser Asn Ala Gly Gln Arg Val Asn Ala
            180                 185                 190

GGC GCT GCC TCT TTC GGT GCT GTT GTT GCA GGT GCA GCT GCT TTA TTG     1101
Gly Ala Ala Ser Phe Gly Ala Val Val Ala Gly Ala Ala Ala Leu Leu
    195                 200                 205

TTA TAAAAGGGAA CCTTTTACAA CAAATATTTG AAAAATTACC TCCATTATTA          1154
Leu
210

TACCTTCTCT TTATGTAATT GTTAGTTCGA AAATTTTTC TTCATTAATA TAATCAACTT    1214

CTAAAACTTT CTAAAAACGT TCTCTTTTTC GAGATTAGTG CTTCTTCCCA ATCCGTAAGA   1274

AATGTTTCCT TTCTTGACAA TTGGCACCAG CTGGCTACTC GTTGCTGCAA AACTACTCTC   1334

TTTTATTTTT AATTTACGAA CGATTATCTT TCGAAGGAAC GACCAAACGA GCTAAATATG   1394

GGCATCGCCA ACGTTAAAAA AATGGACCCT ACCGAAGACG TTATTATGCC AAGGCGCAGC   1454

GAAGAGTCTT TCTCCTTGAG AAAAAATATG CATGAAACAA AATAGACAGG ACCAGACCCT   1514

CTTCGGGAAA AAAGTCAAG ATTTAACACG TGGCTACACC GGCTGGCTTA CAACCAACCA    1574

ACATAAGATC                                                          1584
```

( 2 ) INFORMATION FOR SEQ ID NO:2:

( i ) SEQUENCE CHARACTERISTICS:
        ( A ) LENGTH: 210 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ser Val Ser Lys Ile Ala Phe Val Leu Ser Ala Ile Ala Ser Leu
 1               5                  10                  15

Ala Val Ala Asp Thr Ser Ala Ala Glu Thr Ala Glu Leu Gln Ala Ile
            20                  25                  30

Ile Gly Asp Ile Asn Ser His Leu Ser Asp Tyr Leu Gly Leu Glu Thr
        35                  40                  45

Gly Asn Ser Gly Phe Gln Ile Pro Ser Asp Val Leu Ser Val Tyr Gln
    50                  55                  60

Gln Val Met Thr Tyr Thr Asp Asp Ala Tyr Thr Thr Leu Phe Ser Glu
65                  70                  75                  80

Leu Asp Phe Asp Ala Ile Thr Lys Thr Ile Val Lys Leu Pro Trp Tyr
                85                  90                  95

Thr Thr Arg Leu Ser Ser Glu Ile Ala Ala Ala Leu Ala Ser Val Ser
            100                 105                 110

Pro Ala Ser Ser Glu Ala Ala Ser Ser Ser Glu Ala Ala Ser Ser Ser
            115                 120                 125

Lys Ala Ala Ser Ser Ser Glu Ala Thr Ser Ser Ala Ala Pro Ser Ser
```

|  | | | | 130 | | | | | 135 | | | | | 140 | |

Ser Ala Ala Pro Ser Ser Ser Ala Ala Pro Ser Ser Ser Ala Glu Ser
145               150               155               160

Ser Ser Lys Ala Val Ser Ser Ser Val Ala Pro Thr Thr Ser Ser Val
            165               170               175

Ser Thr Ser Thr Val Glu Thr Ala Ser Asn Ala Gly Gln Arg Val Asn
        180               185               190

Ala Gly Ala Ala Ser Phe Gly Ala Val Val Ala Gly Ala Ala Ala Leu
        195               200               205

Leu Leu
    210

( 2 ) INFORMATION FOR SEQ ID NO:3:

( i ) SEQUENCE CHARACTERISTICS:
        ( A ) LENGTH: 2017 base pairs
        ( B ) TYPE: nucleic acid
        ( C ) STRANDEDNESS: double
        ( D ) TOPOLOGY: unknown ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Saccharomyces cerevisiae
        ( B ) STRAIN: S288C ( i x ) FEATURE:
        ( A ) NAME/KEY: CDS
        ( B ) LOCATION: 484..1725

( i x ) FEATURE:
        ( A ) NAME/KEY: misc_feature
        ( B ) LOCATION: 1
        ( D ) OTHER INFORMATION: /note="Base #
        corresponds to base -483 of the sequence listed in
        Figure 11 of the application"

( x i ) SEQUENCE DESCRIPTION: SEQ ID NO:3:

```
GCTAGCTATT  TAAACCCCAT  CACGTTGATT  GTCTATTTCG  CTATAGGTTA  TTTTGCCAAG      60

AAAACTTACT  GGGCAATACT  TACATCCATT  CAGATTTTTG  GATAAAGCAA  TTGAAGAAAG     120

ACGACAGCAA  TTCGACTGGT  GGTTGTTAAT  TACCCTTTGA  TCCTCTGATT  TAAAGACGTA     180

ATCCTTCCTG  GGGGTAAGTG  CCTGATGTAT  GGGTCCCCAT  GCCCTTTTTT  TTCGTTTCTT     240

TTTTCACTCC  ATTTCTTTTT  TTTTTTTTTT  TTTTGGTGAA  AAATTTGCAA  GGGCAGCTCA     300

TCGCAAGAAC  GAAAATTTTC  AATCCAATAT  TAAAAGTACT  TAAGTGTAGC  TGTTGCTGTC     360

TGCACTTCCC  AATCCATTGG  TACCTTAAGT  TATTTCCTTT  CGTAGTATTT  TTCTTACTTT     420

TGCTTCCCAA  AGACGAACTG  TTAACCAATT  TCGGATCACT  CAACCCAGGC  AGGATAAAAT     480
```

AAG ATG GCT AAG ACT ACT AAA GTA AAA GGT AAC AAG AAG GAA GTT AAG    528
    Met Ala Lys Thr Thr Lys Val Lys Gly Asn Lys Lys Glu Val Lys
    1               5                   10                  15

GCT TCC AAA CAA GCC AAA GAA GAA AAA GCT AAG GCC GTC TCT TCC TCT    576
Ala Ser Lys Gln Ala Lys Glu Glu Lys Ala Lys Ala Val Ser Ser Ser
                20                  25                  30

TCC TCC GAA TCT TCA TCC TCA TCT TCA TCT TCA TCT GAA TCT GAA TCT    624
Ser Ser Glu Ser Ser Ser Ser Ser Ser Ser Ser Ser Glu Ser Glu Ser
                35                  40                  45

| | | | | | | | | | | | | | | | | |
|---|---|---|---|---|---|---|---|---|---|---|---|---|---|---|---|---|
| GAG | TCT | GAG | TCT | GAA | TCT | GAA | TCT | TCA | TCT | TCA | TCT | TCA | TCC | TCT | GAT | 672 |
| Glu | Ser | Glu | Ser | Glu | Ser | Glu | Ser | Ser | Ser | Ser | Ser | Ser | Ser | Ser | Asp | |
| | | | 50 | | | | 55 | | | | | 60 | | | | |
| TCT | GAA | TCC | TCT | TCT | TCA | TCG | TCT | TCT | GAC | AGC | GAA | AGT | GAA | GCT | GAA | 720 |
| Ser | Glu | Ser | Ser | Ser | Ser | Ser | Ser | Ser | Asp | Ser | Glu | Ser | Glu | Ala | Glu | |
| | 65 | | | | | 70 | | | | | 75 | | | | | |
| ACC | AAG | AAG | GAA | GAA | TCC | AAG | GAT | TCC | TCT | TCC | TCT | TCC | TCT | GAC | TCT | 768 |
| Thr | Lys | Lys | Glu | Glu | Ser | Lys | Asp | Ser | Ser | Ser | Ser | Ser | Ser | Asp | Ser | |
| 80 | | | | | 85 | | | | | 90 | | | | | 95 | |
| TCT | TCC | GAC | GAA | GAA | GAA | GAA | GAA | GAA | AAA | GAA | GAA | ACC | AAG | AAG | GAA | 816 |
| Ser | Ser | Asp | Glu | Glu | Glu | Glu | Glu | Glu | Lys | Glu | Glu | Thr | Lys | Lys | Glu | |
| | | | | 100 | | | | | 105 | | | | | 110 | | |
| GAA | TCA | AAA | GAA | TCT | TCT | AGC | TCT | GAT | TCA | TCC | TCA | TCT | TCA | TCT | TCT | 864 |
| Glu | Ser | Lys | Glu | Ser | Ser | Ser | Ser | Asp | Ser | Ser | Ser | Ser | Ser | Ser | Ser | |
| | | 115 | | | | | 120 | | | | | 125 | | | | |
| GAT | AGC | GAA | AGC | GAA | AAG | GAA | GAG | TCT | AAC | GAT | AAG | AAA | CGT | AAA | TCT | 912 |
| Asp | Ser | Glu | Ser | Glu | Lys | Glu | Glu | Ser | Asn | Asp | Lys | Lys | Arg | Lys | Ser | |
| | | 130 | | | | | 135 | | | | | 140 | | | | |
| GAG | GAC | GCC | GAA | GAA | GAA | GAA | GAC | GAA | GAG | TCT | TCC | AAC | AAG | AAG | CAA | 960 |
| Glu | Asp | Ala | Glu | Glu | Glu | Glu | Asp | Glu | Glu | Ser | Ser | Asn | Lys | Lys | Gln | |
| 145 | | | | | 150 | | | | | 155 | | | | | | |
| AAA | AAT | GAA | GAA | ACC | GAA | GAA | CCA | GCT | ACT | ATT | TTC | GTT | GGT | AGA | CTA | 1008 |
| Lys | Asn | Glu | Glu | Thr | Glu | Glu | Pro | Ala | Thr | Ile | Phe | Val | Gly | Arg | Leu | |
| 160 | | | | | 165 | | | | | 170 | | | | | 175 | |
| TCG | TGG | TCT | ATT | GAT | GAC | GAA | TGG | TTG | AAG | AAG | GAA | TTC | GAA | CAC | ATC | 1056 |
| Ser | Trp | Ser | Ile | Asp | Asp | Glu | Trp | Leu | Lys | Lys | Glu | Phe | Glu | His | Ile | |
| | | | | 180 | | | | | 185 | | | | | 190 | | |
| GGT | GGT | GTC | ATT | GGT | GCC | AGA | GTT | ATT | TAT | GAA | AGA | GGT | ACC | GAT | AGA | 1104 |
| Gly | Gly | Val | Ile | Gly | Ala | Arg | Val | Ile | Tyr | Glu | Arg | Gly | Thr | Asp | Arg | |
| | | | 195 | | | | | 200 | | | | | 205 | | | |
| TCT | CGT | GGT | TAT | GGT | TAC | GTT | GAT | TTT | GAA | AAC | AAA | TCT | TAT | GCT | GAA | 1152 |
| Ser | Arg | Gly | Tyr | Gly | Tyr | Val | Asp | Phe | Glu | Asn | Lys | Ser | Tyr | Ala | Glu | |
| | | 210 | | | | | 215 | | | | | 220 | | | | |
| AAG | GCC | ATT | CAA | GAA | ATG | CAA | GGT | AAG | GAA | ATT | GAT | GGT | AGA | CCA | ATC | 1200 |
| Lys | Ala | Ile | Gln | Glu | Met | Gln | Gly | Lys | Glu | Ile | Asp | Gly | Arg | Pro | Ile | |
| 225 | | | | | 230 | | | | | 235 | | | | | | |
| AAC | TGT | GAT | ATG | TCC | ACA | AGC | AAG | CCA | GCT | GGT | AAC | AAC | GAT | CGT | GCC | 1248 |
| Asn | Cys | Asp | Met | Ser | Thr | Ser | Lys | Pro | Ala | Gly | Asn | Asn | Asp | Arg | Ala | |
| 240 | | | | | 245 | | | | | 250 | | | | | 255 | |
| AAG | AAA | TTC | GGT | GAT | ACC | CCA | TCT | GAA | CCA | TCT | GAC | ACT | TTG | TTC | TTG | 1296 |
| Lys | Lys | Phe | Gly | Asp | Thr | Pro | Ser | Glu | Pro | Ser | Asp | Thr | Leu | Phe | Leu | |
| | | | | 260 | | | | | 265 | | | | | 270 | | |
| GGT | AAC | TTA | TCT | TTC | AAT | GCT | GAC | AGA | GAC | GCT | ATT | TTC | GAA | TTA | TTC | 1344 |
| Gly | Asn | Leu | Ser | Phe | Asn | Ala | Asp | Arg | Asp | Ala | Ile | Phe | Glu | Leu | Phe | |
| | | | 275 | | | | | 280 | | | | | 285 | | | |
| GCT | AAA | CAC | GGT | GAA | GTT | GTT | TCC | GTC | CGT | ATC | CCA | ACA | CAT | CCA | GAA | 1392 |
| Ala | Lys | His | Gly | Glu | Val | Val | Ser | Val | Arg | Ile | Pro | Thr | His | Pro | Glu | |
| | | 290 | | | | | 295 | | | | | 300 | | | | |
| ACT | GAA | CAA | CCA | AAA | GGT | TTC | GGT | TAT | GTT | CAA | TTC | TCC | AAC | ATG | GAG | 1440 |
| Thr | Glu | Gln | Pro | Lys | Gly | Phe | Gly | Tyr | Val | Gln | Phe | Ser | Asn | Met | Glu | |
| | 305 | | | | | 310 | | | | | 315 | | | | | |
| GAC | GCC | AAG | AAG | GCT | CTA | GAC | GCT | TTA | CAA | GGT | GAA | TAC | ATT | GAC | AAC | 1488 |
| Asp | Ala | Lys | Lys | Ala | Leu | Asp | Ala | Leu | Gln | Gly | Glu | Tyr | Ile | Asp | Asn | |
| 320 | | | | | 325 | | | | | 330 | | | | | 335 | |
| AGA | CCA | GTT | AGA | TTA | GAC | TTC | TCT | TCT | CCA | AGA | CCA | AAC | AAC | GAT | GGT | 1536 |
| Arg | Pro | Val | Arg | Leu | Asp | Phe | Ser | Ser | Pro | Arg | Pro | Asn | Asn | Asp | Gly | |
| | | | | 340 | | | | | 345 | | | | | 350 | | |
| GGT | CGT | GGC | GGT | AGC | CGT | GGT | TTT | GGT | GGT | CGT | GGC | GGT | GGT | CGT | GGC | 1584 |
| Gly | Arg | Gly | Gly | Ser | Arg | Gly | Phe | Gly | Gly | Arg | Gly | Gly | Gly | Arg | Gly | |
| | | | 355 | | | | | 360 | | | | | 365 | | | |

-continued

| | | | | | | | | | | | | | | | | |
|---|---|---|---|---|---|---|---|---|---|---|---|---|---|---|---|---|
| GGT | AAC | CGT | GGA | TTC | GGT | GGT | CGT | GGT | GGC | GCT | CGC | GGT | GGC | CGT | GGC | 1632 |
| Gly | Asn | Arg | Gly | Phe | Gly | Gly | Arg | Gly | Gly | Ala | Arg | Gly | Gly | Arg | Gly | |
| | | 370 | | | | 375 | | | | | 380 | | | | | |
| GGT | TTC | AGA | CCA | TCT | GGT | TCT | GGT | GCT | AAT | ACT | GCT | CCA | TTG | GGC | AGA | 1680 |
| Gly | Phe | Arg | Pro | Ser | Gly | Ser | Gly | Ala | Asn | Thr | Ala | Pro | Leu | Gly | Arg | |
| | 385 | | | | | 390 | | | | | 395 | | | | | |
| TCA | AGA | AAT | ACC | GCT | TCT | TTC | GCT | GGT | TCA | AAG | AAA | ACA | TTT | GAT | | 1725 |
| Ser | Arg | Asn | Thr | Ala | Ser | Phe | Ala | Gly | Ser | Lys | Lys | Thr | Phe | Asp | | |
| 400 | | | | | 405 | | | | | 410 | | | | | | |

TAATGAGAAA ATGAAATGAA TTTCAATTTC AATTTTTCT CTTTTTACGT TAATTACTAT 1785

ATTCCATTTT TGAGGAAAAA TTTGGTCTAT AATATTTGT GTACATTAGT AAGTAAATAG 1845

GATACATTCT TAAACCTTTC ATTCACCATC TCTATTTGCC AACTTTTCTT CGAATGGCTT 1905

ACTCTTTTTT TTTTCACGAT GAGATGAGAT CGCTAGATAC GGAAGATTAC AAGGCCTTGG 1965

AAAATACTCA AAAAATTTCA GTAATATGAA ATGAATATCT AAATAAAAGC TT 2017

(2) INFORMATION FOR SEQ ID NO:4:

(i) SEQUENCE CHARACTERISTICS:
        (A) LENGTH: 414 amino acids
        (B) TYPE: amino acid
        (D) TOPOLOGY: linear (ii) MOLECULE TYPE: protein (xi) SEQUENCE DESCRIPTION: SEQ ID NO:4:

| | | | | | | | | | | | | | | | |
|---|---|---|---|---|---|---|---|---|---|---|---|---|---|---|---|
| Met | Ala | Lys | Thr | Thr | Lys | Val | Lys | Gly | Asn | Lys | Lys | Glu | Val | Lys | Ala |
| 1 | | | | 5 | | | | | 10 | | | | | 15 | |
| Ser | Lys | Gln | Ala | Lys | Glu | Glu | Lys | Ala | Lys | Ala | Val | Ser | Ser | Ser | Ser |
| | | | 20 | | | | | 25 | | | | | 30 | | |
| Ser | Glu | Ser | Ser | Ser | Ser | Ser | Ser | Ser | Ser | Glu | Ser | Glu | Ser | Glu | |
| | | 35 | | | | | 40 | | | | | 45 | | | |
| Ser | Glu | Ser | Glu | Ser | Glu | Ser | Ser | Ser | Ser | Ser | Ser | Ser | Asp | Ser | |
| | 50 | | | | | 55 | | | | | 60 | | | | |
| Glu | Ser | Ser | Ser | Ser | Ser | Ser | Ser | Asp | Ser | Glu | Ser | Glu | Ala | Glu | Thr |
| 65 | | | | | 70 | | | | | 75 | | | | | 80 |
| Lys | Lys | Glu | Glu | Ser | Lys | Asp | Ser | Ser | Ser | Ser | Ser | Ser | Asp | Ser | Ser |
| | | | | 85 | | | | | 90 | | | | | 95 | |
| Ser | Asp | Glu | Glu | Glu | Glu | Glu | Glu | Lys | Glu | Glu | Thr | Lys | Lys | Glu | Glu |
| | | | 100 | | | | | 105 | | | | | 110 | | |
| Ser | Lys | Glu | Ser | Ser | Ser | Ser | Asp | Ser | Ser | Ser | Ser | Ser | Ser | Ser | Asp |
| | | 115 | | | | | 120 | | | | | 125 | | | |
| Ser | Glu | Ser | Glu | Lys | Glu | Glu | Ser | Asn | Asp | Lys | Lys | Arg | Lys | Ser | Glu |
| | 130 | | | | | 135 | | | | | 140 | | | | |
| Asp | Ala | Glu | Glu | Glu | Glu | Asp | Glu | Glu | Ser | Ser | Asn | Lys | Lys | Gln | Lys |
| 145 | | | | | 150 | | | | | 155 | | | | | 160 |
| Asn | Glu | Glu | Thr | Glu | Glu | Pro | Ala | Thr | Ile | Phe | Val | Gly | Arg | Leu | Ser |
| | | | | 165 | | | | | 170 | | | | | 175 | |
| Trp | Ser | Ile | Asp | Asp | Glu | Trp | Leu | Lys | Lys | Glu | Phe | Glu | His | Ile | Gly |
| | | | 180 | | | | | 185 | | | | | 190 | | |
| Gly | Val | Ile | Gly | Ala | Arg | Val | Ile | Tyr | Glu | Arg | Gly | Thr | Asp | Arg | Ser |
| | | 195 | | | | | 200 | | | | | 205 | | | |
| Arg | Gly | Tyr | Gly | Tyr | Val | Asp | Phe | Glu | Asn | Lys | Ser | Tyr | Ala | Glu | Lys |
| | 210 | | | | | 215 | | | | | 220 | | | | |
| Ala | Ile | Gln | Glu | Met | Gln | Gly | Lys | Glu | Ile | Asp | Gly | Arg | Pro | Ile | Asn |
| 225 | | | | | 230 | | | | | 235 | | | | | 240 |

| Cys | Asp | Met | Ser | Thr<br>245 | Ser | Lys | Pro | Ala | Gly<br>250 | Asn | Asn | Asp | Arg | Ala<br>255 | Lys |
| Lys | Phe | Gly | Asp<br>260 | Thr | Pro | Ser | Glu | Pro<br>265 | Ser | Asp | Thr | Leu | Phe<br>270 | Leu | Gly |
| Asn | Leu | Ser<br>275 | Phe | Asn | Ala | Asp | Arg<br>280 | Asp | Ala | Ile | Phe | Glu<br>285 | Leu | Phe | Ala |
| Lys | His<br>290 | Gly | Glu | Val | Val | Ser<br>295 | Val | Arg | Ile | Pro | Thr<br>300 | His | Pro | Glu | Thr |
| Glu<br>305 | Gln | Pro | Lys | Gly | Phe<br>310 | Gly | Tyr | Val | Gln | Phe<br>315 | Ser | Asn | Met | Glu | Asp<br>320 |
| Ala | Lys | Lys | Ala | Leu<br>325 | Asp | Ala | Leu | Gln | Gly<br>330 | Glu | Tyr | Ile | Asp | Asn<br>335 | Arg |
| Pro | Val | Arg | Leu<br>340 | Asp | Phe | Ser | Ser | Pro<br>345 | Arg | Pro | Asn | Asn | Asp<br>350 | Gly | Gly |
| Arg | Gly | Gly<br>355 | Ser | Arg | Gly | Phe<br>360 | Gly | Gly | Arg | Gly | Gly<br>365 | Gly | Arg | Gly | Gly |
| Asn | Arg<br>370 | Gly | Phe | Gly | Gly | Arg<br>375 | Gly | Gly | Ala | Arg | Gly<br>380 | Gly | Arg | Gly | Gly |
| Phe<br>385 | Arg | Pro | Ser | Gly | Ser<br>390 | Gly | Ala | Asn | Thr | Ala<br>395 | Pro | Leu | Gly | Arg | Ser<br>400 |
| Arg | Asn | Thr | Ala | Ser<br>405 | Phe | Ala | Gly | Ser | Lys<br>410 | Lys | Thr | Phe | Asp | | |

( 2 ) INFORMATION FOR SEQ ID NO:5:

( i ) SEQUENCE CHARACTERISTICS:
        ( A ) LENGTH: 474 base pairs
        ( B ) TYPE: nucleic acid
        ( C ) STRANDEDNESS: double
        ( D ) TOPOLOGY: unknown ( i i ) MOLECULE TYPE: DNA (genomic)

( v i ) ORIGINAL SOURCE:
        ( A ) ORGANISM: Saccharomyces cerevisiae
        ( B ) STRAIN: S288C ( i x ) FEATURE:
        ( A ) NAME/KEY: misc_feature
        ( B ) LOCATION: 1
        ( D ) OTHER INFORMATION: /note="Base #
        corresponds to base -474 of the sequence listed in
        Figure 4 of the application"

( x i ) SEQUENCE DESCRIPTION: SEQ ID NO:5:

```
GATCTGGTTA TGGTTTTTCT TGACTATAAC CTTAATTATG AGACTAATGT CTTCGGGAGG    60
TCCCTTTTCC GATTTTCCGA CTCTTTTCCG TTGAAGAATG TACTTGTGGT TTTGAATCCT   120
ACGGCAGTTA TTGCGGCGGT TTGGCCCTTT CTTTCAAAGA TTGTGATGGA AATAATTGAT   180
TGTTCCGGGA AATGTGTCTT ATTTTCTAAA AGCATCTTTT TTTCTCTCCA ATTCTTCGAG   240
CTATTTCCAG TAAAGGAAAA AAAAGGTTTG CTGTAAGGGT GAATATGTCT CCAACCTCTT   300
TGAGGTACTG CGTTGCTTCA TTCACCATTT AATATAAATA GTACATTGGC AGCCCTCTTT   360
CAAACGTCAA TTATTCTCGC TTGCCTAACT TTGTTCGGAC CGAAATTATA AAGGCATTCA   420
ATCAGTAACA ATAATTGCTA TTGCATAACT ATACCCTCTG CTAAATAAAA TAAA         474
```

( 2 ) INFORMATION FOR SEQ ID NO:6:

( i ) SEQUENCE CHARACTERISTICS:
        ( A ) LENGTH: 254 amino acids (B) TYPE: amino acid
(D) TOPOLOGY: unknown (ii) MOLECULE TYPE: protein (xi) SEQUENCE DESCRIPTION: SEQ ID NO:6:

| Met | Ala | Tyr | Thr | Lys | Ile | Ala | Leu | Phe | Ala | Ala | Ile | Ala | Ala | Leu | Ala |
|---|---|---|---|---|---|---|---|---|---|---|---|---|---|---|---|
| 1 | | | | 5 | | | | | 10 | | | | | 15 | |

| Ser | Ala | Gln | Thr | Gln | Asp | Gln | Ile | Asn | Glu | Leu | Asn | Val | Ile | Leu | Asn |
|---|---|---|---|---|---|---|---|---|---|---|---|---|---|---|---|
| | | | 20 | | | | | 25 | | | | | 30 | | |

| Asp | Val | Lys | Ser | His | Leu | Gln | Glu | Tyr | Ile | Ser | Leu | Ala | Ser | Asp | Ser |
|---|---|---|---|---|---|---|---|---|---|---|---|---|---|---|---|
| | | 35 | | | | | 40 | | | | | 45 | | | |

| Ser | Ser | Gly | Phe | Ser | Leu | Ser | Ser | Met | Pro | Ala | Gly | Val | Leu | Asp | Ile |
|---|---|---|---|---|---|---|---|---|---|---|---|---|---|---|---|
| | 50 | | | | | 55 | | | | | 60 | | | | |

| Gly | Met | Ala | Leu | Ala | Ser | Ala | Thr | Asp | Asp | Ser | Tyr | Thr | Thr | Leu | Tyr |
|---|---|---|---|---|---|---|---|---|---|---|---|---|---|---|---|
| 65 | | | | | 70 | | | | | 75 | | | | | 80 |

| Ser | Glu | Val | Asp | Phe | Ala | Gly | Val | Ser | Lys | Met | Leu | Thr | Met | Val | Pro |
|---|---|---|---|---|---|---|---|---|---|---|---|---|---|---|---|
| | | | | 85 | | | | | 90 | | | | | 95 | |

| Trp | Tyr | Ser | Ser | Arg | Leu | Glu | Pro | Ala | Leu | Lys | Ser | Leu | Asn | Gly | Asp |
|---|---|---|---|---|---|---|---|---|---|---|---|---|---|---|---|
| | | | 100 | | | | | 105 | | | | | 110 | | |

| Ala | Ser | Ser | Ser | Ala | Ala | Pro | Ser | Ser | Ser | Ala | Ala | Pro | Thr | Ser | Ser |
|---|---|---|---|---|---|---|---|---|---|---|---|---|---|---|---|
| | | 115 | | | | | 120 | | | | | 125 | | | |

| Ala | Ala | Pro | Ser | Ser | Ser | Ala | Ala | Pro | Thr | Ser | Ser | Ala | Ala | Ser | Ser |
|---|---|---|---|---|---|---|---|---|---|---|---|---|---|---|---|
| | 130 | | | | | 135 | | | | | 140 | | | | |

| Ser | Ser | Glu | Ala | Lys | Ser | Ser | Ser | Ala | Ala | Pro | Ser | Ser | Ser | Glu | Ala |
|---|---|---|---|---|---|---|---|---|---|---|---|---|---|---|---|
| 145 | | | | | 150 | | | | | 155 | | | | | 160 |

| Lys | Ser | Ser | Ser | Ala | Ala | Pro | Ser | Ser | Ser | Glu | Ala | Lys | Ser | Ser | Ser |
|---|---|---|---|---|---|---|---|---|---|---|---|---|---|---|---|
| | | | | 165 | | | | | 170 | | | | | 175 | |

| Ala | Ala | Pro | Ser | Ser | Ser | Glu | Ala | Lys | Ser | Ser | Ser | Ala | Ala | Pro | Ser |
|---|---|---|---|---|---|---|---|---|---|---|---|---|---|---|---|
| | | | 180 | | | | | 185 | | | | | 190 | | |

| Ser | Thr | Glu | Ala | Lys | Ile | Thr | Ser | Ala | Ala | Pro | Ser | Ser | Thr | Gly | Ala |
|---|---|---|---|---|---|---|---|---|---|---|---|---|---|---|---|
| | | 195 | | | | | 200 | | | | | 205 | | | |

| Lys | Thr | Ser | Ala | Ile | Ser | Gln | Ile | Thr | Asp | Gly | Gln | Ile | Gln | Ala | Thr |
|---|---|---|---|---|---|---|---|---|---|---|---|---|---|---|---|
| | 210 | | | | | 215 | | | | | 220 | | | | |

| Lys | Ala | Val | Ser | Glu | Gln | Thr | Glu | Asn | Gly | Ala | Ala | Lys | Ala | Phe | Val |
|---|---|---|---|---|---|---|---|---|---|---|---|---|---|---|---|
| 225 | | | | | 230 | | | | | 235 | | | | | 240 |

| Gly | Met | Gly | Ala | Gly | Val | Val | Ala | Ala | Ala | Ala | Met | Leu | Leu |
|---|---|---|---|---|---|---|---|---|---|---|---|---|---|
| | | | | 245 | | | | | 250 | | | | |

(2) INFORMATION FOR SEQ ID NO:7:

(i) SEQUENCE CHARACTERISTICS:
(A) LENGTH: 323 amino acids
(B) TYPE: amino acid
(D) TOPOLOGY: unknown (ii) MOLECULE TYPE: protein (xi) SEQUENCE DESCRIPTION: SEQ ID NO:7:

| Ala | Phe | Asn | Leu | Phe | Val | Gly | Asn | Leu | Asn | Phe | Asn | Lys | Ser | Ala | Pro |
|---|---|---|---|---|---|---|---|---|---|---|---|---|---|---|---|
| 1 | | | | 5 | | | | | 10 | | | | | 15 | |

| Glu | Leu | Lys | Thr | Gly | Ile | Ser | Asp | Val | Phe | Ala | Lys | Asn | Asp | Leu | Ala |
|---|---|---|---|---|---|---|---|---|---|---|---|---|---|---|---|
| | | | 20 | | | | | 25 | | | | | 30 | | |

| Val | Val | Asp | Val | Arg | Ile | Gly | Met | Thr | Arg | Lys | Phe | Gly | Tyr | Val | Asp |
|---|---|---|---|---|---|---|---|---|---|---|---|---|---|---|---|
| | | 35 | | | | | 40 | | | | | 45 | | | |

| Phe | Glu | Ser | Ala | Glu | Asp | Leu | Glu | Lys | Ala | Leu | Glu | Leu | Thr | Gly | Leu |
|---|---|---|---|---|---|---|---|---|---|---|---|---|---|---|---|
| | 50 | | | | | 55 | | | | | 60 | | | | |

```
Lys  Val  Phe  Gly  Asn  Glu  Ile  Leu  Glu  Lys  Pro  Lys  Gly  Lys  Asp
 65             70                       75                            80

Ser  Lys  Lys  Ala  Arg  Thr  Leu  Leu  Ala  Lys  Asn  Leu  Pro  Tyr  Lys  Val
                85                       90                            95

Thr  Gln  Asp  Glu  Leu  Lys  Glu  Val  Phe  Glu  Asp  Ala  Ala  Glu  Ile  Arg
               100                      105                 110

Leu  Val  Ser  Lys  Asp  Gly  Lys  Ser  Lys  Gly  Ile  Ala  Tyr  Ile  Glu  Phe
               115                      120                 125

Lys  Thr  Glu  Ala  Asp  Ala  Glu  Lys  Thr  Phe  Glu  Glu  Lys  Gln  Gly  Thr
          130                      135                 140

Glu  Ile  Asp  Gly  Arg  Ser  Ile  Ser  Leu  Tyr  Tyr  Thr  Gly  Glu  Lys  Lys
145                      150                      155                      160

Gly  Gln  Asn  Ser  Lys  Thr  Leu  Val  Leu  Ser  Asn  Leu  Ser  Tyr  Ser  Ala
               165                      170                      175

Thr  Glu  Glu  Thr  Leu  Gln  Glu  Val  Phe  Glu  Lys  Ala  Thr  Phe  Ile  Lys
               180                      185                      190

Val  Pro  Gln  Asn  Gln  Asn  Gly  Lys  Ser  Lys  Gly  Tyr  Ala  Phe  Ile  Glu
               195                      200                      205

Phe  Ala  Ser  Phe  Glu  Asp  Ala  Lys  Glu  Ala  Leu  Asn  Ser  Cys  Asn  Lys
     210                      215                      220 —

Arg  Glu  Ile  Glu  Gly  Arg  Ala  Ile  Arg  Leu  Glu  Leu  Gln  Gly  Pro  Arg
225                      230                      235                      240

Gly  Ser  Pro  Asn  Ser  Lys  Thr  Leu  Phe  Val  Lys  Gly  Leu  Ser  Glu  Asp
               245                      250                      255

Thr  Thr  Glu  Glu  Thr  Leu  Lys  Glu  Ser  Phe  Asp  Gly  Ser  Val  Arg  Ala
               260                      265                      270

Arg  Ile  Val  Thr  Asp  Arg  Glu  Thr  Gly  Ser  Ser  Lys  Gly  Phe  Gly  Phe
          275                      280                      285

Val  Asp  Phe  Asn  Ser  Glu  Glu  Asp  Ala  Lys  Glu  Ala  Met  Glu  Asp  Gly
     290                      295                      300

Glu  Ile  Asp  Gly  Asn  Lys  Val  Thr  Leu  Asp  Trp  Ala  Lys  Pro  Lys  Gly
305                      310                      315                      320

Glu  Gly  Gly
```

( 2 ) INFORMATION FOR SEQ ID NO:8:

( i ) SEQUENCE CHARACTERISTICS:
        ( A ) LENGTH: 336 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:8:

```
Ser  Ala  Ser  Leu  Tyr  Val  Gly  Asp  Leu  Glu  Pro  Ser  Val  Ser  Glu  Ala
 1              5                       10                           15

His  Leu  Tyr  Asp  Ile  Phe  Ser  Pro  Ile  Gly  Ser  Val  Ser  Ser  Ile  Arg
               20                       25                      30

Val  Cys  Arg  Asp  Ala  Ile  Thr  Lys  Thr  Ser  Leu  Gly  Tyr  Ala  Tyr  Val
          35                       40                      45

Asn  Phe  Asn  Asp  His  Glu  Ala  Gly  Arg  Lys  Ala  Ile  Glu  Gln  Leu  Asn
     50                       55                      60

Tyr  Thr  Pro  Ile  Lys  Gly  Arg  Leu  Cys  Arg  Ile  Met  Trp  Ser  Gln  Arg
 65                       70                      75                      80

Asp  Pro  Ser  Leu  Ser  Gly  Asn  Ile  Phe  Ile  Lys  Asn  Leu  His  Pro  Asp
               85                       90                      95
```

| | | | | | | | | | | | | | | |
|---|---|---|---|---|---|---|---|---|---|---|---|---|---|---|
| Ile | Asp | Asn | Lys | Ala | Leu | Tyr | Asp | Thr | Phe | Ser | Val | Phe | Gly | Asp | Ile |
| | | | 100 | | | | | 105 | | | | 110 | | | |
| Leu | Ser | Ser | Lys | Ile | Ala | Thr | Asp | Glu | Asn | Gly | Lys | Ser | Lys | Gly | Phe |
| | | | 115 | | | | 120 | | | | | 125 | | | |
| Gly | Phe | Val | His | Phe | Glu | Glu | Glu | Gly | Ala | Ala | Lys | Glu | Ala | Ile | Asp |
| | | 130 | | | | 135 | | | | | 140 | | | | |
| Ala | Leu | Asn | Gly | Met | Leu | Leu | Asn | Gly | Gln | Glu | Ile | Tyr | Val | Ala | Pro |
| 145 | | | | | 150 | | | | | 155 | | | | | 160 |
| His | Leu | Ser | Arg | Lys | Glu | Arg | Asp | Tyr | Thr | Asn | Leu | Tyr | Val | Lys | Asn |
| | | | | 165 | | | | | 170 | | | | | 175 | |
| Ile | Asn | Ser | Glu | Thr | Thr | Asp | Glu | Gln | Phe | Gln | Glu | Leu | Phe | Ala | Lys |
| | | | | 180 | | | | 185 | | | | | 190 | | |
| Phe | Gly | Pro | Ile | Val | Ser | Ala | Ser | Leu | Glu | Lys | Asp | Ala | Asp | Gly | Lys |
| | | 195 | | | | | 200 | | | | | 205 | | | |
| Leu | Lys | Gly | Phe | Gly | Phe | Val | Asn | Tyr | Glu | Lys | His | Glu | Asp | Ala | Val |
| | 210 | | | | | 215 | | | | | 220 | | | | |
| Lys | Ala | Val | Glu | Ala | Leu | Asn | Asp | Ser | Glu | Leu | Asn | Gly | Glu | Lys | Leu |
| 225 | | | | | 230 | | | | | 235 | | | | | 240 |
| Tyr | Val | Gly | Arg | Ala | Gln | Lys | Lys | Asn | Glu | Arg | Met | Gly | Val | Asn | Leu |
| | | | 245 | | | | | | 250 | | | | | 255 | |
| Phe | Val | Lys | Asn | Leu | Asp | Asp | Ser | Val | Asp | Asp | Glu | Lys | Leu | Glu | Glu |
| | | | 260 | | | | | 265 | | | | 270 | | | |
| Glu | Phe | Ala | Pro | Tyr | Gly | Thr | Ile | Thr | Ser | Ala | Lys | Val | Met | Arg | Thr |
| | | 275 | | | | | 280 | | | | | 285 | | | |
| Glu | Asn | Gly | Lys | Ser | Lys | Gly | Phe | Gly | Phe | Val | Cys | Phe | Ser | Thr | Pro |
| | 290 | | | | | 295 | | | | | 300 | | | | |
| Glu | Glu | Ala | Thr | Lys | Ala | Ile | Thr | Glu | Lys | Asn | Gln | Gln | Ile | Val | Ala |
| 305 | | | | | 310 | | | | | 315 | | | | | 320 |
| Gly | Lys | Pro | Leu | Tyr | Val | Ala | Ile | Ala | Gln | Arg | Lys | Asp | Val | Arg | Arg |
| | | | | 325 | | | | | 330 | | | | | 335 | |

(2) INFORMATION FOR SEQ ID NO:9:

(i) SEQUENCE CHARACTERISTICS:
        (A) LENGTH: 85 amino acids
        (B) TYPE: amino acid
        (D) TOPOLOGY: unknown (ii) MOLECULE TYPE: protein (xi) SEQUENCE DESCRIPTION: SEQ ID NO:9:

| | | | | | | | | | | | | | | |
|---|---|---|---|---|---|---|---|---|---|---|---|---|---|---|---|
| Phe | Lys | Thr | Leu | Phe | Val | Ala | Arg | Val | Asn | Tyr | Asp | Thr | Thr | Glu | Ser |
| 1 | | | | 5 | | | | | 10 | | | | | 15 | |
| Lys | Leu | Arg | Arg | Glu | Phe | Glu | Val | Tyr | Gly | Pro | Ile | Lys | Arg | Ile | His |
| | | | 20 | | | | | 25 | | | | | 30 | | |
| Met | Val | Tyr | Ser | Lys | Arg | Ser | Gly | Lys | Pro | Arg | Gly | Tyr | Ala | Phe | Ile |
| | | | 35 | | | | | 40 | | | | | 45 | | |
| Glu | Tyr | Glu | His | Glu | Arg | Asp | Met | His | Ser | Ala | Tyr | Lys | His | Ala | Asp |
| | | 50 | | | | | 55 | | | | | 60 | | | |
| Gly | Lys | Lys | Ile | Asp | Gly | Arg | Arg | Val | Leu | Val | Asp | Val | Glu | Arg | Gly |
| 65 | | | | | 70 | | | | | 75 | | | | | 80 |
| Arg | Thr | Val | Lys | Gly | | | | | | | | | | | |
| | | | | 85 | | | | | | | | | | | |

(2) INFORMATION FOR SEQ ID NO:10:

( i ) SEQUENCE CHARACTERISTICS:
  ( A ) LENGTH: 223 amino acids
  ( B ) TYPE: amino acid
  ( D ) TOPOLOGY: unknown ( i i ) MOLECULE TYPE: protein ( x i ) SEQUENCE DESCRIPTION: SEQ ID NO:10:

```
Ser Lys Thr Leu Val Leu Ser Asn Leu Ser Tyr Ser Ala Thr Glu Glu
 1               5                  10                  15
Thr Leu Gln Glu Val Phe Glu Lys Ala Thr Phe Ile Lys Val Pro Gln
            20                  25                  30
Asn Gln Asn Gly Lys Ser Lys Gly Tyr Ala Phe Ile Glu Phe Ala Ser
         35                  40                  45
Phe Glu Asp Ala Lys Glu Ala Leu Asn Ser Cys Asn Lys Arg Glu Ile
     50                  55                  60
Glu Gly Arg Ala Ile Arg Leu Glu Leu Gln Gly Pro Arg Gly Ser Pro
 65                  70                  75                  80
Asn Ala Arg Ser Gln Pro Ser Lys Thr Leu Phe Val Lys Gly Leu Ser
                 85                  90                  95
Glu Asp Thr Thr Glu Glu Thr Leu Lys Glu Ser Phe Asp Gly Ser Val
            100                 105                 110
Arg Ala Arg Ile Val Thr Asp Arg Glu Thr Gly Ser Ser Lys Gly Phe
        115                 120                 125
Gly Phe Val Asp Phe Asn Ser Glu Glu Asp Ala Lys Glu Ala Met Glu
    130                 135                 140
Asp Gly Glu Ile Asp Gly Asn Lys Val Thr Leu Asp Trp Ala Lys Pro
145                 150                 155                 160
Lys Gly Glu Gly Gly Phe Gly Gly Arg Gly Gly Gly Arg Gly Gly Phe
                165                 170                 175
Gly Gly Arg Gly Gly Gly Arg Gly Gly Arg Gly Gly Phe Gly Gly Arg
            180                 185                 190
Gly Arg Gly Gly Phe Gly Gly Arg Gly Gly Phe Arg Gly Gly Arg Gly
        195                 200                 205
Gly Gly Gly Asp His Lys Pro Gln Gly Lys Lys Thr Lys Phe Glu
    210                 215                 220
```

We claim:

1. An isolated yeast gene having the following nucleotide sequence, as in SEQ. ID. NO. 1:

```
  1 GATCTGGTTATGGTTTTTCTTGACTATAACCTT
                AATTATGAGACTAATGTCTTCGGGAGG   60
 61 TCCCTTTTCCGATTTTCCGACTCTTTTCCGTTG
                AAGAATGTACTTGTGGTTTTGAATCCT  120
121 ACGGCAGTTATTGCGGCGGTTTGGCCCTTTCTT
                TCAAAGATTGTGATGGAAATAATTGAT  180
181 TGTTCCGGGAAATGTGTCTTATTTTCTAAAAGC
                ATCTTTTTTTCTCTCCAATTCTTCGAG  240
241 CTATTTCCAGTAAAGGAAAAAAAAGGTTTGCTG
                TAAGGGTGAATATGTCTCCAACCTCTT  300
301 TGAGGTACTGCGTTGCTTCATTCACCATTTAAT
                ATAAATAGTACATTGGCAGCCCTCTTT  360
361 CAAACGTCAATTATTCTCGCTTGCCTAACTTTG
                TTCGGACCGAAATTATAAAGGCATTCA  420
421 ATCAGTAACAATAATTGCTATTGCATAACTATA
                CCCTCTGCTAAATAAAATAAAATGTCC  480
481 GTTTCCAAGATTGCTTTCGTTTTAAGTGCCATT
                GCCTCTTTGGCCGTCGCTGACACCAGC  540
541 GCCGCCGAAACTGCTGAATTGCAAGCTATTATC
                GGTGACATCAACTCTCATCTTTCTGAC  600
601 TACTTGGGTCTAGAAACTGGCAACAGTGGATTC
```

```
                                CAAATTCCATCTGATGTCTTGAGTGTG 660
661 TATCAACAAGTCATGACTTACACCGATGACGCT
                                TACACTACCTTGTTTAGTGAATTGGAC 720
721 TTTGATGCTATCACTAAGACAATTGTTAAATTG
                                CCATGGTACACCACAAGATTGAGTTCT 780
781 GAAATCGCTGCTGCTCTTGCCTCCGTTTCCCCA
                                GCTTCTTCCGAGGCTGCATCTTCTTCC 840
841 GAGGCTGCATCTTCTTCCAAGGCTGCATCTTCT
                                TCCGAAGCTACATCCTCTGCCGCTCCA 900
901 TCCTCTTCTGCTGCCCCATCTTCTTCTGCTGCC
                                CCATCATCATCTGCCGAATCATCTTCT 960
961 AAGGCCGTTTCTTCTTCTGTCGCTCCAACTACC
                                TCTTCTGTCAGCACTTCTACAGTCGAA 1020
1021 ACTGCTTCCAATGCCGGTCAAAGAGTCAATGCA
                                GGCGCTGCCTCTTTCGGTGCTGTTGTT 1080
1081 GCAGGTGCAGCTGCTTTATTGTTATAAAAGGGA
                                ACCTTTTACAACAAATATTTGAAAAAT 1140
1141 TACCTCCATTATTATACCTTCTCTTTATGTAAT
                                TGTTAGTTCGAAAATTTTTTCTTCATT 1200
1201 AATATAATCAACTTCTAAAACTTTCTAAAAACG
                                TTCTCTTTTTCGAGATTAGTGCTTCTT 1260
1261 CCCAATCCGTAAGAAATGTTTCCTTTCTTGACA
                                ATTGGCACCAGCTGGCTACTCGTTGCT 1320
1321 CGAAAACTACTCTCTTTTATTTTTAATTTACGA
                                ACGATTATCTTTCGAAGGAACGACCAA 1380
1381 ACGAGCTAAATATGGGCATCGCCAACGTTAAAA
                                AAATGGACCCTACCGAAGACGTTATTA 1440
1441 TGCCAAGGCGCAGCGAAGAGTCTTTCTCCTTGA
                                GAAAAAATATGCATGAAACAAAATAGA 1500
1501 CAGGACCAGACCCTCTTCGGGAAAAAAAGTCAA
                                GATTTAACACGTGGCTACACCGGCTGG 1560
1561 CTTACAACCAACCAACATAAGATC 1584.
```

2. The nucleotide sequence of claim 1 which encodes the protein having the following amino acids as in SEQ. ID. NO. 2:

```
Met Ser Val Ser Lys Ile Ala Phe Val Leu Ser Ala Ile Ala Ser
 1               5                  10                  15

Leu Ala Val Ala Asp Thr Ser Ala Ala Glu Thr Ala Glu Leu
                 20                  25

Gln Ala Ile Ile Gly Asp Ile Asn Ser His Leu Ser Asp Tyr Leu
 30               35                  40

Gly Leu Glu Thr Gly Asn Ser Gly Phe Gln Ile Pro Ser Asp
 45               50                  55

Val Leu Ser Val Tyr Gln Gln Val Met Thr Tyr Thr Asp Asp
 60               65                  70

Ala Tyr Thr Thr Leu Phe Ser Glu Leu Asp Phe Asp Ala Ile
       75               80                  85

Thr Lys Thr Ile Val Lys Leu Pro Trp Tyr Thr Thr Arg Leu
                 90               95                 100

Ser Ser Glu Ile Ala Ala Ala Leu Ala Ser Val Ser Pro Ala Ser
                105                 110                 115

Ser Glu Ala Ala Ser Ser Ser Glu Ala Ala Ser Ser Ser Lys Ala
                120                 125                 130

Ala Ser Ser Ser Glu Ala Thr Ser Ser Ala Ala Pro Ser Ser Ser
                135                 140                 145

Ala Ala Pro Ser Ser Ser Ala Ala Pro Ser Ser Ser Ala Glu Ser
                150                 155                 160

Ser Ser Lys Ala Val Ser Ser Ser Val Ala Pro Thr Thr Ser Ser
                165                 170                 175

Val Ser Thr Ser Thr Val Glu Thr Ala Ser Asn Ala Gly Gln
                180                 185
```

-continued

Met Ser Val Ser Lys Ile Ala Phe Val Leu Ser Ala Ile Ala Ser
1           5                    10                  15

Arg Val Asn Ala Gly Ala Ala Ser Phe Gly Ala Val Val Ala
190              195                200

Gly Ala Ala Ala Leu Leu Leu.
    205              210

3. A fragment of the yeast gene of claim 1 wherein the nucleotide sequence comprises 137 to 142 bp upstream of the start codon and encodes a promoter element for initiating transcription.

4. The yeast fragment of claim 3 having the following nucleotide sequence as in SEQ. ID. NO. 5:

```
1    G A T C T G G T T A T G G T T T T T C T T G A C-
   T A T A A C C T T A A T T A T G A G A C T A A T G T C T T C G G G A G G    60
61   T C C C T T T T C C G A T T T T C C G A C T C T T T T C-
   C G T T G A A G A A T G T A C T T G T G G T T T T G A A T C C T            120
121  A C G G C A G T T A T T G C G G C G G T T T G G C-
   C C T T T C T T T C A A A G A T T G T G A T G G A A A T A A T T G A T      180
181  T G T T C C G G G A A A T G T G T C T-
   T A T T T T C T A A A A G-
   C A T C T T T T T T T C T C T C C A A T T C T T C G A G                    240
241  C T A T T T C C A G T A A A G G A A A A A A A A G-
   G T T T G C T G T A A G G G T G A A T A T G T C T C C A A C C T C T T      300
301  T G A G G T A C T G C G T T G C T T C A T T C A C-
   C A T T T A A T A T A A A T A G T A C A T T G G C A G C C C T C T T T      360
361  C A A A C G T C A A T T A T T C T C G C T T G C-
   C T A A C T T T G T T C G G A C C G A A A T-
   T A T A A A G G C A T T C A   420
421  A T C A G T A A C A A T A A T T G C T A T T G C A T-
   A A C T A T A C C C T C T G C T A A A T A A A A T A A A                    474.
```

5. An isolated yeast nucleotide sequence from +475 to +1104 of SEQ. ID. NO. 1.

6. A recombinant replicable expression vehicle which comprises a yeast DNA construct comprising the yeast gene of claim 1.

7. A recombinant replicable expression vehicle which comprises a yeast DNA construct comprising the yeast gene of claim 4.

8. The expression vehicle of claim 6 wherein the DNA sequence contains a promoter sequence positioned upstream from 137 to 142 bp of the start codon.

9. The expression vehicle of claim 6 wherein the nucleotide sequence contains the endogenous promotor.

10. The expression vehicle of claim 6 which contains a heterologous promoter.

11. The expression vehicle of claim 10 wherein the promoter is a regulatory region selected from the group of GAL10, GAL1, PGK, ADC1 and GPD.

12. The expression vehicle of claim 6 which is plasmid pYCA1, which is a multicopy expression vehicle.

13. The expression vehicle of claim 6 which comprises the nucleotide sequence which codes the protein of claim 2.

14. The expression vehicle of claim 6 wherein the gene comprises the nucleotide sequence which comprises, 137 to 142 bp upstream of the start codon, a promoter element sequence for initiating transcription.

15. The expression vehicle of claim 6 wherein the gene has the nucleotide sequence from +475 to +1104 of SEQ. ID. NO. 1.

16. A competent transformed yeast which comprises the expression vector of claim 6.

17. The competent transformed yeast of claim 16 which is of the Saccharomyces genus.

18. The competent transformed yeast of claim 17 which is S. cerevisiae.

19. The competent transformed yeast of claim 18 which is an overexpressing strain.

20. The competent transformed yeast of claim 16 wherein the expression vector comprises the nucleotide sequence which codes the protein of claim 2.

21. The competent transformed yeast of claim 16 wherein the expression vector comprises the nucleotide sequence which comprises, 137 to 142 bp upstream of the start codon, a putative promoter element sequence for initiating transcription.

22. The competent transformed yeast of claim 16 wherein the expression vector comprises the nucleotide sequence from +475 to +1104 of SEQ. ID. NO. 1.

23. The competent transformed yeast of claim 16 wherein the expression vector comprises the nucleotide sequence of claim 4.

* * * * *